(12) United States Patent
Kinder, Jr. et al.

(10) Patent No.: US 7,192,980 B2
(45) Date of Patent: Mar. 20, 2007

(54) CERTAIN SUBSTITUTED POLYKETIDES, PHARMACEUTICAL COMPOSITIONS CONTAINING THEM AND THEIR USE IN TREATING TUMORS

(75) Inventors: Frederick R Kinder, Jr., Morristown, NJ (US); Kenneth W Bair, Mountain Lakes, NJ (US); Timothy M Ramsey, Sparta, NJ (US); Michael L Sabio, Randolph, NJ (US)

(73) Assignee: Novartis AG, Basel (CH)

( * ) Notice: Subject to any disclaimer, the term of this patent is extended or adjusted under 35 U.S.C. 154(b) by 61 days.

(21) Appl. No.: 10/951,857

(22) Filed: Sep. 28, 2004

(65) Prior Publication Data

US 2005/0049249 A1 Mar. 3, 2005

Related U.S. Application Data

(63) Continuation of application No. 10/212,535, filed on Aug. 5, 2002, now Pat. No. 6,972,292.

(60) Provisional application No. 60/358,997, filed on Feb. 22, 2002, provisional application No. 60/349,047, filed on Jan. 16, 2002, provisional application No. 60/341,189, filed on Dec. 13, 2001, provisional application No. 60/344,532, filed on Oct. 25, 2001, provisional application No. 60/310,307, filed on Aug. 6, 2001.

(51) Int. Cl.
*A61K 31/535* (2006.01)
*C07C 27/108* (2006.01)

(52) U.S. Cl. .................. 514/478; 514/231.2; 514/738; 544/106; 560/19; 560/24; 568/700

(58) Field of Classification Search ............. 514/231.5, 514/231.2, 478, 738; 544/106; 560/19.24; 568/700
See application file for complete search history.

(56) References Cited

U.S. PATENT DOCUMENTS 6,096,904 A 8/2000 Smith, III et al.
6,127,406 A 10/2000 Gunasekera et al.

FOREIGN PATENT DOCUMENTS

WO WO 98/24429 6/1998
WO WO 00/04865 2/2000
WO WO 02/46150 A2 6/2002

OTHER PUBLICATIONS

Knudsen et al., Acta Obstetricia et Gynecologica Scandanavia, see abstract.*
Grever et al., Seminars in Oncology, 19(6), 1992, pp. 622-629.*
Gunasekera S.P. et al., "Five New Discodermolide Analogues from the Marine Sponge Discodermia Species", Journal of Natural Products, pp. A-F, (2002).
Smith A.B. et al., "Gram-Scale Synthesis of (+)-Discodermolide", Organic Letters, vol. 1, No. 11, pp. 1823-1826 (1999).
Martello, L.A. et al., "The relationship between Taxol and (+)-discodermolide: synthetic analogs and modeling studies", Chemistry & Biology,vol. 8/9, pp. 843-855 (2001).
Marshall J.A. et al., "Total Synthesis of (+)-Discodermolide", J.Org.Chem., vol. 63, No. 22, pp. 7885-7892 (1998).
Harried S.S. et al., "Total Synthesis of (−)-Discodermolide: An Application of a Chelation-Controlled Alkylation Reaction", J.Org. Chem., vol. 62, No. 18, pp. 6098-6099 (1997).
Smith A.B. et al., "Total Synthesis of (−)-Discodermolide", J.Am. Chem.Soc., vol. 117, No. 48, pp. 12011-12012 (1995).
Nerenberg J.B. et al., "Total Synthesis of the Immunosuppressive Agent (−)-Discodermolide", J.Am.Chem.Soc., vol. 115, No. 126, pp. 12621-12622 (1993).
Hung D.T. et al., "Syntheses of Discodermolides Useful for Investigating Microtubule Binding and Stabilization", J.Am.Chem.Soc., vol. 118, No. 45, pp. 11054-11080 (1996).
Curran D.P. et al., "Simultaneous Preparation of Four Truncated Analogues . . . Fluorous Mixture Synthesis", Organic Letters, vol. 4, No. 13, pp. 2233-2235 (2002).

* cited by examiner

*Primary Examiner*—Zinna N. Davis
(74) *Attorney, Agent, or Firm*—Lydia T. McNally

(57) ABSTRACT

The present invention relates to certain substituted polyketides of formula I,

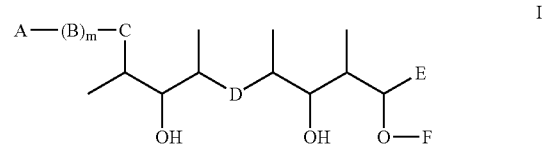

wherein A, B, C, D, E, F and m are as defined herein, pharmaceutical compositions containing said compounds, and the use of said compounds in treating tumors.

19 Claims, No Drawings

CERTAIN SUBSTITUTED POLYKETIDES, PHARMACEUTICAL COMPOSITIONS CONTAINING THEM AND THEIR USE IN TREATING TUMORS

This application is continuation of U.S. application Ser. No. 10/212,535, filed Aug. 5, 2002 now U.S. Pat. No. 6,972,292, which claims the benefit of U.S. Provisional Application No. 60/358,997, filed Feb. 22, 2002; U.S. Provisional Application No. 60/349,047, filed Jan. 16, 2002; U.S. Provisional Application No. 60/341,189, filed Dec. 13, 2001; U.S. Provisional Application No. 60/344,532, filed Oct. 25, 2001; and U.S. Provisional Application No. 60/310,307, filed Aug. 6, 2001.

FIELD OF THE INVENTION

The present invention relates to the area of chemotherapeutic agents and, more particularly, relates to certain substituted polyketides, and the use of said polyketides in treating tumors.

BACKGROUND OF THE INVENTION

Cancer is a serious health problem throughout the world. For example, cancer incidence in the U.S. has increased 30% during the past 30 years, and is expected to continue to increase into the next century. This is attributable to the increased prevalence of cigarette smoking in women compared to men, general aging of the population, and enhanced diagnostic capabilities, as well as potential decreases in mortality from other causes. As a result, an extensive number of research endeavors has been undertaken in an effort to develop therapies appropriate to the treatment and alleviation of cancer in humans.

In the chemotherapeutic area, research has been conducted to develop anti-tumor agents effective against various types of cancer. Oftentimes, anti-tumor agents which have been developed and found effective against cancer cells are, unfortunately, also toxic to normal cells. This toxicity manifests itself in weight loss, nausea, vomiting, hair loss, fatigue, itching, hallucinations, loss of appetite, etc., upon administration of the anti-tumor agent to a patient in need of cancer chemotherapy.

Furthermore, conventionally used chemotherapeutic agents do not have the effectiveness desired or are not as broadly effective against different types of cancers as desired. As a result, a great need exists for chemotherapeutic agents which are not only more effective against all types of cancer, but which have a higher degree of selectivity for killing cancer cells with no or minimal effect on normal healthy cells. In addition, highly effective and selective anti-tumor agents, in particular, against cancers of the colon, bladder, prostate, stomach, pancreas, breast, lung, liver, brain, testis, ovary, cervix, skin, vulva and small intestine are desired. Moreover, anti-tumor activity against colon, breast, lung and prostate cancers as well as melanomas are particularly desired because of the lack of any particular effective therapy at the present time.

(+)-Discodermolide is a novel polyketide natural product that was isolated from extracts of the marine sponge *Discodermia dissoluta* by researchers at the Harbor Branch Oceanographic Institution (HBOI) (Gunasekera S P, Gunasekera M, Longley R E, Schulte G K. Discodermolide: a new bioactive polyhydroxylated lactone from the marine sponge *Discodermia dissoluta*. [published erratum appears in J. Org. Chem. 1991;56:1346]. J. Org. Chem. 1990;55:4912–15.). Discodermolide lacks obvious structural resemblance to paclitaxel, yet it shares with paclitaxel (the active substance in the drug Taxol) the ability to stabilize microtubules. In mechanism-based assays, discodermolide is more effective than paclitaxel. In fact, of the handful of compounds known to induce polymerization of purified tubulin, discodermolide is the most potent. However, microtubules, the major structural component in cells, are not simple equilibrium polymers of tubulin. They exist as regulated GTP-driven dynamic assemblies of heterodimers of α and β tubulin. Although the dynamics are relatively slow in interphase cells, upon entering mitosis, the rate of growing and shortening increases 20- to 100-fold— the average microtubule turns over half the tubulin subunits every ten seconds. This change in rate allows the cytoskeletal microtubule network to dismantle and a bipolar spindle-shaped array of microtubules to assemble. The spindle attaches to chromosomes and moves them apart. The response to complete suppression of microtubule dynamics in cells is death. However, mitotic cells are more sensitive and the tolerance threshold appears to be cell-type specific. Molecules like paclitaxel that bind with high affinity to microtubules disrupt the dynamics process in tumor cells with lethal results even when the ratio of bound drug to tubulin is very low. Discodermolide binds to tubulin competitively with paclitaxel. Since paclitaxel has proven to be useful in treating some cancers, other compounds of the same mechanistic class may have utility against hyperproliferative disorders.

Development of discodermolide or structurally related analogues is hindered by the lack of a reliable natural source of the compound or a feasible synthetic route. Naturally occurring discodermolide is scarce and harvesting the producing organism presents logistical problems. There is an ever-growing need for improved syntheses that enable production of multi-gram amounts of discodermolide and structurally related analogues.

DESCRIPTION OF THE PRIOR ART

Martello et al., "The Relationship Between Taxol and (+)-Discodermolide: Synthetic Analogs and Modeling Studies", Chem. Biol., Vol. 8, No. 9, pp. 843–855 (2001).

Nerenberg et al., "Total Synthesis of the Immunosuppressive Agent (−)-Discodermolide", J. Am. Chem. Soc., Vol. 115, pp. 12621–12622 (1993).

Hung et al, "Syntheses of Discodermolides Useful for Investigating Microtubule Binding and Stabilization", J. Am. Chem. Soc., Vol. 118, pp. 11054–11080 (1996).

Smith et al, "Total Synthesis of (−)-Discodermolide", J. Am. Chem. Soc., Vol. 117, pp. 12011–12012 (1995).

Harried et al., "Total Synthesis of (−)-Discodermolide: An Application of a Chelation-Controlled Alkylation Reaction", J. Org. Chem., Vol. 62, pp. 6098–6099 (1997).

Marshall et al., "Total Synthesis of (+)-Discodermolide", J. Org. Chem., Vol. 63, pp. 7885–7892 (1998).

Halstead, "I. Total Synthesis of (+)-Miyakolide. II. Total Synthesis of (−)-Discodermolide. Ill. Total Synthesis of (+)-Discodermolide (Dissertation)." Cambridge (Mass): Harvard University (1998).

Smith et al., "Gram-Scale Synthesis of (+)-Discodermolide", Org. Lett., Vol. 1, pp. 1823–1826 (1999).

Paterson et al, "Total Synthesis of the Antimicrotubule Agent (+)-Discodermolide Using Boron-Mediated Aldol Reactions of Chiral Ketones", Angew. Chem., Int. Ed., Vol. 39, pp. 377–380 (2000).

Smith et al., "Preparation of Intermediates For the Synthesis of Discodermolides and Their Polyhydroxy Dienyl Lactone Derivatives For Pharmaceutical Use", U.S., Cont.-in-part of U.S. Pat. No. 5,789,605, 83 pp. (2000).

Smith et al., "Preparation of Intermediates For the Synthesis of Discodermolides and Their Polyhydroxy Dienyl Lactone Derivatives For Pharmaceutical Use", PCT Int. Appl., 201 pp. (2000).

Smith et al, "Synthetic Techniques and Intermediates For Polyhydroxy, Dienyllactones and Mimics Thereof", PCT Int. Appl., 194 pp. (1998).

Gunasekera, et al., "Synthesis, Antitumor Activity and Formulations of Discodermolide Acetates", U.S., 9 pp. (2000).

SUMMARY OF THE INVENTION

The present invention provides new anti-tumor agents which are effective against a variety of cancer cells. More particularly, the present invention relates to certain substituted polyketides which exhibit a higher degree of selectivity in killing cancer cells. In addition, the present invention provides pharmaceutical compositions useful in treating tumors comprising a therapeutically effective amount of a certain substituted polyketide. Moreover, the present invention provides a method of treating tumors comprising administering to a mammal afflicted therewith a therapeutically effective amount of a certain substituted polyketide.

DETAILED DESCRIPTION OF THE INVENTION

The essence of the instant invention is the discovery that certain substituted polyketides are useful in treating tumors. In one embodiment, the instant invention provides new anti-tumor agents of formula I:

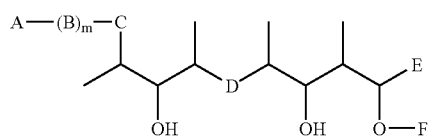

where A is H, $(C_{1-16})$alkyl, $(C_{1-6})$hydroxyalkyl, $-(CH_2)_q CH(CO_2R_1)R_4$,

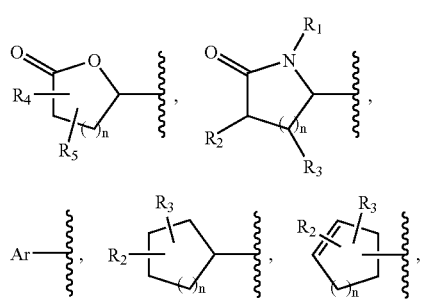

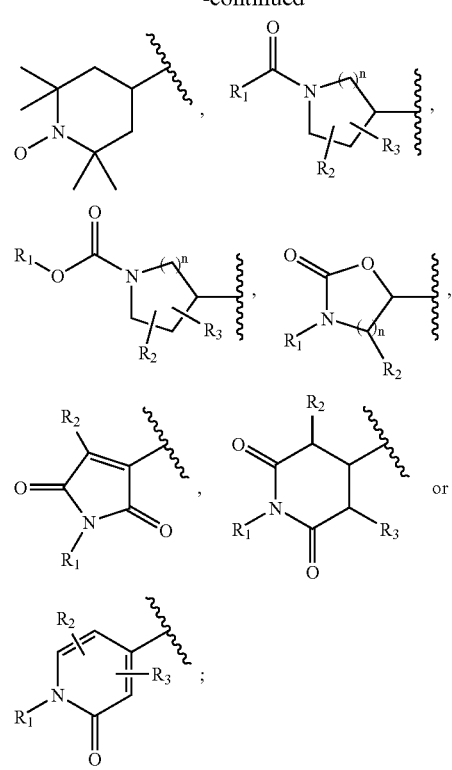

B is $-CH_2CH(OR_1)-$, $-CH_2CH(OC(O)R_1)-$, $-OCH(R_4)-$, $-N(R_1)C(O)-$, $-CH_2C(O)-$ or $-CH_2CH_2-$;

C is $-C(R_4)=C(R_4)-$, $-OCH(R_4)-$, $-N(R_1)CH_2-$, $-N(R_1)C(O)-$ or $-CH_2CH_2-$;

D is $-CH=C(R_4)CH_2-$;

E is $-CH(R_4)CH=CHCH=CH_2$, $-CH(R_4)R_5$, $-CH(R_4)CH=CHR_1$, $-CH(R_4)CH=CHC(O)OR_5$, $-CH(R_4)CH=CHC(O)N(R_4)R_1$, $-CH(R_4)CH_2OR_5$ or Ar;

F is H, $-C(O)N(R_1)_2$, $-C(O)NHCH_2(CH_2)_nN(CH_3)_2$, or $-C(O)NHCH_2(CH_2)_n$-4-morpholino;

$R_1$ is H, $(C_{1-6})$alkyl, $(C_{1-6})$alkyl-Ar or Ar;

Ar is an aromatic or heteroaromatic ring selected from

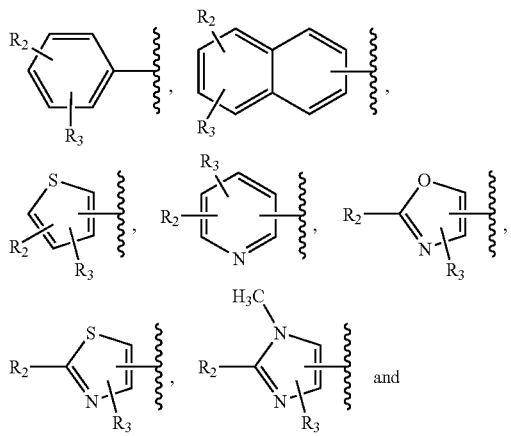

-continued

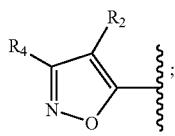

R$_2$ and R$_3$ are, independently, H, (C$_{1-6}$)alkyl, OH, O(C$_{1-6}$) alkyl, OCH$_2$(CH$_2$)$_n$OH, O(CH$_2$)$_n$CO$_2$H, OCH$_2$(CH$_2$)$_n$N(CH$_3$)$_2$, OCH$_2$(CH$_2$)$_n$-4-morpholino, F, Cl, Br or CF$_3$;

R$_4$ is H or (C$_{1-4}$)alkyl;

R$_5$ is (C$_{1-6}$)alkyl, (C$_{1-4}$)alkyl-Ar or Ar;

m is 0 or 11;

n is 1 or 2; and q is 0–6;

with the proviso that when A is Ar or

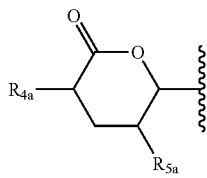

where each of R$_{4a}$ and R$_{5a}$ is (C$_{1-4}$)alkyl, then either:

B cannot be —CH$_2$CH(OH)— or —CH$_2$C(O)—, or C cannot be —CH=CH—, or D cannot be —CH=C(CH$_3$)CH$_2$—, or E cannot be —CH(CH$_3$)CH=CHCH=CH$_2$, or F cannot be —C(O)NH$_2$, and with the provisos that when A is

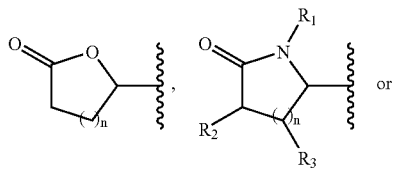

then B cannot be —OCH(R$_4$)— or —N(R)C(O)—, and when B is —CH$_2$CH(OH)— or —OCH(R$_2$)—, then C cannot be —OCH(R$_4$)—, —N(R$_1$)CH$_2$— or C—N(R$_1$)C(O)—, and with the further proviso that the compound of formula I is not a compound of formulae

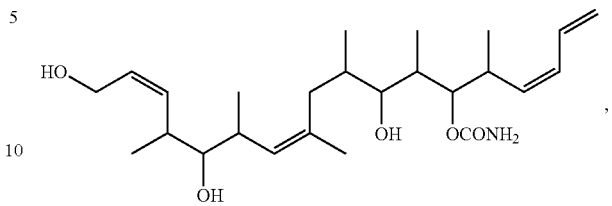

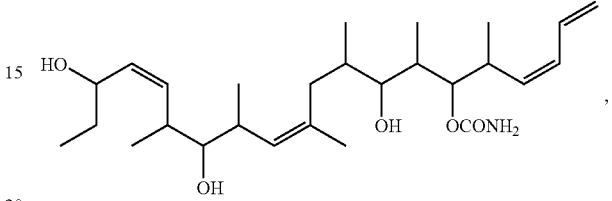

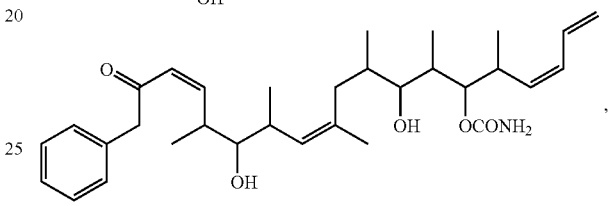

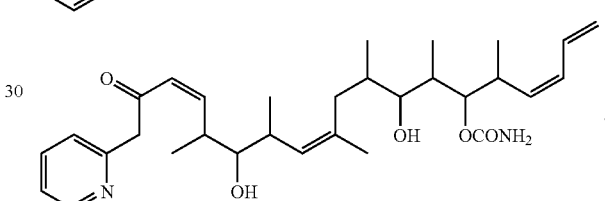

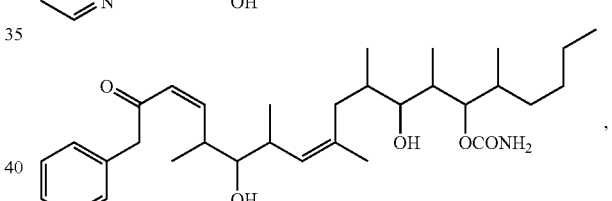

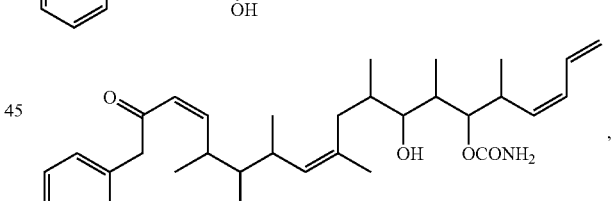

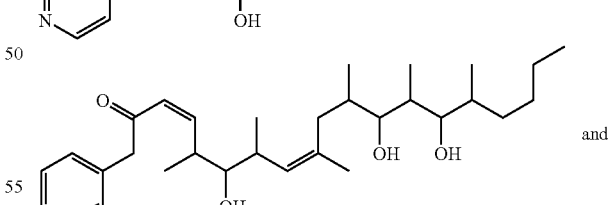

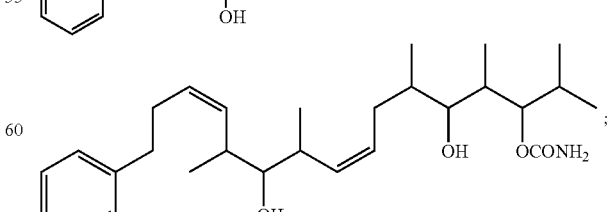

or an acid or base addition salt thereof, where possible.

Preferred compounds are those of formula Ia:

[Structure Ia: A'—(B')ₘ—C' connected to chain with OH, OH, O—F' groups]

where A' is H, (C₁₋₆)alkyl,

[Various ring structures shown including lactone with R₄', R₅'; piperidinone with R₁'; Ar'; cyclopentyl; tetramethylpiperidine N-oxide; piperidine with R₁'C(O)—; piperidine carbamate with R₁'O—; oxazolidinone with R₁', n; maleimide with R₁'; glutarimide with R₁'; pyridinone with R₁']

B' is —CH₂CH(OR₁')—, —CH₂CH(OC(O)R₁')—, —OCH₂—, —N(R₁')C(O)—, —CH₂C(O)— or —CH₂CH₂—;

C' is —CH=CH—, —OCH₂—, —N(R₁')CH₂—, —N(R₁')C(O)— or —CH₂CH₂—;

D' is —CH=C(R₄')CH₂—;

E' is —CH(R₄')CH=CHCH=CH₂, —CH(R₄')R₅', —CH(R₄')CH=CHR₁', —CH(R₄')CH=CHC(O)OR₅', —CH(R₄')CH=CHC(O)N(R₄')R₁', —CH(R₄')CH₂OR₅ or Ar';

F' is H, —C(O)N(R₁')₂, —C(O)NHCH₂(CH₂)ₙN(CH₃)₂ or —C(O)NHCH₂(CH₂)ₙ-4-morpholino;

R₁' is H, (C₁₋₃)alkyl, (C₁₋₃)alkyl-Ar' or Ar';

Ar' is, selected from

[Phenyl with R₂', R₃'; naphthyl; thiophene; pyridine]

R₂' and R₃' are, independently, H, (C₁₋₆)alkyl, OH, O(C₁₋₃)alkyl, OCH₂(CH₂)ₙOH, O(CH₂)ₙCO₂H, OCH₂(CH₂)ₙN(CH₃)₂, OCH₂(CH₂)ₙ-4-morpholino, F, Cl, Br or CF₃;

R₄' is H or (C₁₋₃)alkyl;

R₅' is (C₁₋₆)alkyl, (C₁₋₃)alkyl-Ar' or Ar';

m is 0 or 1; and n is 1 or 2;

and wherein the foregoing provisos apply;

or an acid or base addition salt thereof, where possible.

More preferred compounds are those of formula Ib:

[Structure Ib: A"—(B")ₘ—C" connected to chain with OH, OH, O—C(O)NH₂ groups]

where A" is H, (C₁₋₆)alkyl,

[Various ring structures shown including lactone with R₄", R₅"; Ar"; cyclopentyl; tetramethylpiperidine N-oxide; glutarimide with R₁"; pyridinone with R₁"; oxazolidinone with R₁"]

B" is —CH₂CH(OR₁")—, —CH₂CH(OC(O)R₁")—, —OCH₂—, —N(R₁")C(O)—, —CH₂C(O)— or —CH₂CH₂—;

C″ is —CH=CH—, —OCH$_2$—, —N(R$_{1''}$)CH$_{2'''}$—, —N(R$_{1''}$)C(O)— or —CH$_2$CH$_2$—;

D″ is —CH=C(R$_{4''}$)CH$_2$—;

E″ is —CH(R$_{4''}$)CH=CHCH=CH$_2$, —CH(R$_{4''}$)R$_{5''}$, —CH(R$_{4''}$)CH=CHR$_{1''}$, —CH(R$_{4''}$)CH=CHC(O)OR$_{5''}$, —CH(R$_{4''}$)CH=CHC(O)N(R$_{4''}$)R$_1$″, —CH(R$_{4''}$)CH$_2$OR$_{5''}$ or Ar″;

R$_{1''}$ is H, (C$_{1-3}$)alkyl, CH$_2$—Ar″ or Ar″;

Ar″ is selected from

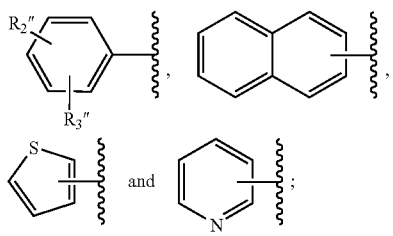

R$_{2''}$ and R$_{3''}$ are, independently, H, (C$_{1-6}$)alkyl, OH, OCH$_3$, OCH$_2$CH$_2$OH, OCH$_2$CO$_2$H, OCH$_2$(CH$_2$)$_n$N(CH$_3$)$_2$, OCH$_2$(CH$_2$)$_n$-4-morpholino, F, Cl, Br or CF$_3$;

R$_{4''}$ is H or CH$_3$;

R$_{5''}$ is (C$_{1-6}$)alkyl, —CH$_2$—Ar″ or Ar″ m is 0 or 1; and n is 1 or 2;

and wherein the foregoing provisos apply;

or an acid or base addition salt thereof, where possible.

Even more preferred compounds are those of formula Ic:

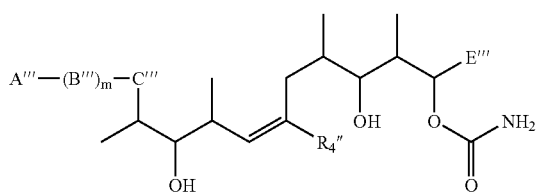

Ic where A‴ is H, (C$_{1-6}$)alkyl,

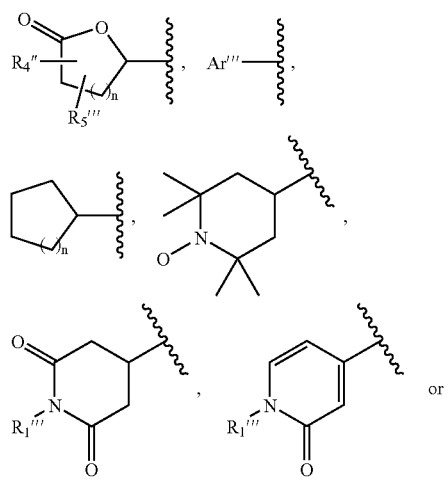

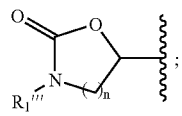

-continued

B‴ is —CH$_2$CH(OR$_{1''''}$—)—, —CH$_2$CH(OC(O)R$_{1'''}$)—, —OCH$_{2'''}$—, —N(R$_{1'''}$)C(O)—, —CH$_2$C(O)— or —CH$_2$CH$_2$—;

C‴ is —CH=CH—, —OCH$_2$—, —N(R$_{1'''}$)CH$_2$—, —N(R$_{1'''}$)C(O)— or —CH$_2$CH$_2$—;

E‴ is —CH(R$_{4'''}$)CH=CHCH=CH$_2$, —CH(R$_{4'''}$)R$_{5'''}$, —CH(R$_{4'''}$)CH=CHR$_{1'''}$, —CH(R$_{4'''}$)CH=CHC(O)OR$_{5'''}$, —CH(R$_{4'''}$)CH=CHC(O)N(R$_{4'''}$)R$_{1'''}$, —CH(R$_{4'''}$)CH$_2$OR$_{5'''}$ or Ar‴;

R$_{1'''}$ is H, —CH$_3$, CH$_2$—Ar‴ or Ar‴;

Ar‴ is selected from

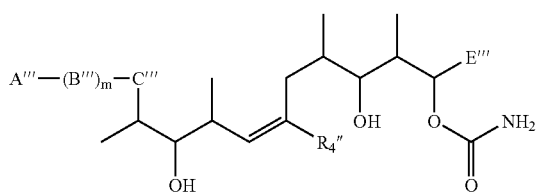

R$_{2'''}$ and R$_{3'''}$ are, independently, H, (C$_{1-4}$)alkyl, OH, OCH$_3$, OCH$_2$CO$_2$H, OCH$_2$(CH$_2$)$_n$N(CH$_3$)$_2$, OCH$_2$(CH$_2$)$_n$-4-morpholino, F, Cl, Br or CF$_3$;

R$_{4'''}$ is as defined above;

R$_{5'''}$ is (C$_1$)alkyl, —CH$_2$—Ar‴ or Ar‴;

m is 0 or 1; and n is 1 or 2;

and wherein the foregoing provisos apply;

or an acid or base addition salt thereof, where possible.

In another embodiment, the instant invention provides pharmaceutical compositions useful in treating tumors comprising a pharmaceutically acceptable carrier or diluent and a therapeutically effective amount of a compound of formula I above, or a pharmaceutically acceptable acid or base addition salt thereof, where possible, preferably a compound of formula Ia above, or a pharmaceutically acceptable acid or base addition salt thereof, where possible, more preferably a compound of formula Ib above, or a pharmaceutically acceptable acid or base salt thereof, where possible, and even more preferably a compound of formula Ic above, or a pharmaceutically acceptable acid or base addition salt thereof, where possible.

In still another embodiment, the instant invention provides a method for treating tumors comprising administering to a mammal in need of such treatment a therapeutically effective amount of a compound of formula I above, or a pharmaceutically acceptable acid or base addition salt thereof, where possible, preferably a compound of formula Ia above, or a pharmaceutically acceptable acid or base addition salt thereof, where possible, more preferably a compound of formula Ib above, or a pharmaceutically acceptable acid or base addition salt thereof, where possible, and even more preferably a compound of formula Ic above, or a pharmaceutically acceptable acid or base addition salt thereof, where possible.

In the above definitions: 0.1) the alkyl groups containing 1 to 6 carbon atoms are either straight or branched chain or cycloalkane, of which examples include isopropyl, isobutyl, t-butyl, isopentyl, neopentyl, isohexyl, 3-methylpentyl, 2,2-dimethylbutyl, 2,3-dimethylbuty, 1,1,2,2-tetramethylethyl, cyclopentyl and cyclohexyl.

Although the pharmaceutically acceptable acid or base addition salts are preferred, it should be understood that all-of the acid or base addition salts of the compounds of formula I are intended to be included within the scope of the present invention.

The acid addition salts of the compounds of formula I may be those of pharmaceutically acceptable organic or inorganic acids. Although the preferred acid addition salts are those of hydrochloric and methanesulfonic acid, salts of sulfuric, phosphoric, citric, fumaric, maleic, benzoic, benzenesulfonic, succinic, tartaric, lactic and acetic acid may also be utilized.

Likewise, the base addition salts of the compounds of formula I may be those of pharmaceutically acceptable organic or inorganic bases. Preferred base addition salts are those derived from pharmaceutically acceptable inorganic bases, more preferably ammonium hydroxide or an alkali or alkaline earth metal hydroxide, e.g, lithium hydroxide, sodium hydroxide, potassium hydroxide, calcium hydroxide, magnesium hydroxide and manganese hydroxide.

The substituted polyketides of formula I may be prepared as depicted below. In the event that the groups A–F contain free hydroxy groups, then the asterisk designation (for example A*) indicates that those groups are protected with acid labile protecting groups (for example TBS). All acid labile protecting groups covered by the asterisk are removed in the final step (HCl).

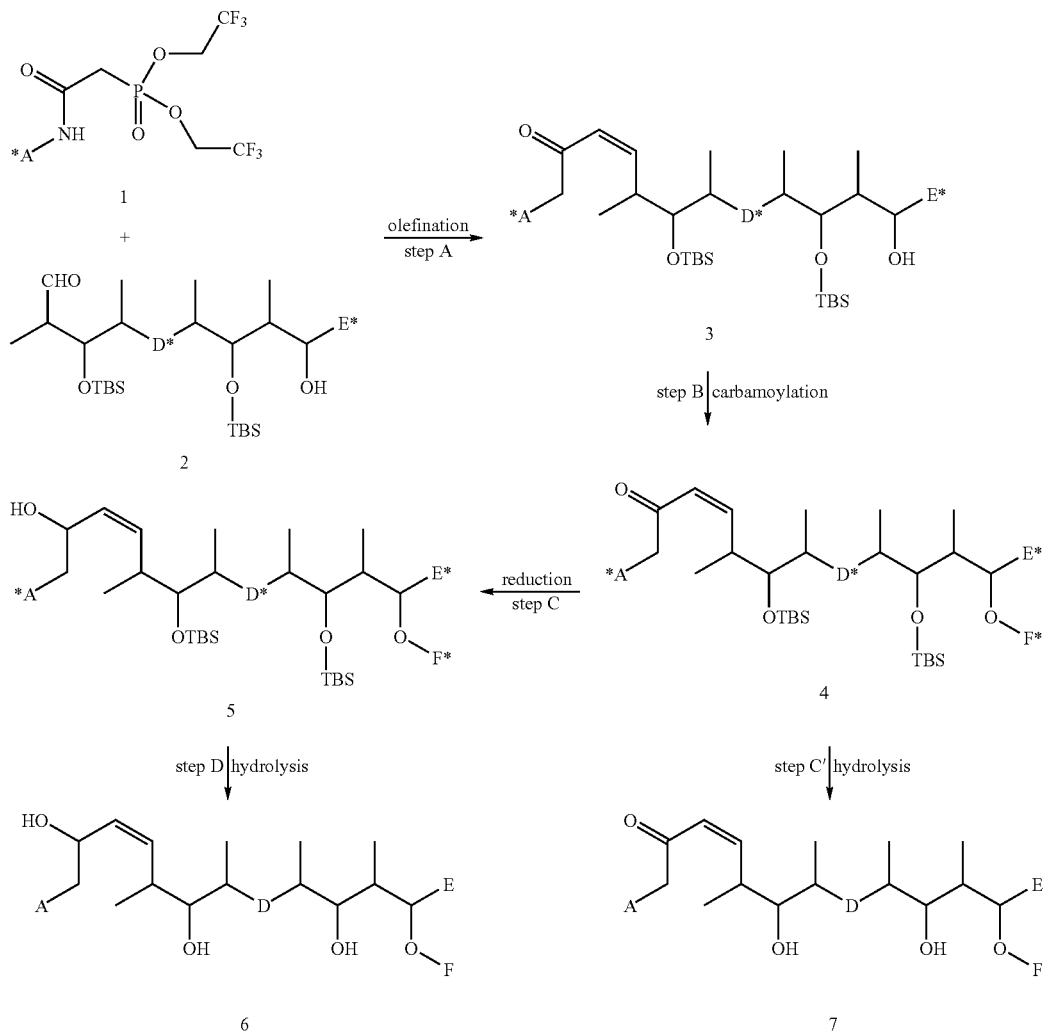

Scheme 1 where each A, D, E, and F is as defined above.

As to the individual steps in Scheme 1, Step A involves the olefination of an aldehyde of formula 2 with a phosphonate of formula 1 to obtain an olefin of formula 3. The olefination is conducted in the presence of: 1) a strong base, preferably a potassium salt such as potassium hexamethyldisilazide; 2) a crown ether such 18-crown-6; and 3) an inert organic solvent, preferably a hydrocarbon such as toluene, at a temperature of between −78° C. and 25° C., preferably at 0° C., for a period of between 10 minutes and 48 hours, preferably for 3 hours.

Step B concerns the carbamoylation of the olefin of formula 3 with a an isocyanate either of formula F*NCO or Cl$_3$C(O)NCO to give a carbamate of formula 4. In the case of using F*NCO, the carbamoylation is conducted in the presence of a Lewis acid such as Bu$_2$Sn(OAc)$_2$ or weak base such as triethylamine, in a polar aprotic solvent, preferably a halogenated solvent such as methylene chloride at a temperature of between −20° C. and 100° C., preferably between 0° C. and 50° C., for a period of between 5 minutes and 72 hours, preferably between 1 hour and 24 hours. In the case using Cl$_3$C(O)NCO, which produces substituted polyketides of formula I where F=H, the carbamoylation is conducted in the presence of a polar aprotic solvent, preferably a halogenated solvent such as methylene chloride at a temperature of between −20° C. and 100° C., preferably at 25° C., for a period of between 5 minutes and 72 hours, preferably between 1 hour and 8 hours; the work-up of this step is conducted in the presence of a protic organic solvent, preferably an alcohol such as methanol, in the presence of a base, for example, a carbonate such as potassium carbonate, at a temperature of between between 0° C. and 100° C., preferably at 25° C., for a period of between 5 minutes and 72 hours, preferably between 1 hour and 8 hours.

Step C concerns the reduction of carbamate 4 to a hydroxy compound of formula 5. The reduction is conducted in the presence of: 1) a hydride, preferably a borane such as catechol borane; 2) a catalyst, preferably a chiral alkyl boron catalyst such as (R)-tetrahydro-1-butyl-3,3-diphenyl-1H, 3H-pyrrolo[1,2-c][1,3,2]oxazaborole; and 3) an inert organic solvent, preferably a hydrocarbon such as toluene, at a temperature of between −78° C. and 25° C., preferably at −20° C., for a period of between 10 hours and 7 days, preferably for 1–4 days.

Step D concerns the hydrolysis of hydroxy compound 5 to a substituted polyketide of formula 6. The hydrolysis reaction is conducted in the presence of: 1) a protic acid, preferably an aqueous protic acid solution, preferably an aqueous hydrogen halide solution, such as aqueous hydrogen chloride; and 2) a polar organic solvent, preferably a mixture of polar organic solvents, preferably a mixture of an aliphatic alcohol and an ether, such as methanol and tetrahydrofuran, at a temperature of between −20° C. and 40° C., preferably between 20° C. and 25° C., for a period of 8 hours and 7 days, preferably between 16 and 72 hours, more preferably between 24 and 48 hours.

Alternative to reduction, Step C' concerns the hydrolysis of carbamate 4 to a different substituted polyketide of formula 7. The hydrolysis reaction is conducted in the presence of: 1) a protic acid, preferably an aqueous protic acid solution, preferably an aqueous hydrogen halide solution, such as aqueous hydrogen chloride; and 2) a polar organic solvent, preferably a mixture of polar organic solvents, preferably a mixture of an aliphatic alcohol and an ether, such as methanol and tetrahydrofuran, at a temperature of between −20° C. and 40° C., preferably between 20° C. and 25° C., for a period of 8 hours and 7 days, preferably between 16 and 72 hours, more preferably between 24 and 48 hours.

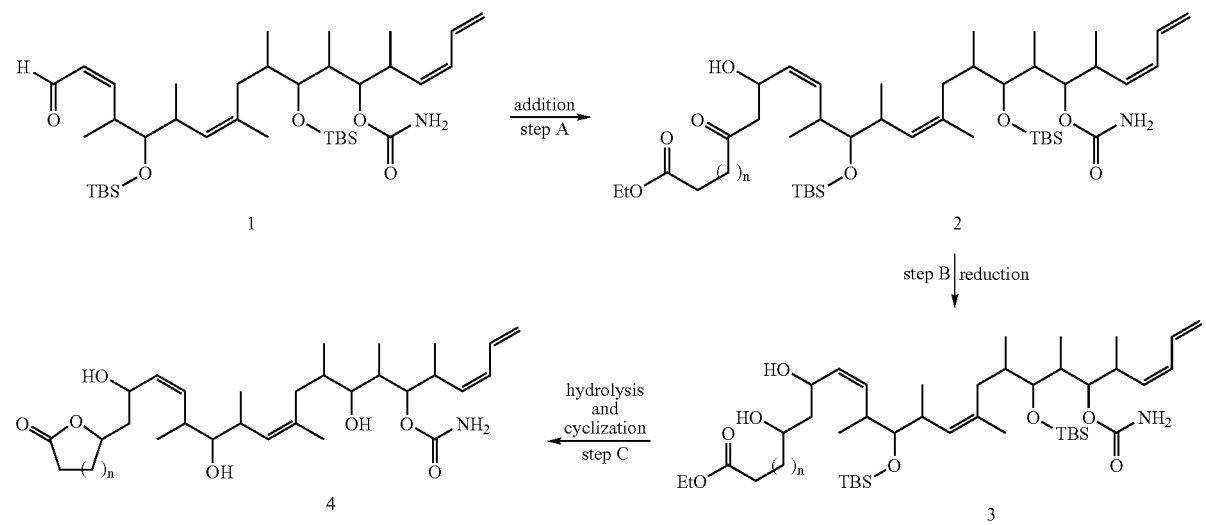

Scheme 2

As to the individual steps in Scheme 2, Step A involves the addition of a ketone of formula EtO$_2$CCH$_2$(CH$_2$)nC(O)CH$_3$ where n is as defined above with an aldehyde of formula 1 to obtain a hydroxyketone of formula 2. The addition requires between 1 and 20 equivalents of the ketone EtO$_2$CCH$_2$(CH$_2$)nC(O)CH$_3$ relative to aldehyde 1, preferably between 5 and 15 equivalents of the ketone EtO$_2$CCH$_2$(CH$_2$)nC(O)CH$_3$ relative to aldehyde 1. The coupling is conducted in the presence of: 1) a dialkylboron halide or triflate, preferably a chiral boron chloride or triflate, more preferably B-chlorodiisopinocampheylborane; 2) a base, preferably an amine, more preferably triethylamine; and 3) a polar organic solvent, preferably an ether, more preferably diethyl ether, at a temperature of between −100° C. and 20° C., preferably between −78° C. and −20° C., for a period of between 2 and 72 hours, preferably for 16 hours.

Step B concerns the reduction of the ketone group common to hydroxyketones of formula 2, to obtain a 1,3-diol compound of formula 3. The reduction is conducted in the presence of: 1) a ketone reducing agent, preferably a borohydride such as tetramethylammonium triacetoxyborohydride; 2) a polar organic solvent, preferably acetonitrile; and 3) a protic solvent, preferably a carboxylic acid, such as acetic acid, at a temperature of between −78° C. and 20° C., preferably between 40° C. and −10° C., for a period of between 2 and 72 hours, preferably for 16 hours.

Step C concerns the hydrolysis and cyclization of the 1,3-diol compound 3 to a substituted polyketide of formula 4. The hydrolysis reaction is conducted in the presence of: 1) a protic acid, preferably an aqueous protic acid solution, preferably an aqueous hydrogen halide solution, such as aqueous hydrogen chloride; and 2) a polar organic solvent, preferably a mixture of polar organic solvents, preferably a mixture of an aliphatic alcohol and an ether, such as methanol and tetrahydrofuran, at a temperature of between −20° C. and 40° C., preferably between 20° C. and 25° C., for a period of 8 hours and 7 days, preferably between 16 and 72 hours, more preferably between 24 and 48 hours.

methylene chloride or ethyl acetate, at a temperature of between −10° C. and 50° C., preferably between −5° C. and 20° C., for a period of between 10 minutes and 24 hours, preferably for 2 hours.

Step B concerns the carbamoylation of the carbonate of formula 2, to obtain a carbamate compound of formula 3. The carbamoylation is conducted in the presence of: 1) an amine of formula A*NHR$_1$*, where A* and R$_1$* are as defined above; and 2) a polar organic solvent, such as methylene chloride or ethyl acetate, at a temperature of between −78° C. and 50° C., preferably between −20° C. and 25° C., for a period of between 2 and 72 hours, preferably for 16 hours.

Step C concerns the carbamoylation of the carbamate of formula 3 with a an isocyanate either of formula F*NCO or Cl$_3$C(O)NCO to give a bis(carbamate) of formula 4. In the case of using F*NCO, the carbamoylation is conducted in

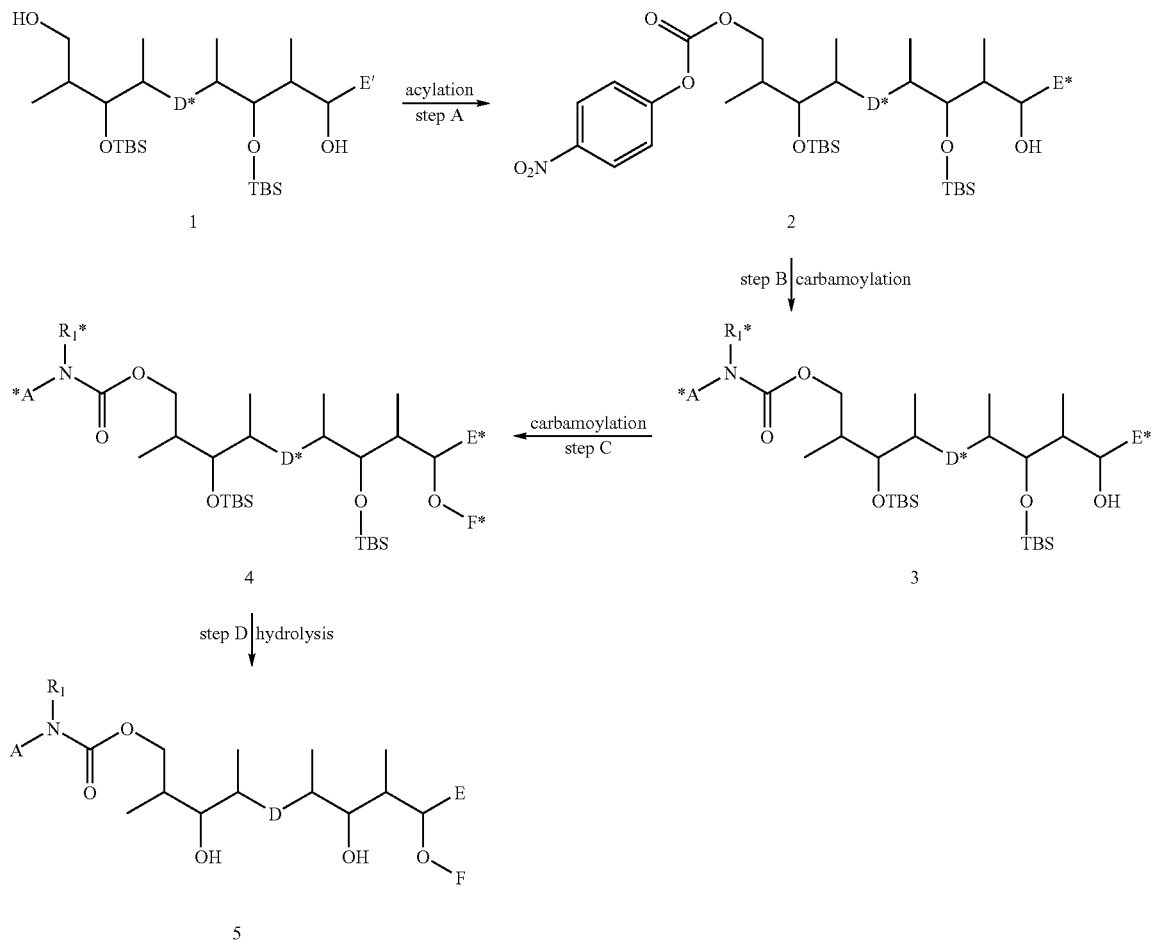

As to the individual steps in Scheme 3, Step A involves the acylation of an alcohol of formula 1 with an acylating compound, preferably a chloroformate such as 4-nitrophenyl chloroformate, to obtain a carbonate of formula 2. The acylation is conducted in the presence of: 1) a weak base, preferably an amine, more preferably triethylamine; 2) an acylation catalyst, preferably a pyridine such a 4-dimethylaminopyridine; and 3) a polar organic solvent, such as the presence of a Lewis acid such as Bu$_2$Sn(OAc)$_2$ or weak base such as triethylamine, in a polar aprotic solvent, preferably a halogenated solvent such as methylene chloride at a temperature of between −20° C. and 100° C., preferably between 0° C. and 50° C., for a period of between 5 minutes and 72 hours, preferably between 1 hour and 24 hours. In the case using Cl$_3$C(O)NCO, which produces substituted polyketides of formula I where F=H, the carbamoylation is conducted in the presence of a polar aprotic solvent, preferably a halogenated solvent such as methylene chloride at a temperature of between −20° C. and 100° C., preferably at 25° C., for a period of between 5 minutes and 72 hours, preferably between 1 hour and 8 hours; the work-up of this step is conducted in the presence of a protic organic solvent, preferably an alcohol such as methanol, in the presence of a base, for example, a carbonate such as potassium carbonate, at a temperature of between between 0° C. and 100° C., preferably at 25° C., for a period of between 5 minutes and 72 hours, preferably between 1 hour and 8 hours.

Step D concerns the hydrolysis of the bis(carbamate) of formula 4 to a substituted polyketide of formula 5. The hydrolysis reaction is conducted in the presence of: 1) a protic acid, preferably an aqueous protic acid solution, preferably an aqueous hydrogen halide solution, such as aqueous hydrogen chloride; and 2) a polar organic solvent, preferably a mixture of polar organic solvents, preferably a mixture of an aliphatic alcohol and an ether, such as methanol and tetrahydrofuran, at a temperature of between −20° C. and 40° C., preferably between 20° C. and 25° C., for a period of 8 hours and 7 days, preferably between 16 and 72 hours, more preferably between 24 and 48 hours.

$Cl_3C(O)NCO$ to give a bis(carbamate) of formula 3. In the case of using F*NCO, the carbamoylation is conducted in the presence of a Lewis acid such as $Bu_2Sn(OAc)_2$ or weak base such as triethylamine, in a polar aprotic solvent, preferably a halogenated solvent such as methylene chloride, at a temperature of between −20° C. and 100° C., preferably between 0° C. and 50° C., for a period of between 5 minutes and 72 hours, preferably between 1 hour and 24 hours. In the case using $Cl_3C(O)NCO$, which produces substituted polyketides of formula I where F=H, the carbamoylation is conducted in the presence of a polar aprotic solvent, preferably a halogenated solvent such as methylene chloride at a temperature of between −20° C. and 100° C., preferably at 25° C., for a period of between 5 minutes and 72 hours, preferably between 1 hour and 8 hours; the work-up of this step is conducted in the presence of a protic organic solvent, preferably an alcohol such as methanol, in the presence of a base, for example, a carbonate such as potassium carbonate, at a temperature of between between 0° C. and 100° C., preferably at 25° C., for a period of between 5 minutes and 72 hours, preferably between 1 hour and 8 hours.

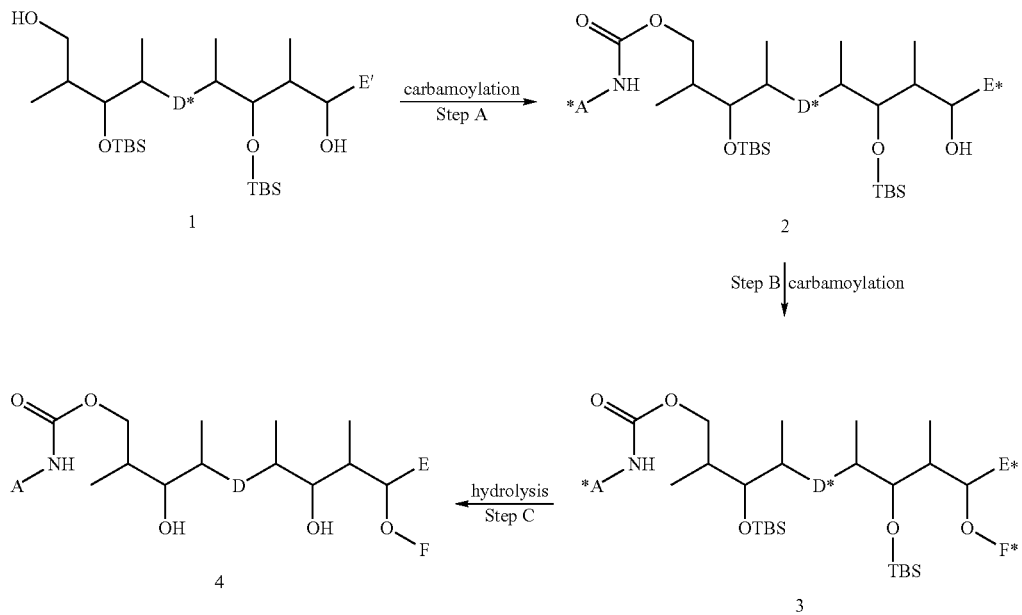

Scheme 4

As to the individual steps in Scheme 4, Step A involves the carbamoylation of the diol of formula 1, to obtain a carbamate compound of formula 2. The carbamoylation is conducted in the presence of: 1) an isocyanate of formula A*NCO, where A* is as described above; 2) a polar organic solvent, such as methylene chloride or ethyl acetate; and 3) a Lewis acid catalyst such as dibutyltin diacetate or a weak base such as triethylamine, at a temperature of between −78° C. and 60° C., preferably between 0° C. and 40° C., for a period of between 2 and 72 hours, preferably for 16 hours.

Step B concerns the carbamoylation of the carbamate of formula 2 with a an isocyanate either of formula F*NCO or Step C concerns the hydrolysis of the bis(carbamate) of formula 3 to a substituted polyketide of formula 4. The hydrolysis reaction is conducted in the presence of: 1) a protic acid, preferably an aqueous protic acid solution, preferably an aqueous hydrogen halide solution, such as aqueous hydrogen chloride; and 2) a polar organic solvent, preferably a mixture of polar organic solvents, preferably a mixture of an aliphatic alcohol and an ether, such as methanol and tetrahydrofuran, at a temperature of between −20° C. and 40° C., preferably between 20° C. and 25° C., for a period of 8 hours and 7 days, preferably between 16 and 72 hours, more preferably between 24 and 48 hours.

19

Scheme 5

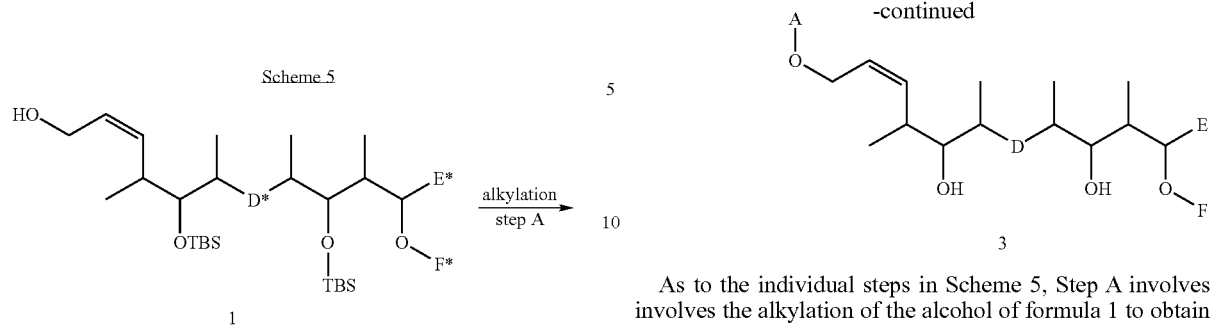

20

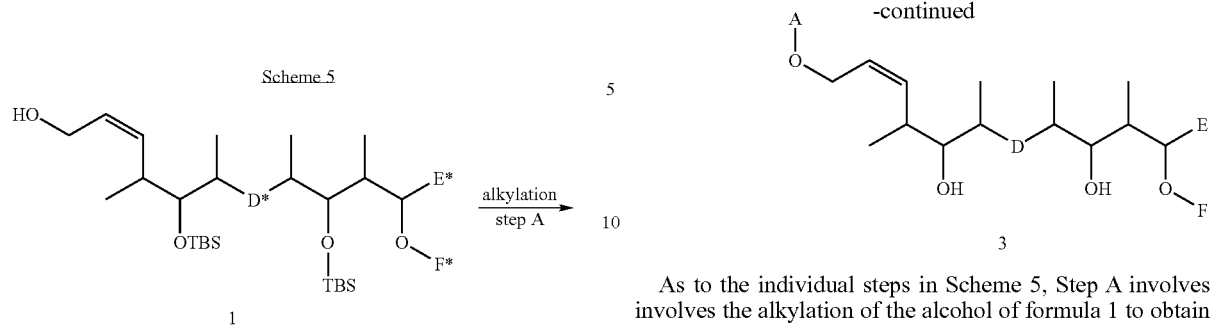

As to the individual steps in Scheme 5, Step A involves involves the alkylation of the alcohol of formula 1 to obtain an ether compound of formula 2. The alkylation is conducted in the presence of: 1) an alcohol of formula A*OH, where A* is as described above; 2) a coupling reagent such as diethyl azodicarboxylate; 3) a phosphine such as triphenylphosphine; and 4) a polar organic solvent, such as tetrahydrofuran, at a temperature of between −78° C. and 60° C., preferably between −20° C. and 40° C., for a period of between 2 and 72 hours, preferably for 16 hours.

Step B concerns the hydrolysis of an ether of formula 2 to a substituted polyketide of formula 3. The hydrolysis reaction is conducted in the presence of: 1) a protic acid, preferably an aqueous protic acid solution, preferably an aqueous hydrogen halide solution, such as aqueous hydrogen chloride; and 2) a polar organic solvent, preferably a mixture of polar organic solvents, preferably a mixture of an aliphatic alcohol and an ether, such as methanol and tetrahydrofuran, at a temperature of between −20° C. and 40° C., preferably between 20° C. and 25° C., for a period of 8 hours and 7 days, preferably between 16 and 72 hours, more preferably between 24 and 48 hours.

Scheme 6

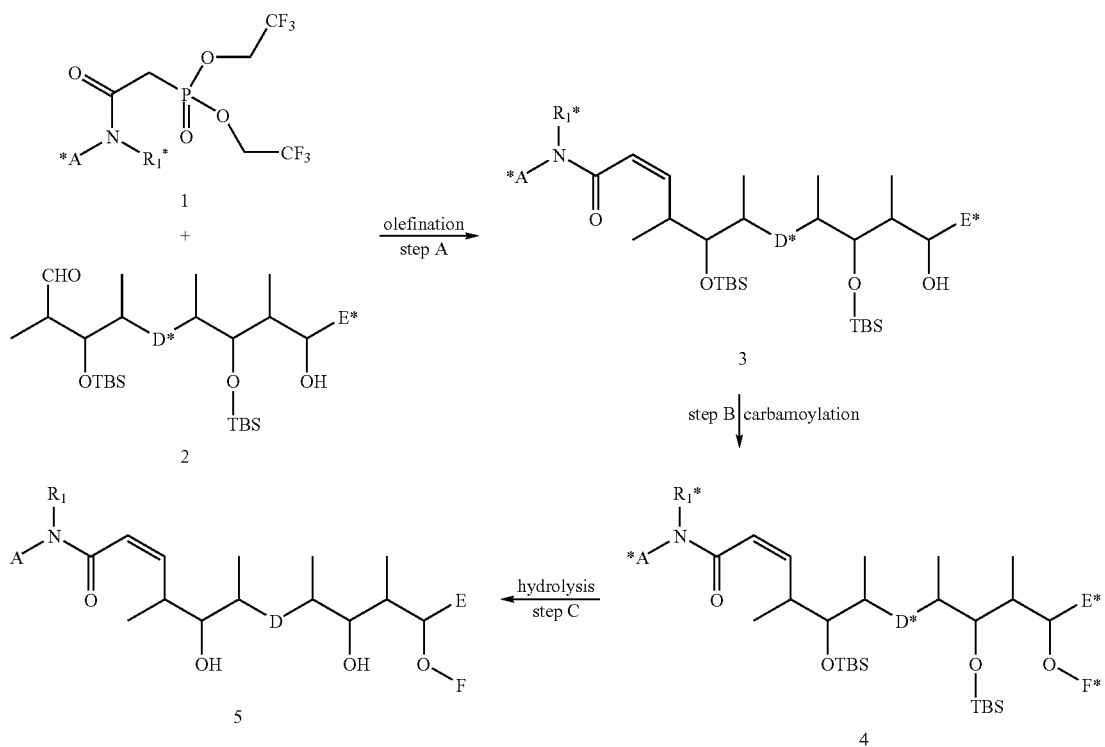

As to the individual steps in Scheme 6, Step A involves the olefination of an aldehyde of formula 2 with a phosphonate of formula 1 to obtain an olefin of formula 3. The olefination is conducted in the presence of: 1) a strong base, preferably a potassium salt such as potassium hexamethyldisilazide; 2) a crown ether such 18-crown-6; and 3) an inert organic solvent, preferably a hydrocarbon such as toluene, at a temperature of between −78° C. and 25° C., preferably at 0° C., for a period of between 10 minutes and 48 hours, preferably for 3 hours.

Step B concerns the carbamoylation of the olefin of formula 3 with a an isocyanate either of formula F*NCO or Cl₃C(O)NCO to give a carbamate of formula 4. In the case of using F*NCO, the carbamoylation is conducted in the presence of a Lewis acid such as Bu₂Sn(OAc)₂ or weak base such as triethylamine, in a polar aprotic solvent, preferably a halogenated solvent such as methylene chloride at a temperature of between −20° C. and 100° C., preferably between 0° C. and 50° C., for a period of between 5 minutes and 72 hours, preferably between 1 hour and 24 hours. In the case using Cl₃C(O)NCO, which produces substituted polyketides of formula I where F=H, the carbamoylation is conducted in the presence of a polar aprotic solvent, preferably a halogenated solvent such as methylene chloride at a temperature of between −20° C. and 100° C., preferably at 25° C., for a period of between 5 minutes and 72 hours, preferably between 1 hour and 8 hours; the work-up of this step is conducted in the presence of a protic organic solvent, preferably an alcohol such as methanol, in the presence of a base, for example, a carbonate such as potassium carbonate, at a temperature of between 0° C. and 100° C., preferably at 25° C., for a period of between 5 minutes and 72 hours, preferably between 1 hour and 8 hours.

Step C concerns the hydrolysis of the carbamate of formula 4 to a substituted polyketide of formula 5. The hydrolysis reaction is conducted in the presence of: 1) a protic acid, preferably an aqueous protic acid solution, preferably an aqueous hydrogen halide solution, such as aqueous hydrogen chloride; and 2) a polar organic solvent, preferably a mixture of polar organic solvents, preferably a mixture of an aliphatic alcohol and an ether, such as methanol and tetrahydrofuran, at a temperature of between −20° C. and 40° C., preferably between 20° C. and 25° C., for a period of 8 hours and 7 days, preferably between 16 and 72 hours, more preferably between 24 and 48 hours.

Scheme 7

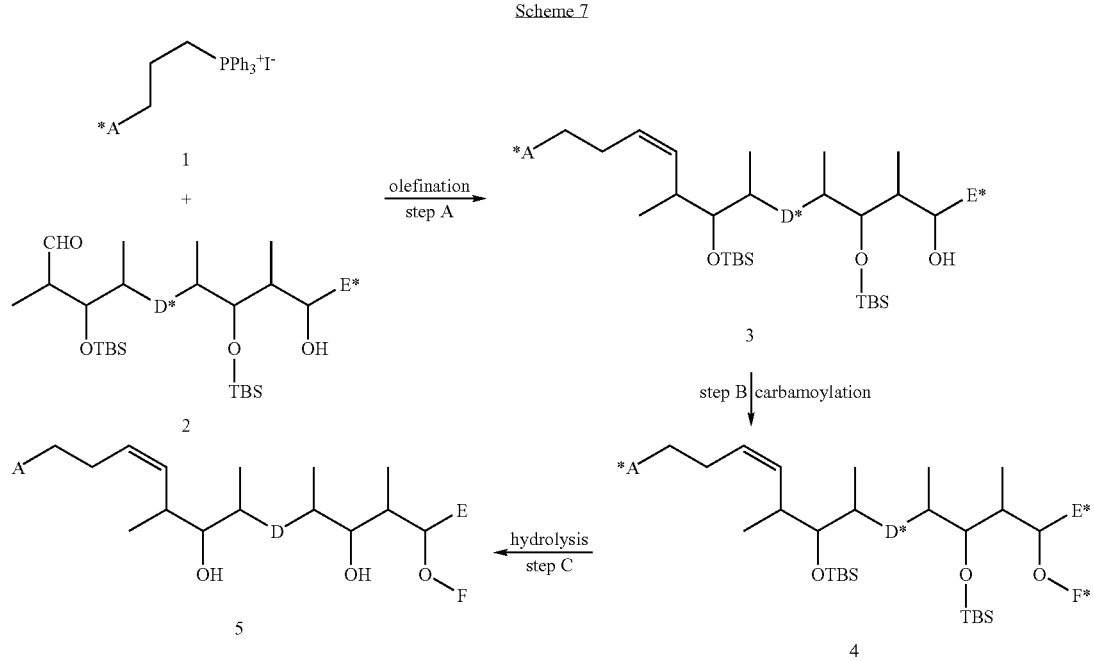

As to the individual steps in Scheme 7, Step A involves the olefination of an aldehyde of formula 2 with a phosphonium salt of formula 1 to obtain an olefin of formula 3. The olefination is conducted in the presence of: 1) a strong base, preferably an alkali metal salt such as potassium hexamethyldisilazide or butyllithium; and 2) an inert organic solvent, preferably a hydrocarbon such as toluene, or an ether such as tetrahydrofuran, at a temperature of between −78° C. and 25° C., preferably at 0° C., for a period of between 10 minutes and 48 hours, preferably for 3 hours.

Step B concerns the carbamoylation of the olefin of formula 3 with a an isocyanate either of formula F*NCO or Cl₃C(O)NCO to give a carbamate of formula 4. In the case of using F*NCO, the carbamoylation is conducted in the presence of a Lewis acid such as Bu₂Sn(OAc)₂ or weak base such as triethylamine, in a polar aprotic solvent, preferably a halogenated solvent such as methylene chloride at a temperature of between −20° C. and 100° C., preferably between 0° C. and 50° C., for a period of between 5 minutes and 72 hours, preferably between 1 hour and 24 hours. In the case using Cl₃C(O)NCO, which produces substituted polyketides of formula I where F=H, the carbamoylation is conducted in the presence of a polar aprotic solvent, preferably a halogenated solvent such as methylene chloride at a temperature of between −20° C. and 100° C., preferably at 25° C., for a period of between 5 minutes and 72 hours, preferably between 1 hour and 8 hours; the work-up of this step is conducted in the presence of a protic organic solvent, preferably an alcohol such as methanol, in the presence of a base, for example, a carbonate such as potassium carbonate, at a temperature of between between 0° C. and 100° C., preferably at 25° C., for a period of between 5 minutes and 72 hours, preferably between 1 hour and 8 hours.

Step C concerns the hydrolysis of the carbamate of formula 4 to a substituted polyketide of formula 5. The hydrolysis reaction is conducted in the presence of: 1) a protic acid, preferably an aqueous protic acid solution, preferably an aqueous hydrogen halide solution, such as aqueous hydrogen chloride; and 2) a polar organic solvent, preferably a mixture of polar organic solvents, preferably a mixture of an aliphatic alcohol and an ether, such as methanol and tetrahydrofuran, at a temperature of between −20° C. and 40° C., preferably between 20° C. and 25° C., for a period of 8 hours and 7 days, preferably between 16 and 72 hours, more preferably between 24 and 48 hours.

Scheme 8

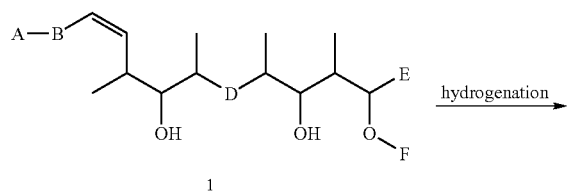

1

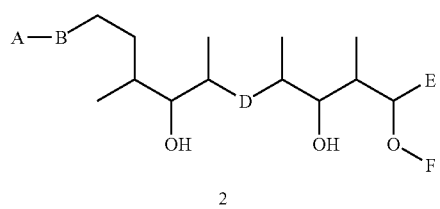

2

As to the individual step in Scheme 8, it involves the hydrogenation of a substituted polyketide of formula 1 to obtain a substituted polyketide of formula 2. The hydrogenation is conducted in the presence of: 1) hydrogen; 2) a transition metal catalyst such as palladium or platinum oxide; and 3) an organic solvent, preferably an alcohol such as methanol, or an ester such as ethyl acetate, at a temperature of between 0° C. and 35° C., preferably at 25° C., for a period of between 1 hour and 72 hours, preferably for 24 hours.

Scheme 9

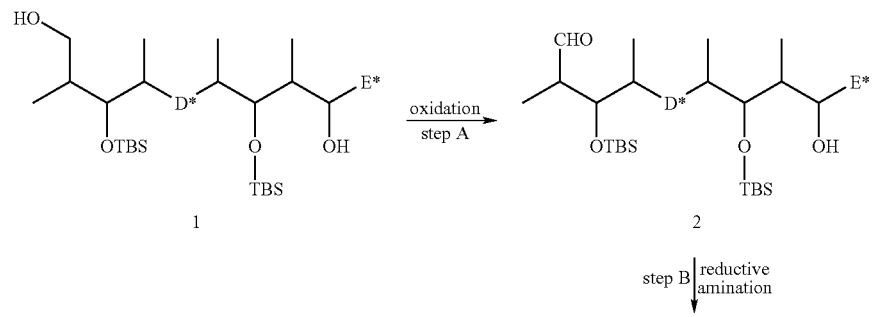

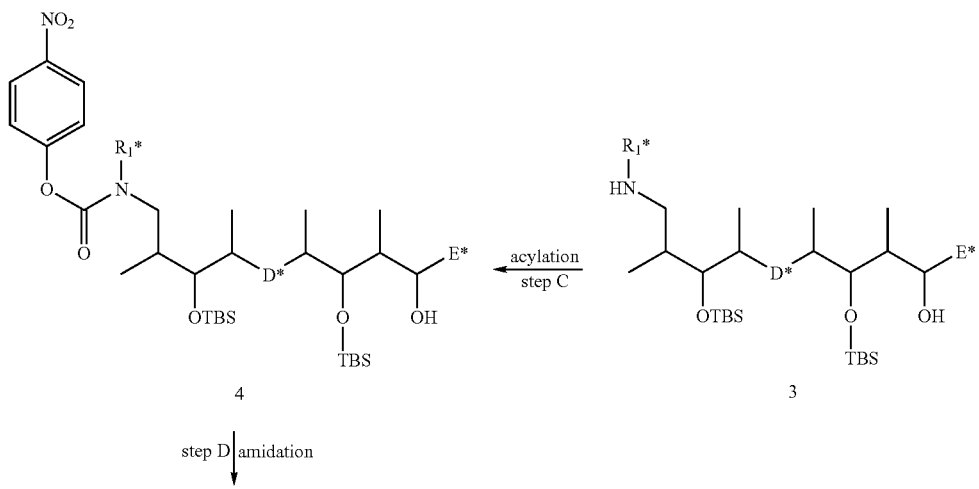

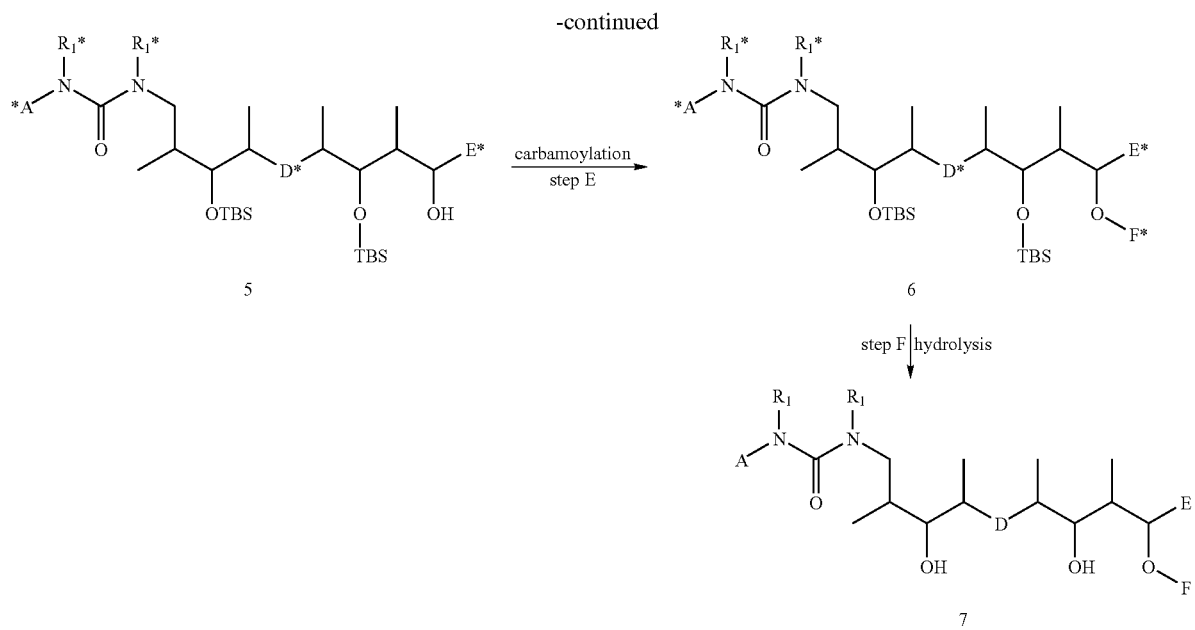

As to the individual steps in Scheme 9, Step A involves the oxidation of an alcohol of formula 1 to obtain an aldehyde of formula 2. The oxidation is conducted in the presence of: 1) an oxidizing reagent, preferably a mild oxidizing reagent such as the combinations of oxalyl chloride, DMSO and triethylamine; sulfur trioxide-pyridine complex, DMSO and triethylamine; and 2,2,6,6-tetramethyl-1-piperidinyloxy free radical and diacetoxyiodobenzene; and 2) an inert organic solvent, preferably a polar organic solvent such as methylene chloride, at a temperature of between −78° C. and 40° C., preferably from −20° C. to 25° C., for a period of between 10 minutes and 48 hours, preferably for 3 hours.

Step B involves the reductive amination of an aldehyde of formula 2 to obtain an amine of formula 3. The reductive amination is conducted in the presence of: 1) an amine of formula $R_1^*NH_2$ where $R_1^*$ is as defined above; 2) a reducing agent, preferably a hydride, more preferably a borohydride salt such as sodium borohydride; and 3) a polar organic solvent, preferably a protic organic solvent such as ethanol, at a temperature of between 0° C. and 40° C., preferably from 5° C. to 25° C., for a period of between 10 minutes and 48 hours, preferably for 16 hours.

Step C involves the acylation of an amine of formula 3 with an acylating compound, preferably a chloroformate such as 4-nitrophenyl chloroformate, to obtain a carbonate of formula 4. The acylation is conducted in the presence of: 1) a weak base, preferably an amine, more preferably triethylamine; 2) an acylation catalyst, preferably a pyridine such a 4-dimethylaminopyridine; and 3) a polar organic solvent, such as methylene chloride or ethyl acetate, at a temperature of between −10° C. and 50° C., preferably between −5° C. and 20° C., for a period of between 10 minutes and 24 hours, preferably for 2 hours.

Step D concerns the amidation of the carbamate of formula 4, to obtain a urea compound of formula 5. The carbamoylation is conducted in the presence of: 1) an amine of formula $A^*NHR_1^*$, where $A^*$ and $R_1^*$ are as defined above; and 2) a polar organic solvent, such as methylene chloride or ethyl acetate, at a temperature of between −78° C. and 50° C., preferably between −20° C. and 25° C., for a period of between 2 and 72 hours, preferably for 16 hours.

Step E concerns the carbamoylation of the urea of formula 5 with a an isocyanate either of formula F*NCO or $Cl_3C(O)NCO$ to give a carbamate of formula 6. In the case of using F*NCO, the carbamoylation is conducted in the presence of a Lewis acid such as $Bu_2Sn(OAc)_2$ or weak base such as triethylamine, in a polar aprotic solvent, preferably a halogenated solvent such as methylene chloride at a temperature of between −20° C. and 100° C., preferably between 0° C. and 50° C., for a period of between 5 minutes and 72 hours, preferably between 1 hour and 24 hours. In the case using $Cl_3C(O)NCO$, which produces substituted polyketides of formula I where F=H, the carbamoylation is conducted in the presence of a polar aprotic solvent, preferably a halogenated solvent such as methylene chloride, at a temperature of between −20° C. and 100° C., preferably at 25° C., for a period of between 5 minutes and 72 hours, preferably between 1 hour and 8 hours; the work-up of this step is conducted in the presence of a protic organic solvent, preferably an alcohol such as methanol, in the presence of a base, for example, a carbonate such as potassium carbonate, at a temperature of between between 0° C. and 100° C., preferably at 25° C., for a period of between 5 minutes and 72 hours, preferably between 1 hour and 8 hours.

Step F concerns the hydrolysis of carbamate of formula 6 to a substituted polyketide of formula 7. The hydrolysis reaction is conducted in the presence of: 1) a protic acid, preferably an aqueous protic acid solution, preferably an aqueous hydrogen halide solution, such as aqueous hydrogen chloride; and 2) a polar organic solvent, preferably a mixture of polar organic solvents, preferably a mixture of an aliphatic alcohol and an ether, such as methanol and tetrahydrofuran, at a temperature of between −20° C. and 40° C., preferably between 20° C. and 25° C., for a period of 8 hours and 7 days, preferably between 16 and 72 hours, more preferably between 24 and 48 hours.

Scheme 10

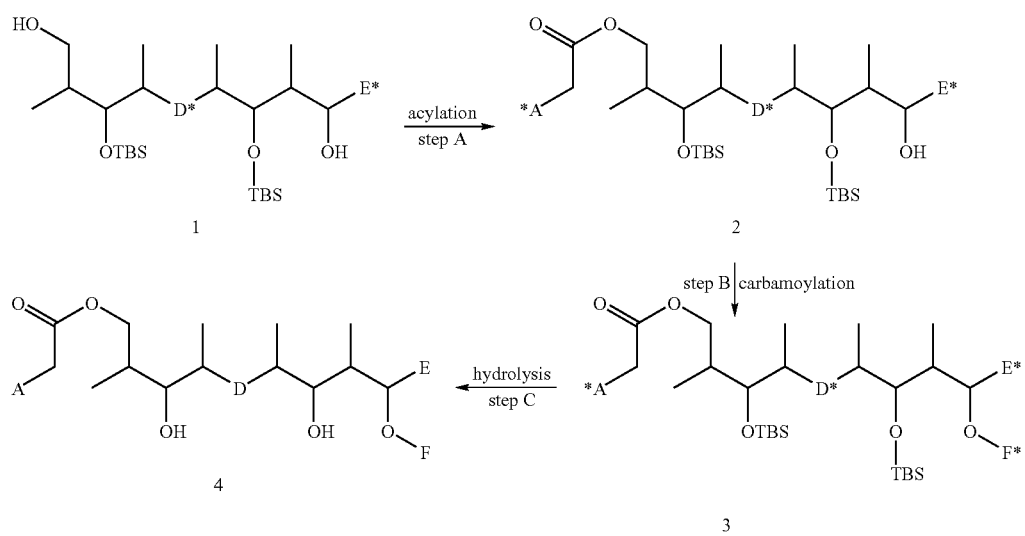

As to the individual steps in Scheme 10, Step A involves the acylation of an alcohol of formula 1 to obtain an ester of formula 2. The acylation is conducted in the presence of: 1) a carboxylic acid of formula A*CH$_2$CO$_2$H where A* is as defined above; 2) a carboxylic acid coupling reagent, preferably a diimide such as 1-(3-dimethylaminopropyl)-3-ethylcarbodiimide hydrochloride, and a suitable activating agent common to diimide coupling reactions, preferably a substituted pyridine such a 4-dimethylaminopyridine; and 3) an inert organic solvent, preferably a chlorinated alkane such as methylene chloride, at a temperature of between −78° C. and 25° C. for a period of between 1 and 24 hours.

Step B concerns the carbamoylation of the ester of formula 2 with a an isocyanate either of formula F*NCO or Cl$_3$C(O)NCO to give a carbamate of formula 3. In the case of using F*NCO, the carbamoylation is conducted in the presence of a Lewis acid such as Bu$_2$Sn(OAc)$_2$ or weak base such as triethylamine, in a polar aprotic solvent, preferably a halogenated solvent such as methylene chloride at a temperature of between −20° C. and 100° C., preferably between 0° C. and 50° C., for a period of between 5 minutes and 72 hours, preferably between 1 hour and 24 hours. In the case using Cl$_3$C(O)NCO, which produces substituted polyketides of formula I where F=H, the carbamoylation is conducted in the presence of a polar aprotic solvent, preferably a halogenated solvent such as methylene chloride at a temperature of between −20° C. and 100° C., preferably at 25° C., for a period of between 5 minutes and 72 hours, preferably between 1 hour and 8 hours; the work-up of this step is conducted in the presence of a protic organic solvent, preferably an alcohol such as methanol, in the presence of a base, for example, a carbonate such as potassium carbonate, at a temperature of between between 0° C. and 100° C., preferably at 25° C., for a period of between 5 minutes and 72 hours, preferably between 1 hour and 8 hours.

Step C concerns the hydrolysis of carbamate of formula 3 to a substituted polyketide of formula 4. The hydrolysis reaction is conducted in the presence of: 1) a protic acid, preferably an aqueous protic acid solution, preferably an aqueous hydrogen halide solution, such as aqueous hydrogen chloride; and 2) a polar organic solvent, preferably a mixture of polar organic solvents, preferably a mixture of an aliphatic alcohol and an ether, such as methanol and tetrahydrofuran, at a temperature of between −20° C. and 40° C., preferably between 20° C. and 25° C., for a period of 8 hours and 7 days, preferably between 16 and 72 hours, more preferably between 24 and 48 hours

Scheme 11

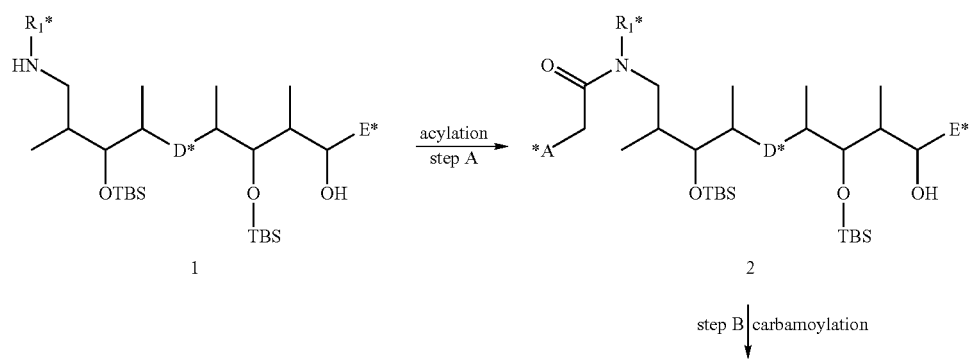

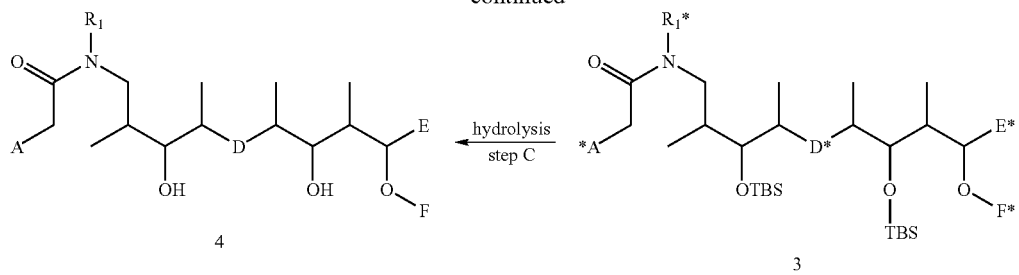

As to the individual steps in Scheme 11, Step A involves the acylation of an amine of formula 1 to obtain an amide of formula 2. The acylation is conducted in the presence of: 1) a carboxylic acid of formula A*CH$_2$CO$_2$H where A* is as defined above; 2) a carboxylic acid coupling reagent, preferably a diimide such as 1-(3-dimethylaminopropyl)-3-ethylcarbodiimide hydrochloride, and a suitable activating agent common to diimide coupling reactions, such as 1-hydroxybenzotriazole; and 3) a polar organic solvent, preferably a low molecular weight amide such as DMF, at a temperature of between 0° C. and 40° C., preferably at 25° C., for a period of between 1 and 24 hours.

Step B concerns the carbamoylation of the amide of formula 2 with a an isocyanate either of formula F*NCO or Cl$_3$C(O)NCO to give a carbamate of formula 3. In the case of using F*NCO, the carbamoylation is conducted in the presence of a Lewis acid such as Bu$_2$Sn(OAc)$_2$ or weak base such as triethylamine, in a polar aprotic solvent, preferably a halogenated solvent such as methylene chloride at a temperature of between −20° C. and 100° C., preferably between 0° C. and 50° C., for a period of between 5 minutes erably a halogenated solvent such as methylene chloride, at a temperature of between −20° C. and 100° C., preferably at 25° C., for a period of between 5 minutes and 72 hours, preferably between 1 hour and 8 hours; the work-up of this step is conducted in the presence of a protic organic solvent, preferably an alcohol such as methanol, in the presence of a base, for example, a carbonate such as potassium carbonate, at a temperature of between between 0° C. and 100° C., preferably at 25° C., for a period of between 5 minutes and 72 hours, preferably between 1 hour and 8 hours.

Step C concerns the hydrolysis of the carbamate of formula 3 to a substituted polyketide of formula 4. The hydrolysis reaction is conducted in the presence of: 1) a protic acid, preferably an aqueous protic acid solution, preferably an aqueous hydrogen halide solution, such as aqueous hydrogen chloride; and 2) a polar organic solvent, preferably a mixture of polar organic solvents, preferably a mixture of an aliphatic alcohol and an ether, such as methanol and tetrahydrofuran, at a temperature of between −20° C. and 40° C., preferably between 20° C. and 25° C., for a period of 8 hours and 7 days, preferably between 16 and 72 hours, more preferably between 24 and 48 hours.

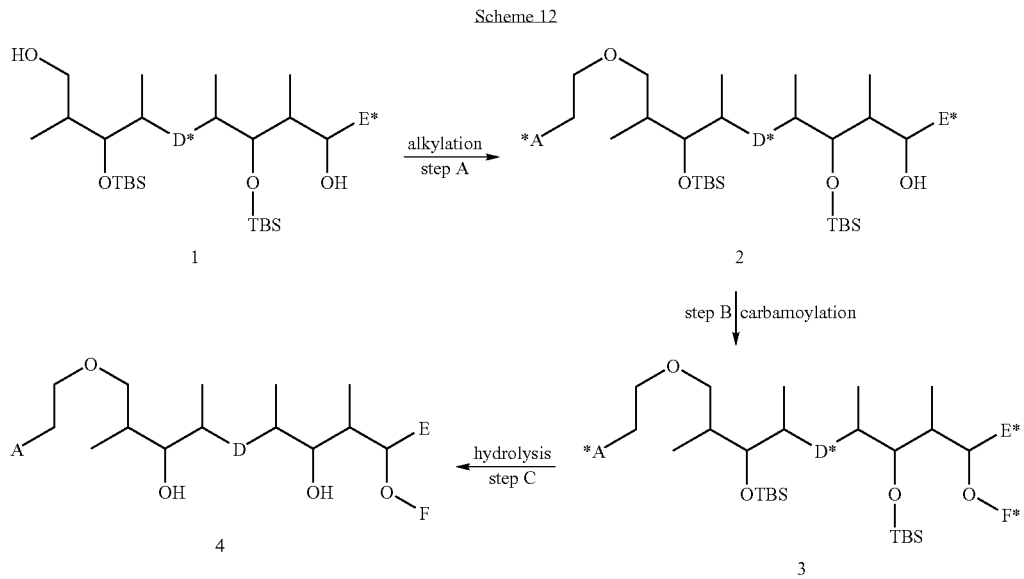

Scheme 12 and 72 hours, preferably between 1 hour and 24 hours. In the case using Cl$_3$C(O)NCO, which produces substituted polyketides of formula I where F=H, the carbamoylation is conducted in the presence of a polar aprotic solvent, pref- As to the individual steps in Scheme 12, Step A involves the alkylation of an alcohol of formula 1 to obtain an ether of formula 2. The alkylation is conducted in the presence of: 1) an alkyl iodide of formula A*CH$_2$CH$_2$I where A* is as defined above; 2) a strong base, such as sodium hydride, LDA or silver oxide; and 3) a polar organic solvent, such as DMF or tetrahrdrofuran, at a temperature of between −78° C. and 40° C., preferably from −20° C. to 25° C., for a period of between 1 and 24 hours.

mixture of an aliphatic alcohol and an ether, such as methanol and tetrahydrofuran, at a temperature of between −20° C. and 40° C., preferably between 20° C. and 25° C., for a period of 8 hours and 7 days, preferably between 16 and 72 hours, more preferably between 24 and 48 hours.

Scheme 13

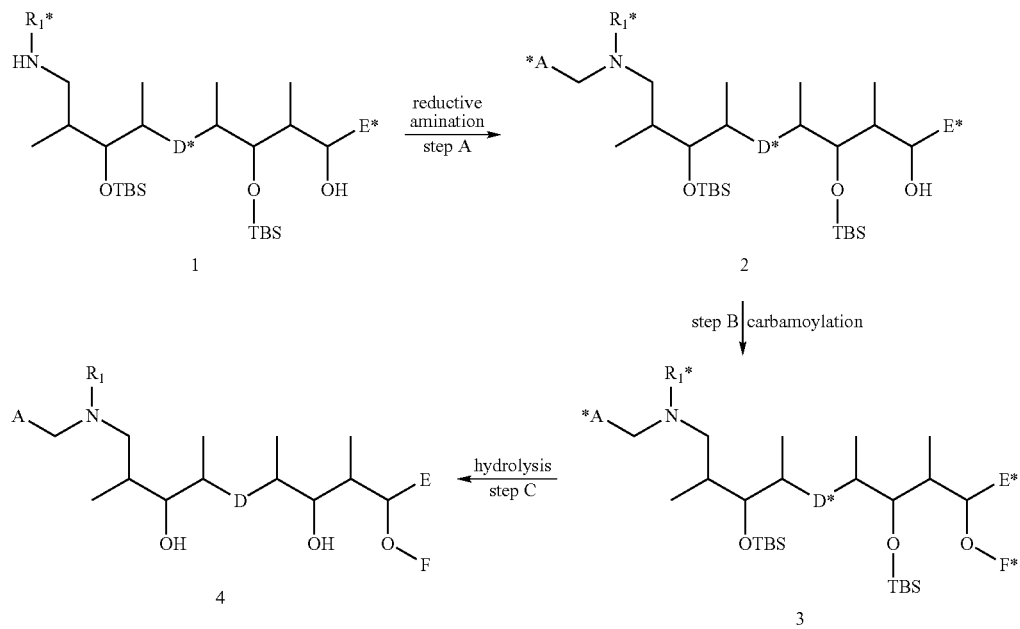

As to the individual steps in Scheme 13, Step A involves the reductive amination with an amine of formula 1 to obtain an amine of formula 2. The reductive amination is conducted in the presence of: 1) an aldehyde of formula A*CHO where A* is as defined above; 2) a reducing agent, preferably a hydride, more preferably a borohydride salt such as sodium borohydride; and 3) a polar organic solvent, preferably a protic organic solvent such as ethanol, at a temperature of between 0° C. and 40° C., preferably from 5° C. to 25° C., for a period of between 10 minutes and 48 hours, preferably for 16 hours.

Step B concerns the carbamoylation of the amine of formula 2 with a an isocyanate either of formula F*NCO or Cl$_3$C(O)NCO to give a carbamate of formula 3. In the case of using F*NCO, the carbamoylation is conducted in the presence of a Lewis acid such as Bu$_2$Sn(OAc)$_2$ or weak base such as triethylamine, in a polar aprotic solvent, preferably a halogenated solvent such as methylene chloride, at a temperature of between −20° C. and 100° C., preferably between 0° C. and 50° C., for a period of between 5 minutes and 72 hours, preferably between 1 hour and 24 hours. In the case using Cl$_3$C(O)NCO, which produces substituted polyketides of formula I where F=H, the carbamoylation is conducted in the presence of a polar aprotic solvent, preferably a halogenated solvent such as methylene chloride at a temperature of between −20° C. and 100° C., preferably at 25° C., for a period of between 5 minutes and 72 hours, preferably between 1 hour and 8 hours; the work-up of this step is conducted in the presence of a protic organic solvent, preferably an alcohol such as methanol, in the presence of a base, for example, a carbonate such as potassium carbonate, at a temperature of between between 0° C. and 100° C., Step B concerns the carbamoylation of the ether of formula 2 with a an isocyanate either of formula F*NCO or Cl$_3$C(O)NCO to give a carbamate of formula 3. In the case of using F*NCO, the carbamoylation is conducted in the presence of a Lewis acid such as Bu$_2$Sn(OAc)$_2$ or weak base such as triethylamine, in a polar aprotic solvent, preferably a halogenated solvent such as methylene chloride, at a temperature of between −20° C. and 100° C., preferably between 0° C. and 50° C., for a period of between 5 minutes and 72 hours, preferably between 1 hour and 24 hours. In the case using Cl$_3$C(O)NCO, which produces substituted polyketides of formula I where F=H, the carbamoylation is conducted in the presence of a polar aprotic solvent, preferably a halogenated solvent such as methylene chloride at a temperature of between −20° C. and 100° C., preferably at 25° C., for a period of between 5 minutes and 72 hours, preferably between 1 hour and 8 hours; the work-up of this step is conducted in the presence of a protic organic solvent, preferably an alcohol such as methanol, in the presence of a base, for example, a carbonate such as potassium carbonate, at a temperature of between between 0° C. and 100° C., preferably at 25° C., for a period of between 5 minutes and 72 hours, preferably between 1 hour and 8 hours.

Step C concerns the hydrolysis of the carbamate of formula 3 to a substituted polyketide of formula 4. The hydrolysis reaction is conducted in the presence of: 1) a protic acid, preferably an aqueous protic acid solution, preferably an aqueous hydrogen halide solution, such as aqueous hydrogen chloride; 2) a polar organic solvent, preferably a mixture of polar organic solvents, preferably a preferably at 25° C., for a period of between 5 minutes and 72 hours, preferably between 1 hour and 8 hours.

Step C concerns the hydrolysis of the carbamate of formula 3 to a substituted polyketide of formula 4. The hydrolysis reaction is conducted in the presence of: 1) a protic acid, preferably an aqueous protic acid solution, preferably an aqueous hydrogen halide solution, such as aqueous hydrogen chloride; and 2) a polar organic solvent, preferably a mixture of polar organic solvents, preferably a mixture of an aliphatic alcohol and an ether, such as methanol and tetrahydrofuran, at a temperature of between −20° C. and 40° C., preferably between 20° C. and 25° C., for a period of 8 hours and 7 days, preferably between 16 and 72 hours, more preferably between 24 and 48 hours.

conducted in the presence of: 1) an amine of formula $A*CH_2CH_2NHR_1*$ where $A*$ and $R_1*$ are as defined above; 2) a carboxylic acid coupling reagent, preferably a diimide such as 1-(3-dimethylaminopropyl)-3-ethylcarbodiimide hydrochloride, and a suitable activating agent common to diimide coupling reactions, such as 1-hydroxybenzotriazole; and 3) a polar organic solvent, preferably a low molecular weight amide such as DMF, at a temperature of between 0° C. and 40° C., preferably at 25° C., for a period of between 1 and 24 hours.

Step C concerns the carbamoylation of the amide of formula 3 with a an isocyanate either of formula F*NCO or $Cl_3C(O)NCO$ to give a carbamate of formula 4. In the case of using F*NCO, the carbamoylation is conducted in the

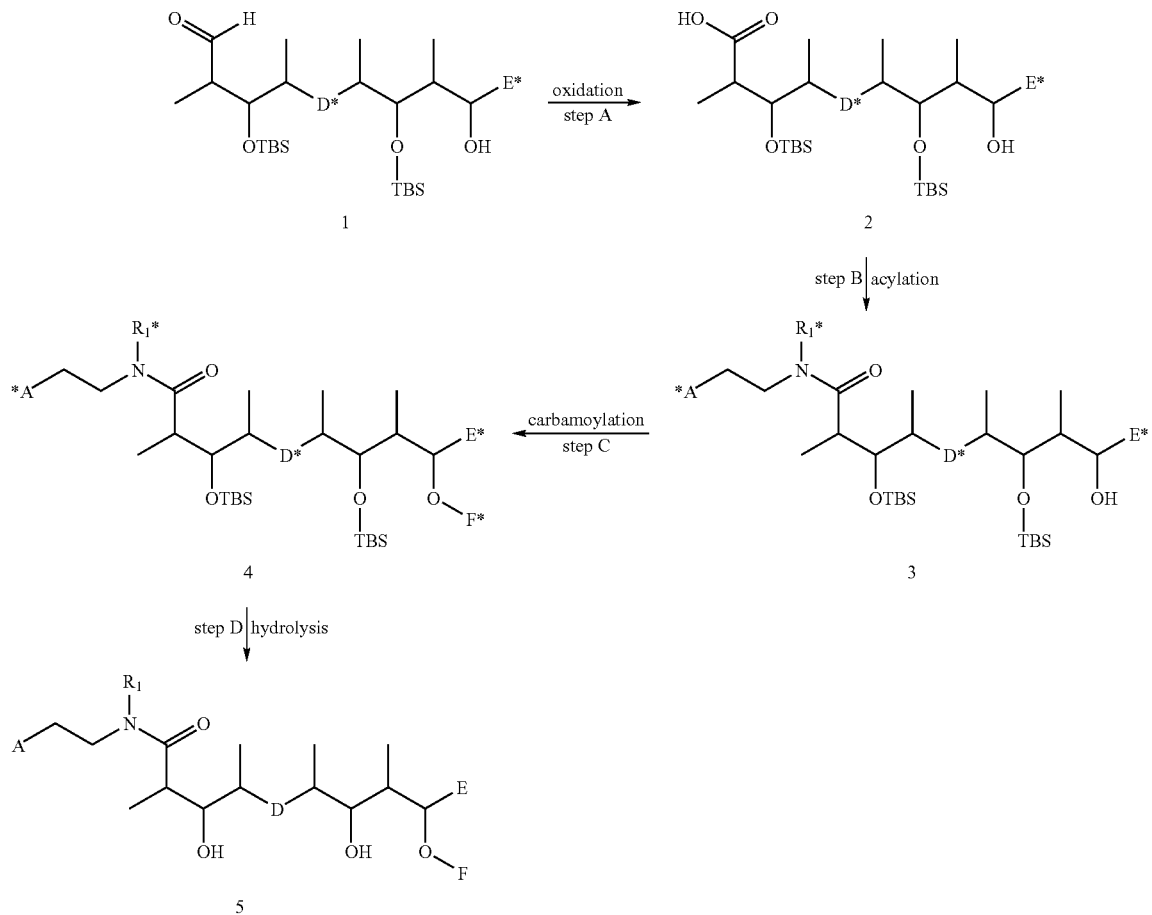

As to the individual steps in Scheme 14, Step A involves the oxidation an aldehyde of formula 1 to obtain a carboxylic acid of formula 2. The oxidation is conducted in the presence of: 1) an oxidizing agent such as sodium chlorite; 2) a phosphate salt, preferably sodium dihydrogenphosphate; 3) a protic organic solvent, preferably an alcohol such as t-butanol; and 4) an alkene, preferably 2-methylpropene, at a temperature of between 0° C. and 40° C., preferably at 25° C., for a period of between 10 minutes and 8 hours, preferably for 1 hour.

Step B involves the acylation of a carboxylic acid of formula 2 to obtain an amide of formula 3. The acylation is presence of a Lewis acid such as $Bu_2Sn(OAc)_2$ or weak base such as triethylamine, in a polar aprotic solvent, preferably a halogenated solvent such as methylene chloride at a temperature of between −20° C. and 100° C., preferably between 0° C. and 50° C., for a period of between 5 minutes and 72 hours, preferably between 1 hour and 24 hours. In the case using $Cl_3C(O)NCO$, which produces substituted polyketides of formula I where F=H, the carbamoylation is conducted in the presence of a polar aprotic solvent, preferably a halogenated solvent such as methylene chloride, at a temperature of between −20° C. and 100° C., preferably between 25° C., for a period of between 5 minutes and 72 hours, preferably between 1 hour and 8 hours; the work-up of this step is conducted in the presence of a protic organic solvent, preferably an alcohol such as methanol, in the presence of a base, for example, a carbonate such as potassium carbonate, at a temperature of between between 0° C. and 100° C., preferably at 25° C., for a period of between 5 minutes and 72 hours, preferably between 1 hour and 8 hours.

Step D concerns the hydrolysis of a carbamate of formula 4 to a substituted polyketide of formula 5. The hydrolysis reaction is conducted in the presence of: 1) a protic acid, preferably an aqueous protic acid solution, preferably an aqueous hydrogen halide solution, such as aqueous hydrogen chloride; and 2) a polar organic solvent, preferably a mixture of polar organic solvents, preferably a mixture of an aliphatic alcohol and an ether, such as methanol and tetrahydrofuran, at a temperature of between −20° C. and 40° C., preferably between 20° C. and 25° C., for a period of 8 hours and 7 days, preferably between 16 and 72 hours, more preferably between 24 and 48 hours.

of formula 3. The palladium-mediated coupling is conducted in the presence of: 1) a hindered organometallic reagent, preferably a hindered organolithium reagent such as t-butyllithium; 2) either a zinc halide such as zinc chloride or a hindered boron reagent such as 9-methoxy-9-borabicyclo[3.3.1]nonane; 3) a palladium reagent such as tetrakis(triphenylphosphine)palladium(0) or [1,1'-bis(diphenylphosphino)ferrocene]-dichloropalladium(II); and 4) a polar organic solvent, preferably an ether such as diethyl ether, at a temperature of between −78° C. and 25° C., for a period of between 1 hour and 72 hours.

Step B involves the oxidative hydrolysis of an alkene of formula 3 to a diol of formula 4. The oxidative hydrolysis is conducted in the presence of 1) an oxidant, preferably a quinone such as 2,3-dichloro-5,6-dicyano-1,4-benzoquinone; 2) water; and 3) a polar organic solvent, preferably a halogenated hydrocarbon such as methylene chloride, at a temperature of between −20° C. and 40° C., preferably at 25° C., for a period of between 1 hour and 72 hours, preferably for 1 hour.

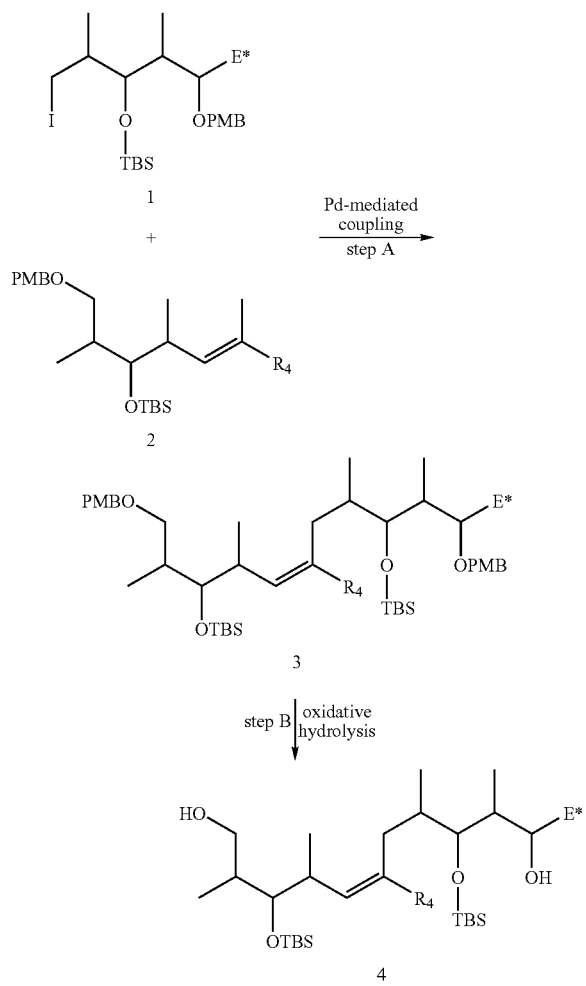

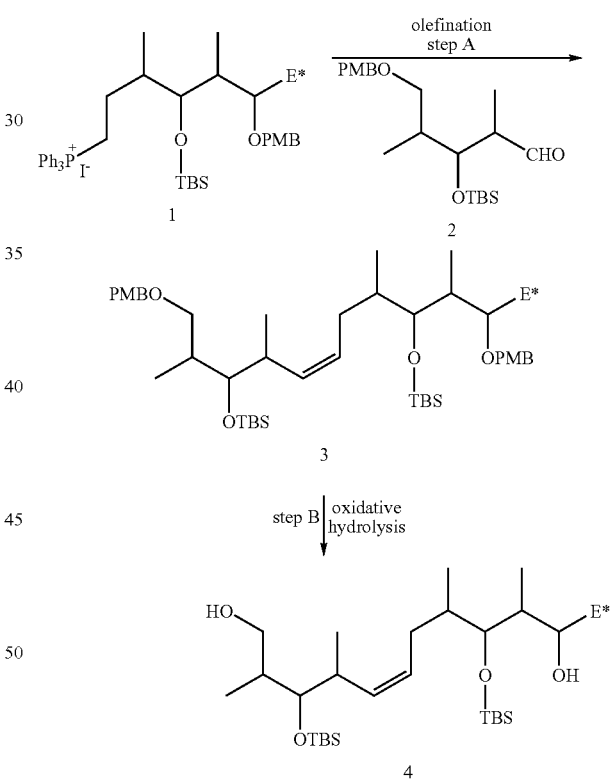

As to the individual steps in Scheme 15, Step A involves the palladium-mediated coupling of an alkyl iodide of formula 1 and a vinyl iodide of formula 2 to obtain an alkene As to the individual steps in Scheme 16, Step A involves the olefination of an aldehyde of formula 2 with a phosphonium salt of formula 1 to obtain an alkene of formula 3. The olefination is conducted in the presence of: 1) a strong base, preferably an alkali metal salt such as potassium hexamethyldisilazide or butyllithium; and 2) an inert organic solvent, preferably a hydrocarbon such as toluene, or an ether such as tetrahydrofuran, at a temperature of between −78° C. and 25° C., preferably at 0° C., for a period of between 10 minutes and 48 hours, preferably for 3 hours.

Step B involves the oxidative hydrolysis of an alkene of formula 3 to a diol of formula 4. The oxidative hydrolysis is conducted in the presence of 1) an oxidant, preferably a quinone such as 2,3-dichloro-5,6-dicyano-1,4-benzoquinone; 2) water; and 3) a polar organic solvent, preferably a halogenated hydrocarbon such as methylene chloride, at a temperature of between −20° C. and 40° C., preferably at 25° C., for a period of between 1 hour and 72 hours, preferably for 1 hour.

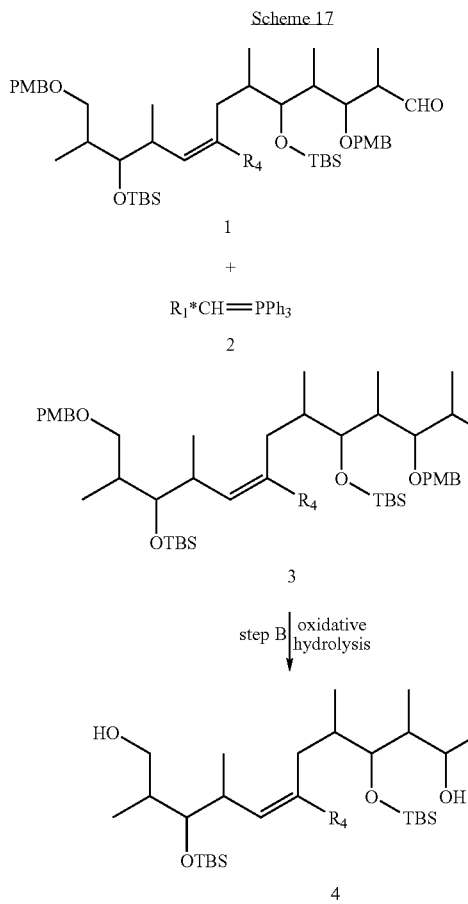

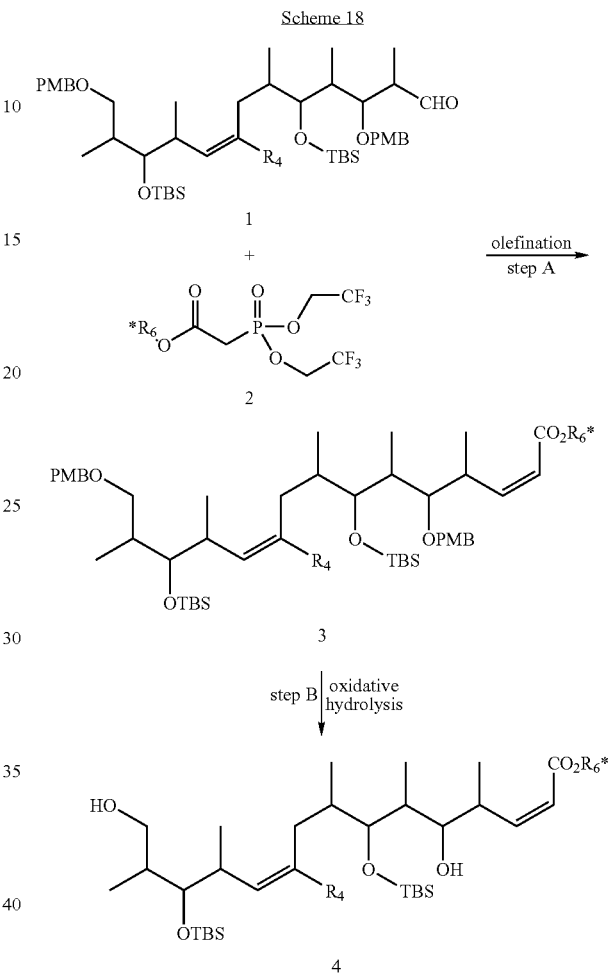

As to the individual steps in Scheme 17, Step A involves the olefination of an aldehyde of formula 1 with a phosphonium salt of formula 2 to obtain an alkene of formula 3. The olefination is conducted in the presence of: 1) a strong base, preferably an alkali metal salt such as potassium hexamethyldisilazide or butyllithium; and 2) an inert organic solvent, preferably a hydrocarbon such as toluene, or an ether such as tetrahydrofuran, at a temperature of between −78° C. and 25° C., preferably at 0° C., for a period of between 10 minutes and 48 hours, preferably for 3 hours.

Step B involves the oxidative hydrolysis of an alkene of formula 3 to a diol of formula 4. The oxidative hydrolysis is conducted in the presence of 1) an oxidant, preferably a quinone such as 2,3-dichloro-5,6-dicyano-1,4-benzoquinone; 2) water; and 3) a polar organic solvent, preferably a halogenated hydrocarbon such as methylene chloride, at a temperature of between −20° C. and 40° C., preferably at 25° C., for a period of between 1 hour and 72 hours, preferably for 1 hour.

As to the individual steps in Scheme 18, Step A involves the olefination of an aldehyde of formula 1 with a phosphonate of formula 2 to obtain an olefin of formula 3. The olefination is conducted in the presence of: 1) a strong base, preferably a potassium salt such as potassium hexamethyldisilazide; 2) a crown ether such 18-crown-6; and 3) an inert organic solvent, preferably a hydrocarbon such as toluene, at a temperature of between −78° C. and 25° C., preferably at 0° C., for a period of between 10 minutes and 48 hours, preferably for 3 hours.

Step B involves the oxidative hydrolysis of an alkene of formula 3 to a diol of formula 4. The oxidative hydrolysis is conducted in the presence of: 1) an oxidant, preferably a quinone such as 2,3-dichloro-5,6-dicyano-1,4-benzoquinone; 2) water; and 3) a polar organic solvent, preferably a halogenated hydrocarbon such as methylene chloride, at a temperature of between −20° C. and 40° C., preferably at 25° C., for a period of between 1 hour and 72 hours, preferably for 1 hour.

Scheme 19

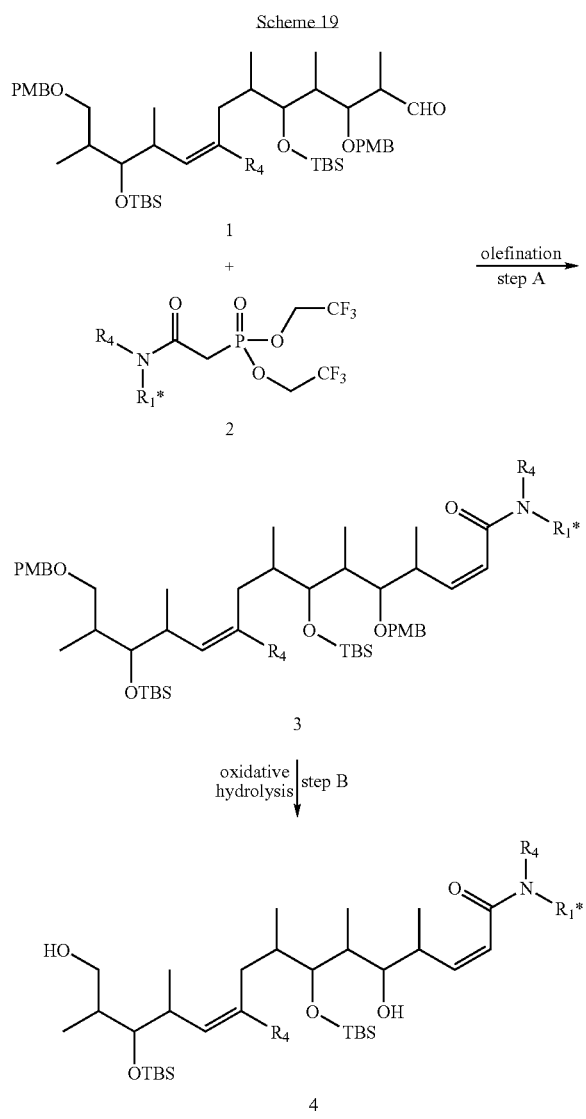

Scheme 20

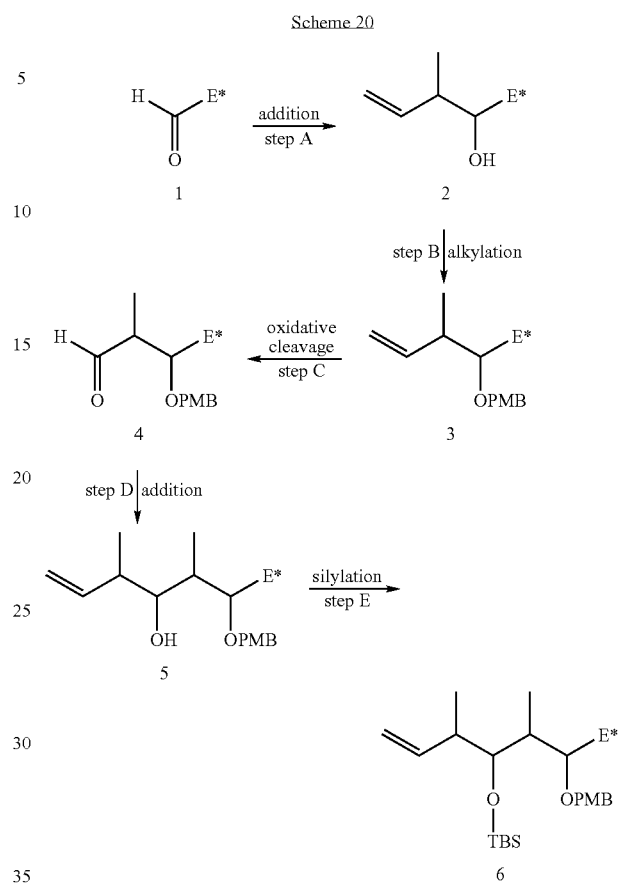

As to the individual steps in Scheme 19, Step A involves the olefination of an aldehyde of formula 1 with a phosphonate of formula 2 to obtain an olefin of formula 3. The olefination is conducted in the presence of: 1) a strong base, preferably a potassium salt such as potassium hexamethyldisilazide; 2) a crown ether such 18-crown-6; and 3) an inert organic solvent, preferably a hydrocarbon such as toluene, at a temperature of between −78° C. and 25° C., preferably at 0° C., for a period of between 10 minutes and 48 hours, preferably for 3 hours.

Step B involves the oxidative hydrolysis of an alkene of formula 3 to a diol of formula 4. The oxidative hydrolysis is conducted in the presence of: 1) an oxidant, preferably a quinone such as 2,3-dichloro-5,6-dicyano-1,4-benzoquinone; 2) water; and 3) a polar organic solvent, preferably a halogenated hydrocarbon such as methylene chloride, at a temperature of between −20° C. and 40° C., preferably at 25° C., for a period of between 1 hour and 72 hours, preferably for 1 hour.

The syntheses described in Scheme 20 may be applied when E* is not —CH($R_7$)CH=CH—CH=CH$_2$ or —CH($R_7$)CH=CH$_2$. As to the individual steps in Scheme 20, Step A involves the addition of a butene group to an aldehyde of formula 1 to obtain an alcohol of formula 2.

The addition is conducted in the presence of: 1) a crotylboron reagent, preferably a chiral crotylboron reagent, more preferably a Z-crotylboronate derived from diisopropyl tartrate; 2) an optional drying reagent such as molecular sieves; and 3) an inert organic solvent, preferably a hydrocarbon such as toluene, at a temperature of between −100° C. and 5° C., preferably at −78° C., for a period of between 10 minutes and 48 hours, preferably for 3 hours.

Step B involves the alkylation of an alcohol of formula 2 to obtain an alcohol of formula 3. The alkylation is conducted in the presence of: 1) a reactive benzylating reagent, preferably a reactive para-methoxybenzylating reagent such as p-methoxybenzyl-2,2,2-trichloroacetimidate; 2) a proton source, preferably a sulfonic acid such as pyridinium p-toluenesulfonate; and 3) a polar organic solvent, preferably a halogenated hydrocarbon such as methylene chloride, at a temperature of between −78° C. and 25° C., preferably at 0° C., for a period of between 10 minutes and 48 hours, preferably for 3 hours.

Step C involves the two stage oxidative cleavage of an alcohol of formula 3 to obtain an aldehyde of formula 4. The first stage of the oxidative cleavage is conducted in the presence of: 1) a dihydroxylating reagent, preferably an osmium reagent such as osmium tetroxide; 2) a cooxidant such as N-morpholine-N-oxide; and 3) a mixture of aprotic polar and protic solvents such as a mixture of acetone, water, and t-butanol, at a temperature of between −20° C. and 40° C., preferably at 25° C., for a period of between 10 minutes and 48 hours, preferably for 3 hours. The second stage of the oxidative cleavage is conducted in the presence of: 1) a periodate salt such as sodium periodate; and 2) a mixture of aprotic polar and protic solvents such as a mixture of tetrahydrofuran and water, at a temperature of between −20° C. and 40° C., preferably at 25° C., for a period of between 10 minutes and 48 hours, preferably for 3 hours.

Step D involves the addition of a butene group to an aldehyde of formula 4 to obtain an alcohol of formula 5. The addition is conducted in the presence of: 1) a crotyl addition reagent, preferably a crotyltin reagent such as crotyltributyltin; 2) a Lewis acid such as borontrifluoride etherate; and 3) an inert organic solvent, preferably a halogenated hydrocarbon such as methylene chloride, at a temperature of between −100° C. and 5° C., preferably at −78° C., for a period of between 10 minutes and 48 hours, preferably for 2 hours.

Step E involves the silylation of an alcohol of formula 5 to obtain a silyl ether of formula 6. The silylation is conducted in the presence of: 1) a silylating reagent, preferably a t-butyldimethylsilylating reagent such as t-butyldimethylsilyltriflate; 2) a weak base, preferably a nitrogen-containing base, more preferably a pyridine base such as 2,6-lutidine; and 3) an inert organic solvent, preferably a halogenated hydrocarbon such as methylene chloride, at a temperature of between −100° C. and 5° C., preferably at −20° C., for a period of between 10 minutes and 48 hours, preferably for 2 hours.

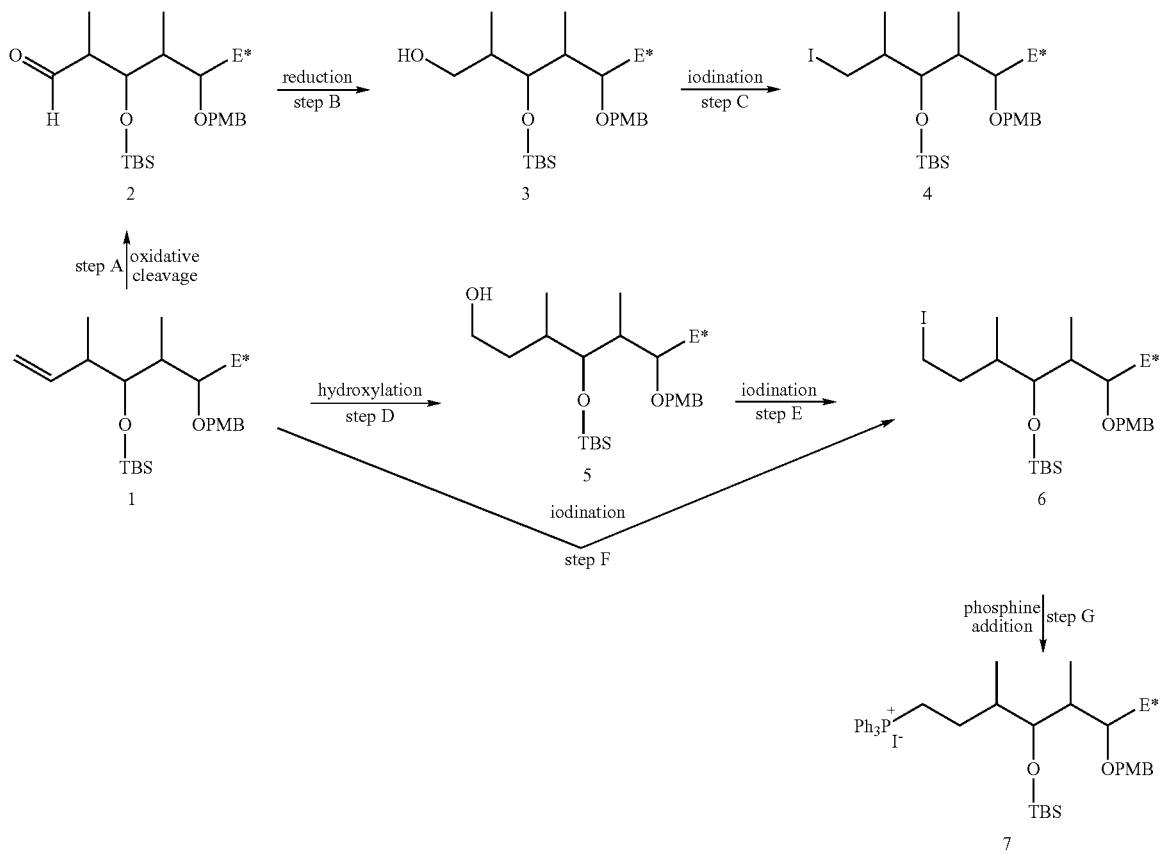

Scheme 21

The syntheses described in Scheme 21 may be applied when E* is not —CH(R$_7$)CH=CH—CH=CH$_2$ or —CH(R$_7$)CH=CH$_2$. As to the individual steps in Scheme 21, Step A involves the two stage oxidative cleavage of an alkene of formula 1 to obtain an aldehyde of formula 2. The first stage of the oxidative cleavage is conducted in the presence of: 1) a dihydroxylating reagent, preferably an osmium reagent such as osmium tetroxide; 2) a cooxidant such as N-morpholine-N-oxide; and 3) a mixture of aprotic polar and protic solvents such as a mixture of acetone, water, and t-butanol, at a temperature of between −20° C. and 40° C., preferably at 25° C., for a period of between 10 minutes and 48 hours, preferably for 3 hours. The second stage of the oxidative cleavage is conducted in the presence of: 1) a periodate salt such as sodium periodate; 2) a mixture of aprotic polar and protic solvents such as a mixture of tetrahydrofuran and water, at a temperature of between −20° C. and 40° C., preferably at 25° C., for a period of between 10 minutes and 48 hours, preferably for 3 hours.

Step B involves the reduction of an aldehyde of formula 2 to obtain an alcohol of formula 3. The reduction is conducted in the presence of: 1) a hydride reducing agent, preferably an aluminum hydride such as lithium aluminum hydride or diisobutylaluminum hydride, or a borohydride such as sodium borohydride; and 2) a polar organic solvent, preferably an ether such as tetrahydrofuran, at a temperature of between −100° C. and 40° C., preferably from −20° C. to 25° C., for a period of between 10 minutes and 48 hours, preferably for 2 hours.

Step C involves the iodination of an alcohol of formula 3 to obtain an iodide of formula 4. The iodination is conducted in the presence of: 1) an iodinating reagent such $I_2$; 2) a phosphorus-containing compound such as triphenylphoshine; 3) a weak base, preferably a weak nitrogen-containing base such as imidazole; and 4) a polar organic solvent, preferably an ester such as ethyl acetate, at a temperature of between −10° C. and 40° C., preferably at 25° C., for a period of between 10 minutes and 48 hours, preferably for 2 hours.

Step D involves the two stage hydroxylation of an alkene of formula-1 to obtain an alcohol of formula 5. The first stage of the hydroxylation is conducted in the presence of: 1) a borane such as 9-borabicyclo[3.3.1]nonane; and 2) a polar organic solvent, preferably an ether such as tetrahydrofuran, at a temperature of between −10° C. and 40° C., preferably at 0° C., for a period of between 1 hour and 48 hours, preferably for 24 hours. The second stage of the hydroxylation is conducted in the presence of: 1) an oxidant, preferably a peroxide such as hydrogen peroxide; 2) a strong alkali base, preferably a hydroxide base such as sodium hydroxide; and 3) a polar organic solvent, preferably an ether such as tetrahydrofuran, at a temperature of between −10° C. and 40° C., preferably at 0° C., for a period of between 10 minutes and 8 hours, preferably for 1 hour.

Step E involves the iodination of an alcohol of formula 5 to obtain an iodide of formula 6. The iodination is conducted in the presence of: 1) an iodinating reagent such $I_2$; 2) a phosphorus-containing compound such as triphenylphoshine; 3) a weak base, preferably a weak nitrogen-containing base such as imidazole; and 4) a polar organic solvent, preferably an ester such as ethyl acetate, at a temperature of between −10° C. and 40° C., preferably at 25° C., for a period of between 10 minutes and 48 hours, preferably for 2 hours.

Step F involves the two stage iodination of an alkene of formula 1 to obtain an iodide of formula 6. The first stage of the iodination is conducted in the presence of: 1) a borane such as 9-borabicyclo[3.3.1]nonane and 2) a polar organic solvent, preferably an ether such as tetrahydrofuran, at a temperature of between −10° C. and 40° C., preferably at 0° C., for a period of between 1 hour and 48 hours, preferably for 24 hours. The second stage of the iodination is conducted in the presence of $I_2$; and 2) a polar organic solvent, preferably an ether such as tetrahydrofuran, at a temperature of between −10° C. and 40° C., preferably at −0° C., for a period of between 10 minutes and 8 hours.

Step G involves the phoshine addition reaction of an iodide of formula 6 to obtain a phosphonium iodide salt of formula 7. The phoshine addition reaction is conducted in the presence of: 1) a phosphorus reagent such as triphenylphosphine; 2) a base, preferably an amine base such as diisopropylethylamine; and 3) an organic solvent, preferably a polar aprotic solvent such as acetonitrile, at a temperature of between 25° C. and 150° C., preferably at 90° C., for a period of between 1 hour and 72 hours, preferably for 18 hours.

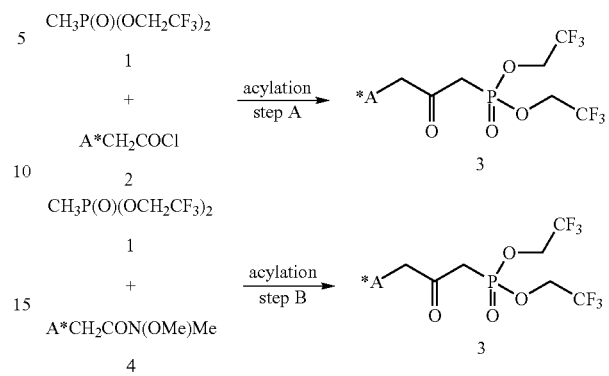

As to the individual steps in Scheme 22, Step A involves the acylation of a phosphonate of formula 1 with an acid chloride of formula 2 to obtain a ketophosphonate of formula 3. The acylation is conducted in the presence of: 1) a strong base, preferably an amine salt, more preferably a disubstituted amine salt such as lithiumdiisopropylamide or lithiumhexamethyldisilazide; and 2) a polar organic solvent, preferably an ether such as tetrahydrofuran, at a temperature of between −100° C. and 0° C., preferably from −100° C. to 40° C., for a period of between 10 minutes and 8 hours, preferably for 2 hours.

Step B involves the acylation of a phosphonate of formula 1 with an amide of formula 4 to obtain a ketophosphonate of formula 3. The acylation is conducted in the presence of: 1) a strong base, preferably an amine salt, more preferably a disubstituted amine salt such as lithiumdiisopropylamide or lithiumhexamethyldisilazide; and 2) a polar organic solvent, preferably an ether such as tetrahydrofuran, at a temperature of between −100° C. and 20° C., preferably from −78° C. to 0° C., for a period of between 10 minutes and 8 hours, preferably for 2 hours.

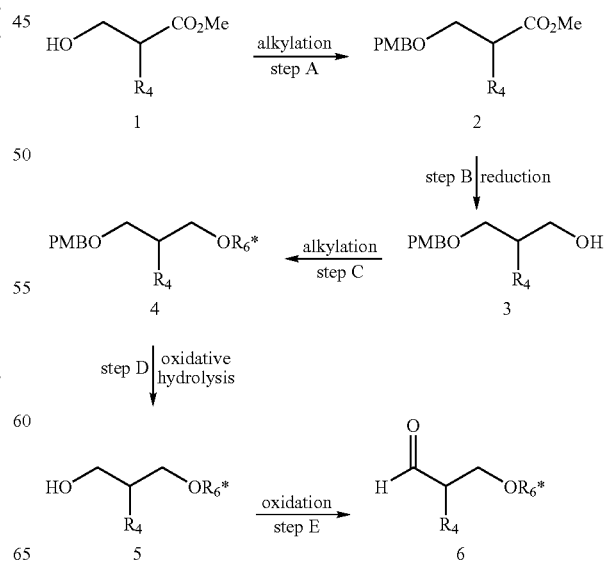

As to the individual steps in Scheme 23, Step A involves the alkylation of an alcohol of formula 1 to obtain an ether of formula 2. The alkylation is conducted in the presence of: 1) a reactive benzylating reagent, preferably a reactive para-methoxybenzylating reagent such as p-methoxybenzyl-2,2,2-trichloroacetimidate; 2) a proton source, preferably a sulfonic acid such as pyridinium p-toluenesulfonate; and 3) a polar organic solvent, preferably a halogenated hydrocarbon such as methylene chloride, at a temperature of between −78° C. and 25° C., preferably at 0° C., for a period of between 10 minutes and 48 hours, preferably for 3 hours.

Step B involves the reduction of an ether of formula 2 to obtain an alcohol of formula 3. The reduction is conducted in the presence of: 1) a metal hydride, preferably an aluminum hydride such as lithium aluminum hydride or diisobutylaluminum hydride; and 2) a polar organic solvent, preferably an ether such as tetrahydrofuran, at a temperature of between −100° C. and 10° C., preferably from −78° C. to 0° C., for a period of between 10 minutes and 8 hours, preferably for 2 hours.

Step C involves the alkylation of an alcohol of formula 3 to obtain an ether of formula 4. The alkylation is conducted in the presence of: 1) an alcohol of formula A*OH, where A* is as described above; 2) a coupling reagent such as diethyl azodicarboxylate; 3) a phosphine such as triphenylphosphine; and 4) a polar organic solvent, such tetrahydrofuran, at a temperature of between −78° C. and 60° C., preferably between −20° C. and 40° C., for a period of between 2 and 72 hours, preferably for 16 hours.

Step D involves the oxidative hydrolysis of an ether of formula 4 to an alcohol of formula 5. The oxidative hydrolysis is conducted in the presence of: 1) an oxidant, preferably a quinone such as 2,3-dichloro-5,6-dicyano-1,4-benzoquinone; 2) water; and 3) a polar organic solvent, preferably a halogenated hydrocarbon such as methylene chloride, at a temperature of between −20° C. and 40° C., preferably at 25° C., for a period of between 1 hour and 72 hours, preferably for 1 hour.

Step E involves the oxidation of an alcohol of formula 5 to obtain an aldehyde of formula 6. The oxidation is conducted in the presence of: 1) an oxidizing reagent, preferably a mild oxidizing reagent such as the combinations of oxalyl chloride, DMSO and triethylamine; sulfur trioxide-pyridine complex, DMSO and triethylamine; and 2,2,6,6-tetramethyl-1-piperidinyloxy free radical and diacetoxyiodobenzene; and 2) an inert organic solvent, preferably a polar organic solvent such as methylene chloride, at a temperature of between −78° C. and 40° C., preferably from −20° C. to 25° C., for a period of between 10 minutes and 48 hours, preferably for 3 hours.

Scheme 24

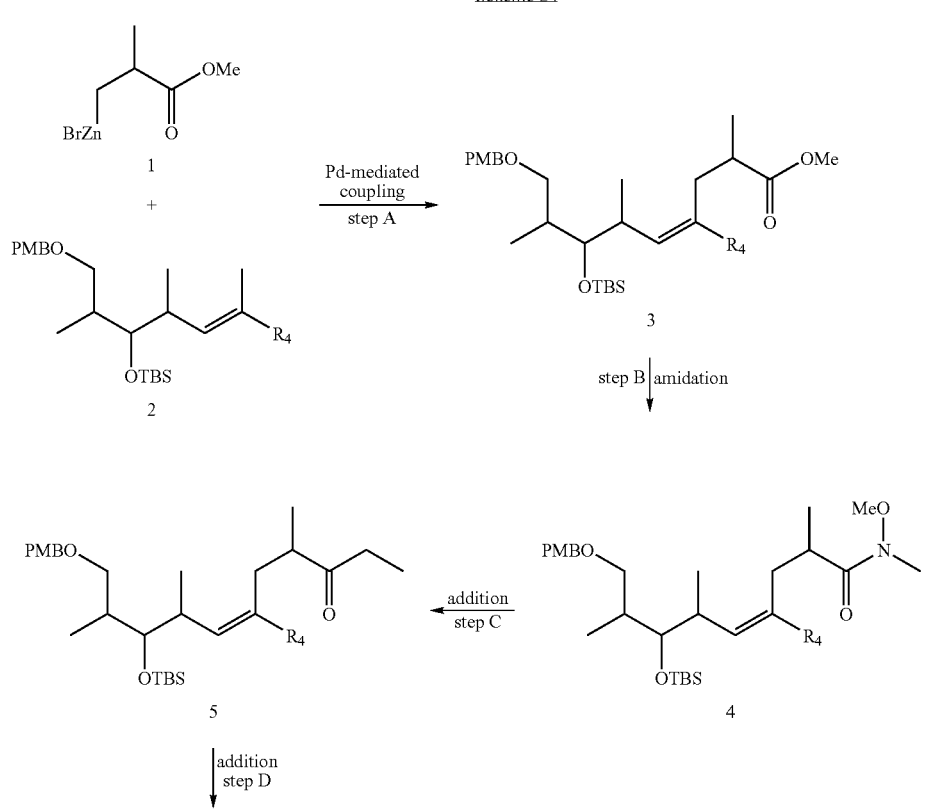

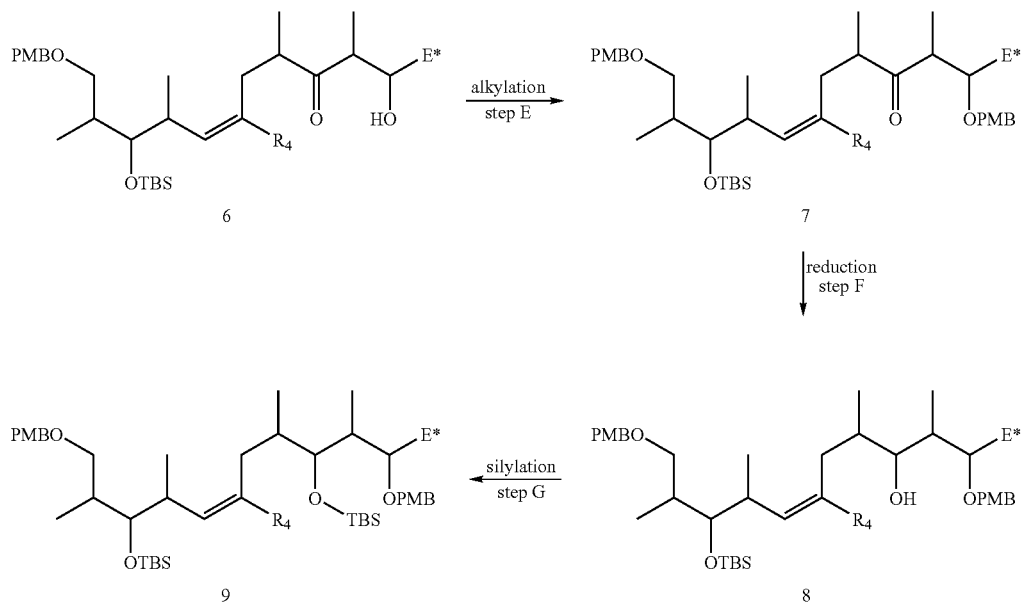

As to the individual steps in Scheme 24, Step A involves the palladium-mediated coupling of an alkyl zinc bromide of formula 1 and a vinyl iodide of formula 2 to obtain an alkene of formula 3. The palladium-mediated coupling is conducted in the presence of: 1) a palladium reagent such as tetrakis (triphenylphosphine)palladium(0); and 2) a polar organic solvent, preferably an ether such as diethyl ether or tetrahydrofuran, at a temperature of between −78° C. and 25° C., for a period of between 1 hour and 72 hours.

Step B involves the amidation of an alkene of formula 3 to obtain an amide of formula 4. The amidation is conducted in the presence of: 1) an O, N-dialkylated hydroxylamine such as N,N-dimethylhydroxylamine hydrochloride; 2) an organometallic reagent, preferably an alkylmagnesium halide or a trialkylaluminum reagent such as trimethylaluminum; and 3) an organic solvent, preferably a hydrocarbon such as toluene or hexane, or a mixture of the two, at a temperature of between −20° C. and 40° C., preferably at 25° C., for a period of between 1 hour and 72 hours, preferably for 1 hour.

Step C involves the addition reaction of an amide of formula 4 with a metalloalkane, preferably an alkyllithium or alkylmagnesium halide reagent such as ethylmagnesium bromide, to obtain a ketone of formula 5. The addition reaction is conducted in the presence of a polar organic solvent such as tetrahydrofuran, at temperature of between −100° C. and 0° C., preferably at −78° C., for a period of between 1 hour and 72 hours, preferably for 4 hours.

Step D involves the addition reaction of a ketone of formula 5 with an aldehyde of formula E*CHO to obtain a hydroxyketone of formula 6. The addition reaction is conducted in: 1) the presence a Lewis acid, preferably a boron or titanium reagent such as trisopropoxytitanium chloride; and 2) a polar organic solvent, preferably an ether such as diethyl ether or tetrahydrofuran, at a temperature of between −100° C. and 0° C., preferably at −78° C., for a period of between 1 hour and 72 hours, preferably for 16 hours.

Step E involves the alkylation of a hydroxyketone of formula 6 to obtain an ether of formula 7. The alkylation is conducted in the presence of: 1) a reactive benzylating reagent, preferably a reactive para-methoxybenzylating reagent such as p-methoxybenzyl-2,2,2-trichloroacetimidate; 2) a proton source, preferably a sulfonic acid such as pyridinium p-toluenesulfonate; and 3) a polar organic solvent, preferably a halogenated hydrocarbon such as methylene chloride, at a temperature of between −78° C. and 25° C., preferably at 0° C., for a period of between 10 minutes and 48 hours, preferably for 3 hours.

Step F involves the reduction of an ether of formula 7 to obtain an alcohol of formula 8. The reduction is conducted in the presence of: 1) a reducing agent, preferably an aluminum hydride or borohydride, such as lithium tri-t-butoxyaluminum hydride; 2) a polar organic solvent preferably an ether such as diethyl ether or tetrahydrofuran, at a temperature of between −100° C. and 0° C., preferably at −78° C., for a period of between 1 hour and 72 hours, preferably for 16 hours.

Step G involves the silylation of an alcohol of formula 8 to obtain an ether of formula 9. The silylation is conducted in the presence of: 1) a silylating reagent, preferably a t-butyldimethylsilylating reagent such as t-butyldimethylsilyltriflate; 2) a weak base, preferably a nitrogen-containing base, more preferably a pyridine base such as 2,6-lutidine; and 3) an inert organic solvent, preferably a halogenated hydrocarbon such as methylene chloride, at a temperature of between −100° C. and 5° C., preferably at −20° C., for a period of between 10 minutes and 48 hours, preferably for 2 hours.

Scheme 25

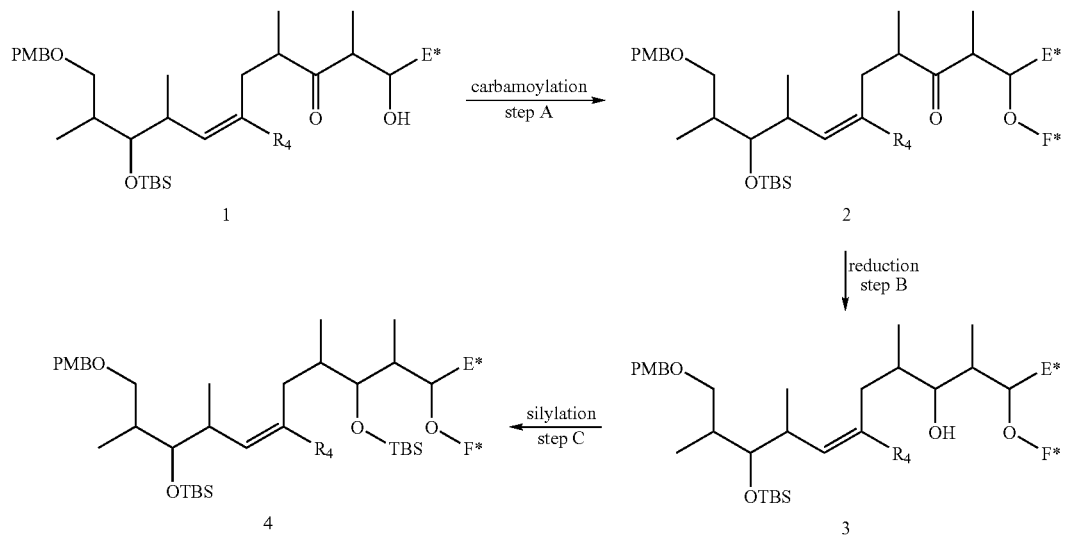

As to the individual steps in Scheme 25, Step A concerns the carbamoylation of the olefin of formula 1 with a an isocyanate either of formula F*NCO or $Cl_3C(O)NCO$ to give a carbamate of formula 2. In the case of using F*NCO, the carbamoylation is conducted in the presence of a Lewis acid such as $Bu_2Sn(OAc)_2$ or weak base such as triethylamine, in a polar aprotic solvent, preferably a halogenated solvent such as methylene chloride at a temperature of between −20° C. and 100° C., preferably between 0° C. and 50° C., for a period of between 5 minutes and 72 hours, preferably between 1 hour and 24 hours. In the case using $Cl_3C(O)NCO$, which produces substituted polyketides of formula I where F=H, the carbamoylation is conducted in the presence of a polar aprotic solvent, preferably a halogenated solvent such as methylene chloride at a temperature of between −20° C. and 100° C., preferably at 25° C., for a period of between 5 minutes and 72 hours, preferably between 1 hour and 8 hours; the work-up of this step is conducted in the presence of a protic organic solvent, preferably an alcohol such as methanol, in the presence of a base, for example, a carbonate such as potassium carbonate, at a temperature of between between 0° C. and 100° C., preferably at 25° C., for a period of between 5 minutes and 72 hours, preferably between 1 hour and 8 hours.

Step B involves the reduction of a carbamate of formula 2 to obtain an alcohol of formula 3. The reduction is conducted in the presence of: 1) a reducing agent, preferably an aluminum hydride or borohydride, such as lithium tri-t-butoxyaluminum hydride; and 2) a polar organic solvent preferably an ether such as diethyl ether or tetrahydrofuran, at a temperature of between −100° C. and 0° C., preferably at −78° C., for a period of between 1 hour and 72 hours, preferably for 16 hours.

Step C involves the silylation of an alcohol of formula 3 to obtain an ether of formula 4. The silylation is conducted in the presence of: 1) a silylating reagent, preferably a t-butyldimethylsilylating reagent such as t-butyldimethylsilyltriflate; 2) a weak base, preferably a nitrogen-containing base, more preferably a pyridine base such as 2,6-lutidine; and 3) an inert organic solvent, preferably a halogenated hydrocarbon such as methylene chloride, at a temperature of between −100° C. and 5° C., preferably at −20° C., for a period of between 10 minutes and 48 hours, preferably for 2 hours.

Scheme 26

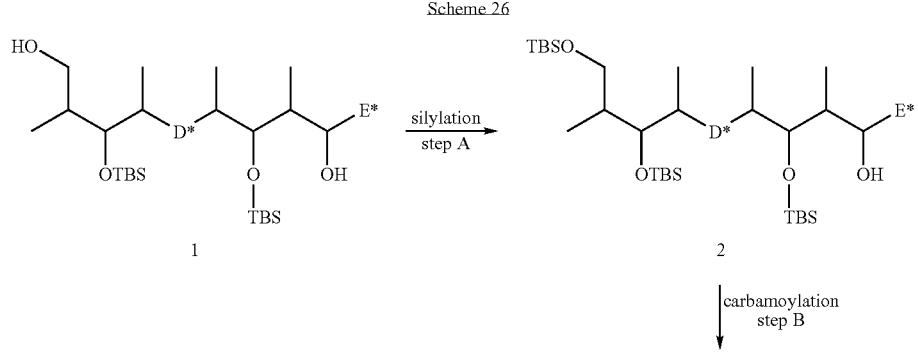

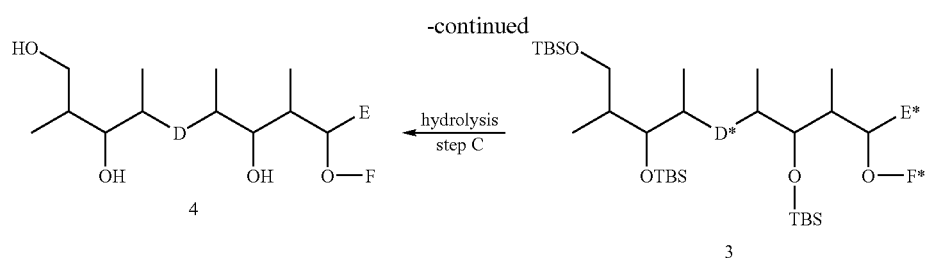

As to the individual steps in Scheme 26, Step A concerns the silylation of an alcohol of formula 1 to obtain an ether of formula 2. The silylation is conducted in the presence of: 1) a silylating reagent, preferably a t-butyldimethylsilylating reagent such as t-butyldimethylsilyltriflate; 2) a weak base, preferably a nitrogen-containing base, more preferably a pyridine base such as 2,6-lutidine; and 3) an inert organic solvent, preferably a halogenated hydrocarbon such as methylene chloride, at a temperature of between −100° C. and 5° C., preferably at −20° C., for a period of between 10 minutes and 48 hours, preferably for 2 hours.

Step B concerns the carbamoylation of the ether of formula 2 with a an isocyanate either of formula F*NCO or Cl₃C(O)NCO to give a carbamate of formula 3. In the case of using F*NCO, the carbamoylation is conducted in the presence of a Lewis acid such as Bu₂Sn(OAc)₂ or weak base such as triethylamine, in a polar aprotic solvent, preferably a halogenated solvent such as methylene chloride at a temperature of between −20° C. and 100° C., preferably between 0° C. and 50° C., for a period of between 5 minutes and 72 hours, preferably between 1 hour and 24 hours. In the case using Cl₃C(O)NCO, which produces substituted polyketides of formula I where F=H, the carbamoylation is conducted in the presence of a polar aprotic solvent, preferably a halogenated solvent such as methylene chloride at a temperature of between −20° C. and 100° C., preferably at 25° C., for a period of between 5 minutes and 72 hours, preferably between 1 hour and 8 hours; the work-up of this step is conducted in the presence of a protic organic solvent, preferably an alcohol such as methanol, in the presence of a base, for example, a carbonate such as potassium carbonate, at a temperature of between 0° C. and 100° C., preferably at 25° C., for a period of between 5 minutes and 72 hours, preferably between 1 hour and 8 hours.

Step C concerns the hydrolysis of a carbamate of formula 3 to a substituted polyketide of formula 4. The hydrolysis reaction is conducted in the presence of: 1) a protic acid, preferably an aqueous protic acid solution, preferably an aqueous hydrogen halide solution, such as aqueous hydrogen chloride; and 2) a polar organic solvent, preferably a mixture of polar organic solvents, preferably a mixture of an aliphatic alcohol and an ether, such as methanol and tetrahydrofuran, at a temperature of between −20° C. and 40° C., preferably between 20° C. and 25° C., for a period of between 8 hours and 7 days, preferably between 16 and 72 hours, more preferably between 24 and 48 hours.

Scheme 27

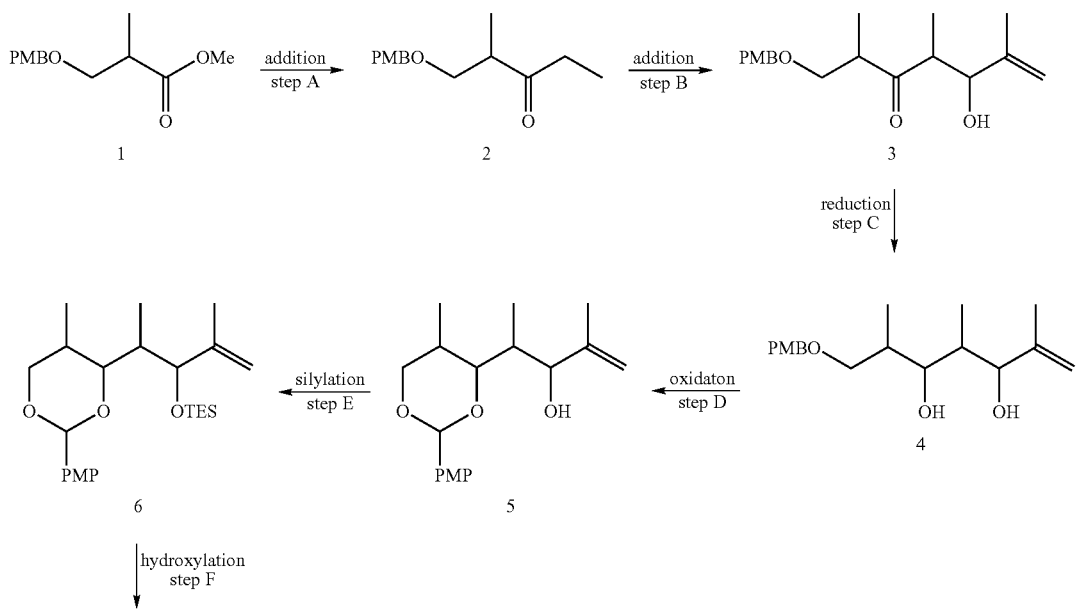

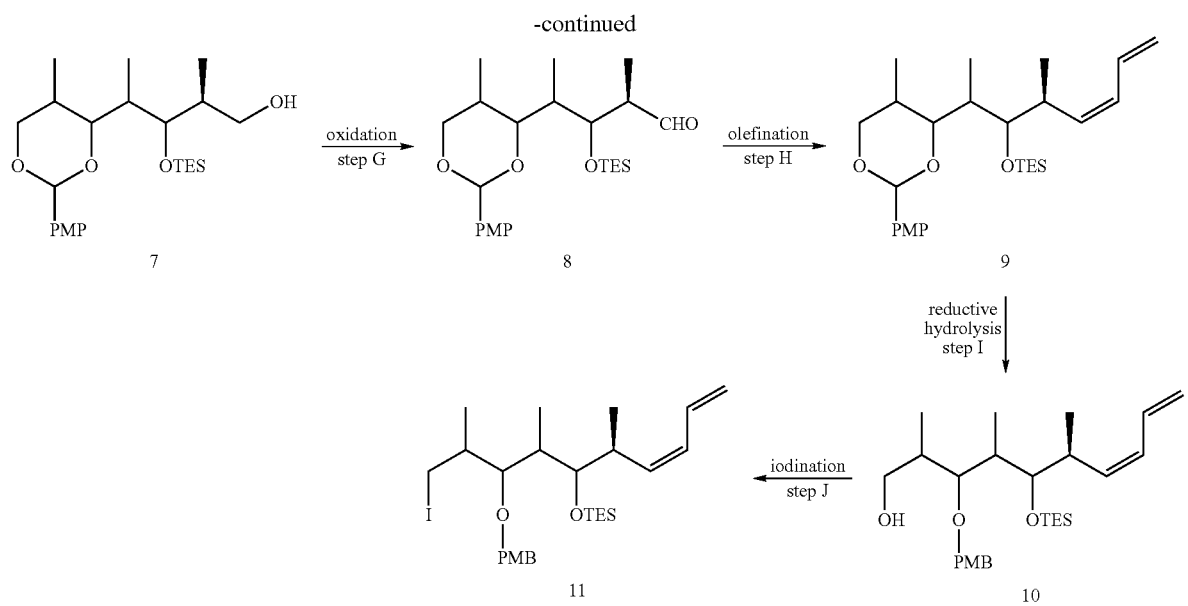

As to the individual steps in Scheme 27, Step A involves the addition reaction of an alkene of formula 1 to obtain a ketone of formula 2. The addition is conducted in the presence of: 1) an O,N-dialkylated hydroxylamine such as N,N-dimethylhydroxylamine hydrochloride; 2) an organometallic reagent, preferably ethylmagnesium bromide; and 3) an organic solvent, such as toluene, hexane or tetrahydrofuran, at a temperature of between −20° C. and 40° C., preferably at 25° C., for a period of between 1 hour and 72 hours, preferably for 1 hour.

Step B involves the addition reaction of a ketone of formula 2 with methacrolein to obtain a hydroxyketone of formula 3. The addition reaction is conducted in: 1) the presence of a Lewis acid, preferably a tin reagent such as tin(II) triflate; and 2) a polar organic solvent, preferably an ether such as diethyl ether or tetrahydrofuran, at a temperature of between −100° C. and 0° C., preferably at −78° C., for a period of between 1 hour and 72 hours, preferably for 16 hours.

Step C involves the reduction of a hydroxyketone of formula 3 to obtain an alcohol of formula 4. The reduction is conducted in the presence of: 1) a reducing agent, preferably an aluminum hydride, such as diisobutylaluminum hydride; and 2) a polar organic solvent, preferably an ether such as diethyl ether or tetrahydrofuran, at a temperature of between −100° C. and 0° C., preferably at −78° C., for a period of between 1 hour and 72 hours, preferably for 16 hours.

Step D involves the oxidation of an alcohol of formula 4 to obtain a cyclic ether of formula 5. The oxidation is conducted in the presence of: 1) an oxidant, preferably a quinone such as 2,3-dichloro-5,6-dicyano-1,4-benzoquinone; and 2) a polar organic solvent, preferably a halogenated hydrocarbon such as methylene chloride, at a temperature of between 40° C. and 20° C., preferably at 0° C., for a period of between 1 hour and 72 hours, preferably for 16 hours.

Step E involves the silylation of an alcohol of formula 5 to obtain a silyl ether of formula 6. The silylation is conducted in the presence of: 1) a silylating reagent, preferably a triethylsilylating reagent such as triethylsilyl triflate; 2) a weak base, preferably a nitrogen-containing base, more preferably a pyridine base such as 2,6-lutidine; and 3) an inert organic solvent, preferably a halogenated hydrocarbon such as methylene chloride, at a temperature of between −100° C. and 5° C., preferably at −20° C., for a period of between 10 minutes and 48 hours, preferably for 2 hours.

Step F involves the two stage hydroxylation of a silyl ether of formula 6 to obtain an alcohol of formula 7. The first stage of the hydroxylation is conducted in the presence of: 1) a borane such as 9-borabicyclo[3.3.1]nonane; and 2) a polar organic solvent, preferably an ether such as tetrahydrofuran, at a temperature of between −10° C. and 40° C., preferably at 0° C., for a period of between 1 hour and 48 hours, preferably for 24 hours. The second stage of the hydroxylation is conducted in the presence of: 1) an oxidant, preferably a peroxide such as hydrogen peroxide; 2) a strong alkali base, preferably a hydroxide base such as sodium hydroxide; and 3) a polar organic solvent, preferably an ether such as tetrahydrofuran, at a temperature of between −10° C. and 40° C., preferably at 0° C., for a period of between 10 minutes and 8 hours, preferably for 1 hour.

Step G involves the oxidation of an alcohol of formula 7 to obtain an aldehyde of formula 8. The oxidation is conducted in the presence of: 1) an oxidizing reagent, preferably a mild oxidizing reagent such as the combinations of oxalyl chloride, DMSO and triethylamine; sulfur trioxide-pyridine complex, DMSO and triethylamine; and 2,2,6,6-tetramethyl-1-piperidinyloxy free radical and diacetoxyiodobenzene; and 2) an inert organic solvent, preferably a polar organic solvent such as methylene chloride, at a temperature of between −78° C. and 40° C., preferably from −20° C. to 25° C., for a period of between 10 minutes and 48 hours, preferably for 3 hours.

Step H involves the olefination of an aldehyde of formula 8 to obtain a diene of formula 9. The olefination is conducted in the presence of: 1) a halogenated silyl propene such as 1-bromo-1-trimethylsilyl-2-propene; 2) a chromium(II) reagent such as chromium(II)chloride; and 3) a polar organic solvent, preferably an ether such as tetrahydrofuran, at a temperature of between −100° C. and 40° C., preferably at 20° C., for a period of between 10 minutes and 48 hours, preferably for 3 hours.

Step I involves the reductive hydrolysis of a diene of formula 9 to obtain an alcohol of formula 10. The reductive hydrolysis is conducted in the presence of: 1) a Lewis acidic hydride, preferably an aluminum hydride such as diisobutylaluminum hydride; and 2) a polar organic solvent, preferably a halogenated hydrocarbon such as methylene chloride, at a temperature of between −100° C. and 5° C., preferably at −78° C., for a period of between 10 minutes and 48 hours, preferably for 1 hour.

Step J involves the iodination of an alcohol of formula 10 to obtain an iodide of formula 11. The iodination is conducted in the presence of: 1) an iodinating reagent such as iodine; 2) a phosphorus-containing compound such as triphenylphoshine; 3) a weak base, preferably a weak nitrogen-containing base such as imidazole; and 4) a polar organic solvent, preferably an ester such as ethyl acetate, at a temperature of between −10° C. and 40° C., preferably at 25° C., for a period of between 10 minutes and 48 hours, preferably for 2 hours.

As to the individual steps in Scheme 28, Step A involves the palladium-mediated coupling of a vinyl iodide of formula 1 and an alkyl iodide of formula 2 to obtain an alkene of formula 3. The palladium-mediated coupling is conducted in the presence of: 1) a hindered organometallic reagent, preferably a hindered organolithium reagent such as t-butyllithium; 2) either a zinc halide such as zinc chloride or a hindered boron reagent such as 9-methoxy-9-borabicyclo[3.3.1]nonane; 3) a palladium reagent such as tetrakis(triphenylphosphine)palladium(0) or [1,1'-bis(diphenylphosphino)ferrocene]-dichloropalladium(II); and 4) a polar organic solvent, preferably an ether such as diethyl ether, at a temperature of between −78° C. and 25° C., for a period of between 1 hour and 72 hours.

Step B concerns the hydrolysis of an alkene 3 to an alcohol of formula 4. The hydrolysis reaction is conducted in the presence of: 1) a protic acid, preferably an aqueous protic acid solution, more preferably an aqueous hydrogen halide solution such as aqueous hydrogen chloride; and 2) a polar organic solvent, preferably a mixture of polar organic solvents, more preferably a mixture of an aliphatic alcohol and an ether such as methanol and tetrahydrofuran, at a

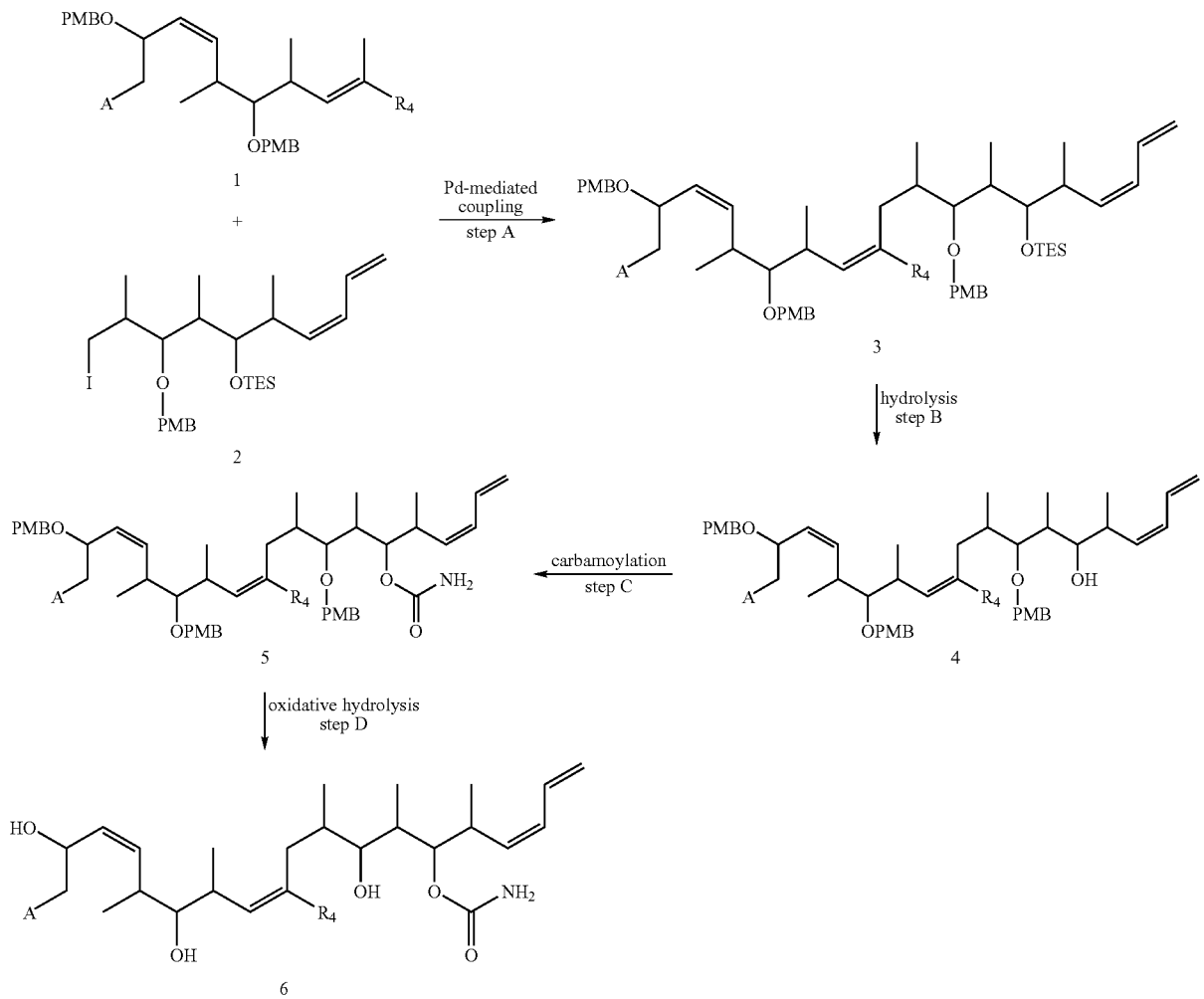

Scheme 28 temperature of between −20° C. and 40° C., preferably between 20° C. and 25° C., for a period of between 5 minutes and 24 hours, preferably between 0.5 and 12 hours.

Step C concerns the carbamoylation of an alcohol of formula 4 with an isocyanate of formula Cl₃C(O)NCO to give a carbamate of formula 5. The carbamoylation is conducted in the presence of a polar aprotic solvent, preferably a halogenated hydrocarbon such as methylene chloride, at a temperature of between −20° C. and 100° C., preferably at 25° C., for a period of between 5 minutes and 72 hours, preferably between 1 hour and 8 hours; the work-up of this step is conducted in the presence of a protic 100° C., preferably at 25° C., for a period of between 5 minutes and 72 hours, preferably between 1 hour and 8 hours.

Step D involves the oxidative hydrolysis of a carbamate of formula 5 to a substituted polyketide of formula 6. The oxidative hydrolysis is conducted in the presence of: 1) an oxidant, preferably a quinone such as 2,3-dichloro-5,6-dicyano-1,4-benzoquinone; 2) water; and 3) a polar organic solvent, preferably a halogenated hydrocarbon such as methylene chloride, at a temperature of between −20° C. and 40° C., preferably at 25° C., for a period of between 1 hour and 72 hours, preferably for 1 hour.

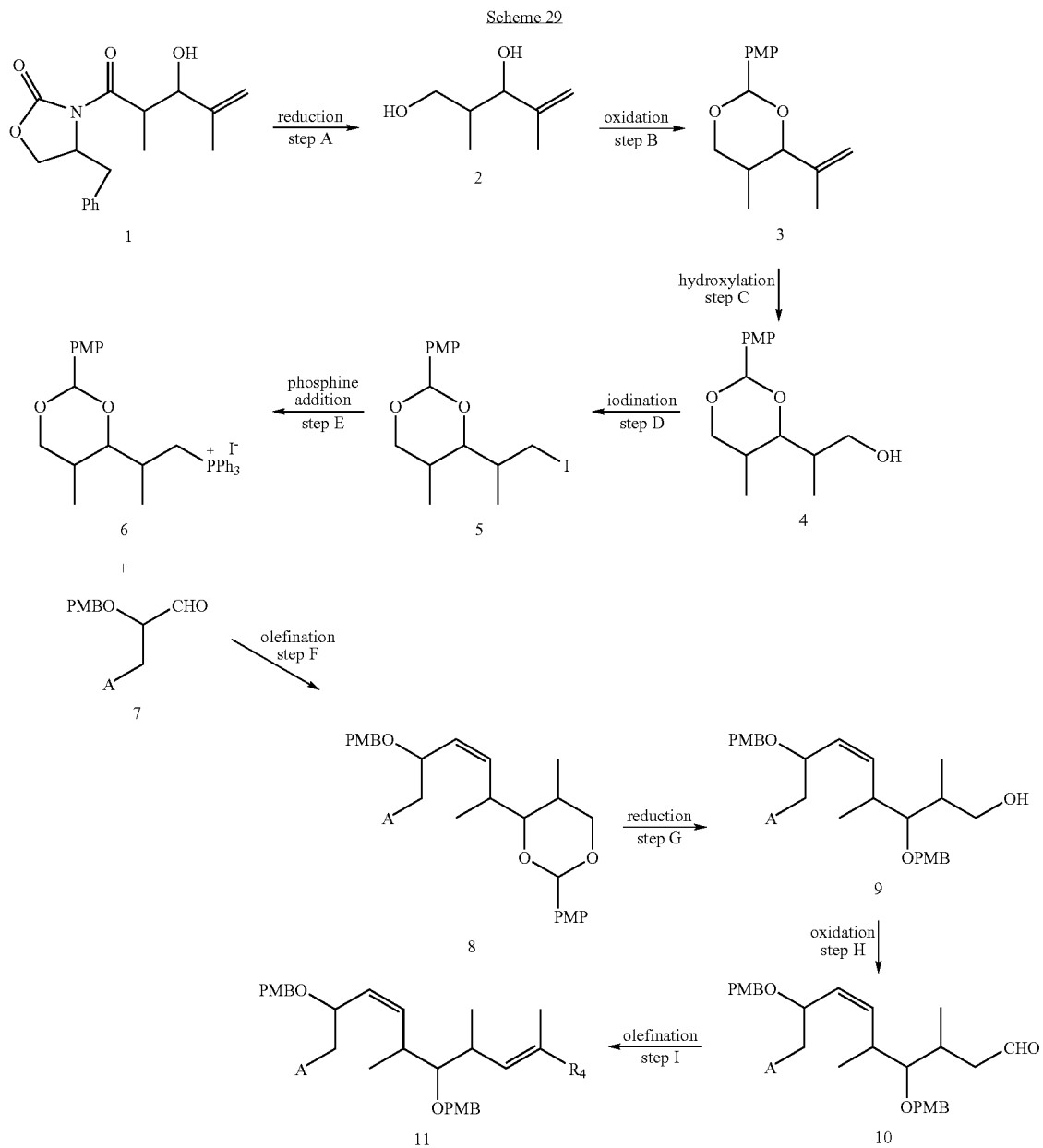

Scheme 29 organic solvent, preferably an alcohol such as methanol, and the presence of a base, for example, a carbonate such as potassium carbonate, at a temperature of between 0° C. and As to the individual steps in Scheme 29, Step A involves the reduction of an imide of formula 1 to obtain an alcohol of formula 2. The reduction is conducted in the presence of:

1) a hydride reducing agent such as lithium borohydride; 2) a protic organic solvent, preferably a lower alkanol such as ethanol; and 3) a polar organic solvent, preferably an ether such as tetrahydrofuran, at a temperature of between −20° C. and 40° C., preferably at 25° C., for a period of between 10 minutes and 48 hours, preferably for 18 hours.

Step B involves the oxidation of an alcohol of formula 2 to obtain a cyclic ether of formula 3. The oxidation is conducted in the presence of: 1) an oxidant, preferably a quinone such as 2,3-dichloro-5,6-dicyano-1,4-benzoquinone; and 2) a polar organic solvent, preferably a halogenated hydrocarbon such as methylene chloride, at a temperature of between 40° C. and 20° C., preferably at 0° C., for a period of between 1 hour and 72 hours, preferably for 16 hours.

Step C involves the two stage hydroxylation of a cyclic ether of formula 3 to obtain an alcohol of formula 4. The first stage of the hydroxylation is conducted in the presence of: 1) a borane such as 9-borabicyclo[3.3.1]nonane; and 2) a polar organic solvent, preferably an ether such as tetrahydrofuran, at a temperature of between −10° C. and 40° C., preferably at 0° C., for a period of between 1 hour and 48 hours, preferably for 24 hours. The second stage of the hydroxylation is conducted in the presence of: 1) an oxidant, preferably a peroxide such as hydrogen peroxide; 2) a strong alkali base, preferably a hydroxide base such as sodium hydroxide; and 3) a polar organic solvent, preferably an ether such as tetrahydrofuran, at a temperature of between −10° C. and 40° C., preferably at 0° C., for a period of between 10 minutes and 8 hours, preferably for 1 hour.

Step D involves the iodination of an alcohol of formula 4 to obtain an iodide of formula 5. The iodination is conducted in the presence of: 1) an iodinating reagent such as iodine; 2) a phosphorus-containing compound such as triphenylphoshine; 3) a weak base, preferably a weak nitrogen-containing base such as imidazole; and 4) a polar organic solvent, preferably an ester such as ethyl acetate, at a temperature of between −10° C. and 40° C., preferably at 25° C., for a period of between 10 minutes and 48 hours, preferably for 2 hours.

Step E involves the phoshine addition reaction of an iodide of formula 5 to obtain a phosphonium iodide salt of formula 6. The phoshine addition reaction is conducted in the presence of: 1) a phosphorus reagent such as triphenylphoshine; 2) a base, preferably an amine base such as diisopropylethylamine; and 3) an organic solvent, preferably a polar aprotic solvent such as acetonitrile, at a temperature of between 25° C. and 150° C., preferably at 90° C., for a period of between 1 hour and 72 hours, preferably for 18 hours.

Step F involves the olefination of an aldehyde of formula 7 with a phosphonium iodide salt of formula 6 to obtain an alkene of formula 8. The olefination is conducted in the presence of: 1) a strong base, preferably an alkali metal salt such as potassium hexamethyldisilazide or butyllithium; and 2) an inert organic solvent, preferably a hydrocarbon such as toluene, or an ether such as tetrahydrofuran, at a temperature of between −78° C. and 25° C., preferably at 0° C., for a period of between 10 minutes and 48 hours, preferably for 3 hours.

Step G involves the reductive hydrolysis of an alkene of formula 8 to obtain an alcohol of formula 9. The reductive hydrolysis is conducted in the presence of: 1) a Lewis acidic hydride, preferably an aluminum hydride such as diisobutylaluminum hydride; and 2) a polar organic solvent, preferably a halogenated hydrocarbon such as methylene chloride, at a temperature of between −100° C. and 5° C., preferably at −78° C., for a period of between 10 minutes and 48 hours, preferably for 1 hour.

Step H involves the oxidation of an alcohol of formula 9 to obtain an aldehyde of formula 10. The oxidation is conducted in the presence of: 1) an oxidizing reagent, preferably a mild oxidizing reagent such as the combinations of oxalyl chloride, DMSO and triethylamine; sulfur trioxide-pyridine complex, DMSO and triethylamine; and 2,2,6,6-tetramethyl-1-piperidinyloxy free radical and diacetoxyiodobenzene; and 2) an inert organic solvent, preferably a polar organic solvent such as methylene chloride, at a temperature of between −78° C. and 40° C., preferably from −20° C. to 25° C., for a period of between 10 minutes and 48 hours, preferably for 3 hours.

Step I involves the olefination of an aldehyde of formula 10 to obtain an iodoalkene of formula 11. The olefination is conducted in the presence of: 1) an alkyltriphenylphosphonium salt such as ethyltriphenylphosphonium iodide; 2) a strong base, preferably an alkali metal salt such as potassium hexamethyldisilazide or butyllithium; 3) an iodinating agent such as iodine; and 4) an inert organic solvent, preferably a hydrocarbon such as toluene, or an ether such as tetrahydrofuran, at a temperature of between −78° C. and 25° C., preferably at −20° C., for a period of between 10 minutes and 48 hours, preferably for 1 hour.

Scheme 30

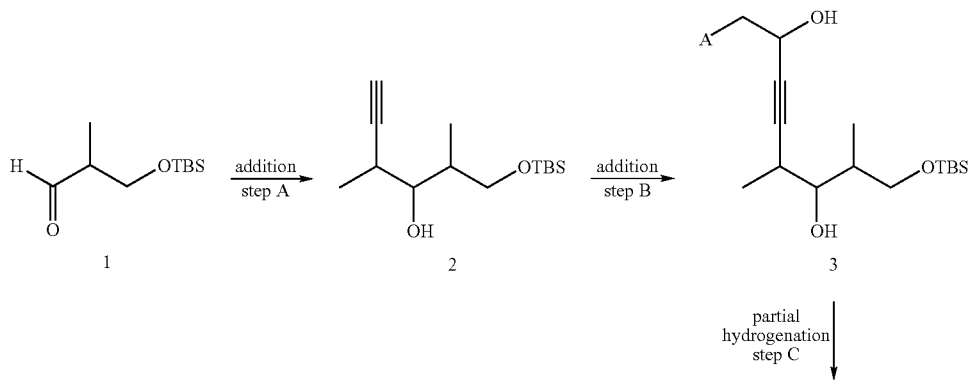

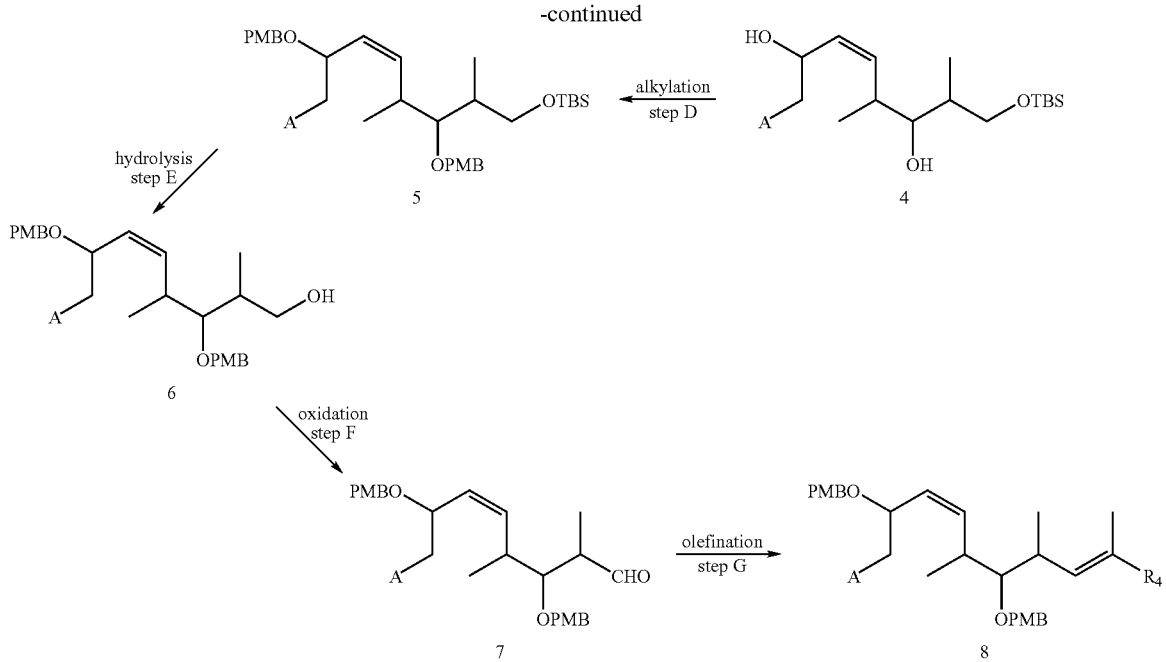

As to the individual steps in Scheme 30, Step A involves the addition reaction of an aldehyde of formula 1 to obtain an alkyne of formula 2. The addition is conducted in the presence of: 1) a propargyl alcohol, mesylate salt such as 3-butyn-2-ol, methanesulfonate; 2) a palladium reagent such as [1,1'-bis(diphenylphosphino)ferrocene]-dichloropalladium(II); 3) an indium reagent such as indium(I) iodide; and 4) polar organic mixture of solvents such as tetrahydrofuran and hexamethylphosphoramide, at a temperature of between −10° C. and 20° C., preferably at 0° C., for a period of between 10 minutes and 48 hours, preferably for 2 hours.

Step B involves the addition reaction of a alkyne of formula 2 to an aldehyde having formula $ACH_2CHO$ to obtain a propargyl alcohol of formula 3. The alkyne addition is conducted in the presence of: 1) a Lewis acid, preferably a zinc Lewis acid such as zinc triflate; 2) a hydroxylamine, preferably an ethanolamine such as N-methyl-ephedrine; 3) a base, preferably an amine base such as triethylamine; and 4) an inert organic solvent, preferably a hydrocarbon such as toluene, at a temperature of between 0° C. and 50° C., preferably at 25° C., for a period of between 10 minutes and 48 hours, preferably for 1 hour.

Step C involves the partial hydrogenation of a propargyl alcohol of formula 3 to obtain an alkene of formula 4. The hydrogenation is conducted in the presence of: 1) hydrogen; 2) a transition metal catalyst such as palladium; 3) an optional palladium poison such as quinoline; and 4) an organic solvent, preferably an alcohol such as methanol, or an ester such as ethyl acetate, at a temperature of between 0° C. and 35° C., preferably at 25° C., for a period of between 1 minute and 12 hours, preferably for 30 minutes.

Step D involves the alkylation of an alkene of formula 4 to obtain an ether of formula 5. The alkylation is conducted in the presence of: 1) a reactive benzylating reagent, preferably a reactive para-methoxybenzylating reagent such as p-methoxybenzyl-2,2,2-trichloroacetimidate; 2) a proton source, preferably a sulfonic acid such as pyridinium p-toluenesulfonate; and 3) a polar organic solvent, preferably a halogenated hydrocarbon such as methylene chloride, at a temperature of between −78° C. and 25° C., preferably at 0° C., for a period of between 10 minutes and 48 hours, preferably for 3 hours.

Step E concerns the hydrolysis of an ether of formula 5 to an alcohol of formula 6. The hydrolysis reaction is conducted in the presence of: 1) a protic acid, preferably an aqueous protic acid solution, preferably an aqueous hydrogen halide solution such as aqueous hydrogen chloride; and 2) a polar organic solvent, preferably a mixture of polar organic solvents, more preferably a mixture of an aliphatic alcohol and an ether such as methanol and tetrahydrofuran, at a temperature of between −20° C. and 40° C., preferably between 20° C. and 25° C., for a period of between 5 minutes and 24 hours, preferably between 0.5 and 12 hours.

Step F involves the oxidation of an alcohol of formula 6 to obtain an aldehyde of formula 7. The oxidation is conducted in the presence of: 1) an oxidizing reagent, preferably a mild oxidizing reagent such as the combinations of oxalyl chloride, DMSO and triethylamine; sulfur trioxide-pyridine complex, DMSO and triethylamine; and 2,2,6,6-tetramethyl-1-piperidinyloxy free radical and diacetoxyiodobenzene; and 2) an inert organic solvent, preferably a polar organic solvent such as methylene chloride, at a temperature of between −78° C. and 40° C., preferably from −20° C. to 25° C., for a period of between 10 minutes and 48 hours, preferably for 3 hours.

Step G involves the olefination of an aldehyde of formula 7 to obtain an iodoalkene of formula 8. The olefination is conducted in the presence of: 1) an alkyltriphenylphosphonium salt such as ethyltriphenylphosphonium iodide; 2) a strong base, preferably an alkali metal salt such as potassium hexamethyldisilazide or butyllithium; 3) an iodinating agent such as iodine; and 4) an inert organic solvent, preferably a hydrocarbon such as toluene, or an ether such as tetrahydrofuran, at a temperature of between −78° C. and 25° C., preferably at −20° C., for a period of between 10 minutes and 48 hours, preferably for 1 hour.

Scheme 31

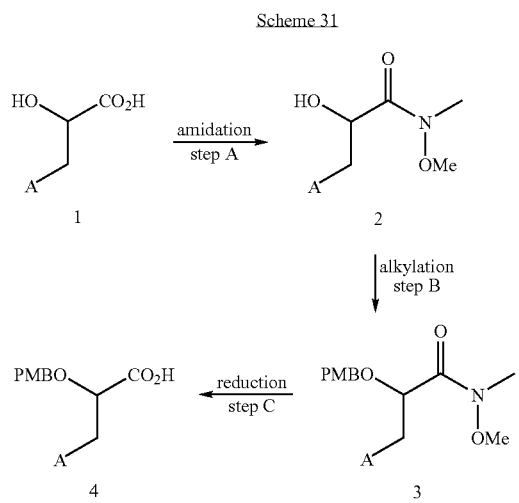

As to the individual steps in Scheme 31, Step A involves the amidation of a carboxylic acid of formula 1 to obtain an amide of formula 2. The amidation is conducted in the presence of: 1) an O,N-dialkylated hydroxylamine such as N,N-dimethylhydroxylamine hydrochloride; 2) a carboxylic acid coupling reagent, preferably a diimide such as 1-(3-dimethylaminopropyl)-3-ethylcarbodiimide hydrochloride, and a suitable activating agent common to diimide coupling reactions, such as 1-hydroxybenzotriazole; and 3) a polar organic solvent, preferably a low molcular weight amide such as DMF, at a temperature of between 0° C. and 40° C., preferably at 25° C., for a period of between 1 and 24 hours.

Step B involves the alkylation of an amide of formula 2 to obtain an ether of formula 3. The alkylation is conducted in the presence of: 1) a reactive benzylating reagent, preferably a reactive para-methoxybenzylating reagent such as p-methoxybenzyl-2,2,2-trichloroacetimidate; 2) a proton source, preferably a sulfonic acid such as pyridinium p-toluenesulfonate; and 3) a polar organic solvent, preferably a halogenated hydrocarbon such as methylene chloride, at a temperature of between −78° C. and 25° C., preferably at 0° C., for a period of between 10 minutes and 48 hours, preferably for 3 hours.

Step C involves the reduction of an ether of formula 3 to obtain an aldehyde of formula 4. The reduction is conducted in the presence of: 1) a metal hydride, preferably an aluminum hydride such as diisobutylaluminum hydride; and 2) a polar organic solvent, preferably an ether such as tetrahydrofuran, at a temperature of between −100° C. and 10° C., preferably from −78° C. to 0° C., for a period of between 10 minutes and 8 hours, preferably for 2 hours.

Although the product of each reaction described above may, if desired, be purified by conventional techniques such as chromatography or recrystallization (if a solid), the crude product of one reaction is advantageously employed in the following reaction without purification.

As is evident to those skilled in the art, compounds of formula I contain asymmetric carbon atoms. It should be understood, therefore, that the individual stereoisomers are contemplated as being included within the scope of this invention.

As indicated above, all of the compounds of formula I are anti-tumor agents and are, therefore, useful in inhibiting the growth of various lymphomas, sarcomas, carcinomas, myelomas, and leukemia cell lines. The anti-tumor activity of the compounds of formula I may be demonstrated employing the Anchorage Dependent Growth Monolayer Assay (ADGMA) which measures the growth inhibitory effects of test compounds on proliferation of adherent cell monolayers. This assay was adapted from the 60 cell line assay used by the National Cancer Institute (NCI) with the following modifications:

1) four cell lines representative for the important tumor types, viz., MIP 101 colon carcinoma, HCT 116 colon carcinoma, 1A9 ovarian carcinoma and 1A9PTX22 ovarian carcinoma were utilized; and 2) a tetrazolium derivative, viz., MTT, was utilized to determine cell density.

The ADGMA compares the number of viable cells following a 3-day exposure to a test compound relative to the number of cells present at the time the test compound was added. Cell viability is measured using a tetrazolium derivative, viz., 3-[4,5-dimethylthiazol-2-yl]-2,5-diphenyl-tetrazolium bromide (MTT) that is metabolically reduced in the presence of an electron coupling agent (PMS; phenazine methosulfate) by viable cells to a water-soluble formazan derivative. The absorbance at 540 nm (A540) of the formazan derivative is proportional to the number of viable cells. The $IC_{50}$ for a test compound is the concentration of compound required to reduce the final cell number to 50% of the final control cell number. If cell proliferation is inhibited, the assay further defines compounds as cytostatic (cell number after 3-day compound incubation>cell number at time of compound addition) or cytotoxic (cell number after 3-day compound incubation<cell number at time of compound addition).

The HCT 116 colon carcinoma cell line was obtained from the American Type Culture Collection (ATCC, Rockville, Md.). The MIP 101 colon carcinoma was obtained from Dr. Robert Kramer (Bristol Meyers Squibb) and was previously described (Niles R M, Wilhelm S A, Steele G D JR, Burke B, Christensen T, Dexter D, O'Brien M J, Thomas P, Zamcheck N. Isolation and characterization of an undifferentiated human colon carcinoma cell line (MIP 101). Cancer Invest. 1987;5(6):545–52). The 1A9 and the 1A9PTX22 ovarian tumor cell lines were obtained from Dr. Tito Fojo, Medicine Branch, Division of Clinical Sciences, National Cancer Institute, National Institutes of Health, Bethesda, Md. 20892. The 1A9 is a clone of the ovarian carcinoma cell line, A2780 (Giannakakou P, Sackett, D L, Kang Y-K, Zhan Z, Buters J T M, Fojo T, Poruchynsky M S. Paclitaxel-resistant human ovarian cancer cells have mutant β-tubulins that impaired paclitaxel-driven polymerization. J. Biol. Chem. 1997, 272(4):17118–17125). The 1A9PTX22 subline was isolated as an individual clone from the 1A9 cell line in a single step selection by exposure to 5 ng/mL paclitaxel in the presence of 5 µg/mL of verapamil. All cell lines were used between passages 4–20 following thawing. MIP 101 colon carcinoma, HCT 116 colon carcinoma, 1A9 ovarian carcinoma and 1A9PTX22 ovarian carcinoma cell lines are maintained and plated in RPMI 1640 medium containing 10% fetal bovine serum.

Cells are trypsinized and counted using a hemacytometer to determine cell concentrations. Cells were then plated in their respective maintenance media (200 µL/well) in 96-well plates at the following concentrations: MIP 101, 2000 cells/well, HCT 116, 2000 cells/well, 1A9, 10000 cells/well, and 1A9PTX22, 10000 cells/well. The number of cells/well was determined in preliminary experiments, and resulted in 75–90% of confluency by day 4 after plating. Initial cell densities, assayed one day after plating, are roughly 0.10–0.20 A540 absorbance units greater than the media blank. Ninety-six-well plates were seeded on day 0 and the test compounds are added on day 1. A "time 0" plate was created that received media only in row A and one cell line/row in rows B–E. The "time 0" plate was processed 24 hours after plating (at the time when drugs were added to experimental plates), as follows: To each well 5 micoliters of the MTT stock solution (0.5 mg/mL in PBS) was added to each well and then incubated for three hours at 37° C., 5% $CO_2$, in a humidified environment. Media was then carefully and completely removed. Plates were allowed to dry in the dark. Dimethylsulfoxide (DMSO) was added to each well (100 μL/well) and plates were placed on an orbital shaker for 2 hours. Plates were read in the 96-well plate reader at 540 nm in a Molecular Devices plate reader utilizing Softmax Version 2.35 in absorbance mode-endpoint L-1, using DMSO as a blank. One day following plating, test compounds were added (in a final 1:10 dilution) to the test plates and subsequently serial diluted 10 times. Control plate received 1:10 dilution of the solvent (10% DMSO/90% RPMI 1640) only. Three days after addition of test compounds, all the experimental plates and the control plate were processed as described above for the "time 0" plate. $IC_{50}$ values are determined from graphs of percent net growth as a function of compound concentration. Percent net growth is calculated as (Cell+Drug $A_{540}$–Initial 540/ Cell+Drug Vehicle 540–Initial 540).

ally, one or more other conventional pharmaceutical adjuvants and administered enterally, e.g., orally, in the form of tablets, capsules, caplets, etc. or parenterally, e.g., intraperitoneally or intravenously, in the form of sterile injectable solutions or suspensions. The enteral and parenteral compositions may be prepared by conventional means.

The compounds of formula I may be formulated into enteral and parenteral pharmaceutical compositions containing an amount of the active substance that is effective for inhibiting tumors, such compositions in unit dosage form and such compositions comprising a pharmaceutically acceptable carrier.

The compounds according to the invention can be administered alone or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents. In particular, a compound of formula I can be administered for example in the case of tumor therapy in combination with chemotherapy, radiotherapy, immunotherapy, surgical intervention, or a combination of these. Long-term therapy is equally possible as is adjuvant therapy in the context of other treatment strategies, as described above. Other possible

| Compound | MIP 101 | HCT116 | 1A9 | 1A9PTX22 |
|---|---|---|---|---|
| Ex. 1 | 0.06 ± 0.01 | 0.007 ± 0.005 | 0.006 ± 0.002 | 0.007 ± 0.002 |
| Ex. 2 | 3.2* | 0.4* | 0.5* | 0.4* |
| Ex. 3 | 0.4 ± 0.1 | 0.2 ± 0.1 | 0.3 ± 0.09 | 0.1 ± 0.04 |
| Ex. 4 | 3.2* | 0.8* | 0.5* | 0.4* |
| Ex. 5 | 0.6* | 0.3* | 0.4* | 0.08* |
| Ex. 6 | 0.006* | 0.001* | 0.0003* | 0.001* |
| Ex. 7 | 0.10* | 0.03* | 0.03* | 0.06* |
| Paclitaxel (a known antineoplastic compound) | 0.2 ± 0.06 | 0.0003 ± 0.0002 | 0.047 ± 0.007 | 0.001 ± 0.001 |

*Average of two independent experiments

The precise dosage of the compounds of formula I to be employed for inhibiting tumors depends upon several factors including the host, the nature and the severity of the condition being treated, the mode of administration and the particular compound employed. However, in general, satisfactory inhibition of tumors is achieved when a compound of formula I is administered parenterally, e.g., intraperitoneally, intravenously, intramuscularly, subcutaneously, intratumorally, or rectally, or enterally, e.g., orally, preferably intravenously or orally, more preferably intravenously at a single dosage of 1–300 mg/kg body weight per cycle (cycle=3–6 weeks) or, for most larger primates, a single dosage of 50–5000 mg per treatment cycle. A preferred intravenous single dosage per 3–6 week treatment cycle is 1–75 mg/kg body weight or, for most larger primates, a daily dosage of 50–1500 mg. A typical intravenous dosage is 45 mg/kg, once every three weeks.

Usually, a small dose is administered initially and the dosage is gradually increased until the optimal dosage for the host under treatment is determined. The upper limit of dosage is that imposed by side effects and can be determined by trial for the host being treated.

The compounds of formula I may be combined with one or more pharmaceutically acceptable carriers and, optiontreatments are therapy to maintain the patient's status after tumor regression, or even chemopreventive therapy, for example, in patients at risk.

Therapeutic agents for possible combination are especially one or more antiproliferative, cytostatic or cytotoxic compounds, for example, a chemotherapeutic agent or several agents selected from the group which includes, but is not limited to, an inhibitor of polyamine biosynthesis, an inhibitor of a protein kinase, especially of a serine/threonine protein kinase, such as protein kinase C, or of a tyrosine protein kinase, such as the EGF receptor tyrosine kinase, e.g., PKI166, the VEGF receptor tyrosine kinase, e.g., PTK787, or the PDGF receptor tyrosine kinase, e.g., ST1571, a cytokine, a negative growth regulator, such as TGF-β or IFN-β, an aromatase inhibitor, e.g., letrozole or anastrozole, an inhibitor of the interaction of an SH2 domain with a phosphorylated protein, antiestrogens, topoisomerase I inhibitors, such as irinotecan, topoisomerase II inhibitors, microtubule active agents, e.g., paclitaxel, discodermolide or an epothilone, alkylating agents, antineoplastic antimetabolites, such as gemcitabine or capecitabine, platin compounds, such as carboplatin or cisplatin, anti-angiogenic compounds, gonadorelin agonists, anti-androgens, bisphosphonates, e.g., AREDIA® or ZOMETA® and trastuzumab.

The structure of the active agents identified by code nos., generic or trade names may be taken from the actual edition of the standard compendium "The Merck Index" or from databases, e.g., Patents International (e.g., IMS World Publications). The corresponding content thereof is hereby incorporated by reference.

The following examples show representative compounds encompassed by this invention and their synthesis. However, it should be clearly understood that it is for purposes of illustration only.

EXAMPLE 1

6-[(2S,3Z,8Z,11S,12R,13S,14S,15S,16Z)-14-[(aminocarbonyl)oxy]-2,6,12-trihydroxy-5,7,9,11,13,15-hexamethyl-3,8,16,18-nonadecatetraenyl]tetrahydro-(6R)-2H-pyran-2-one a) Preparation of (7S,8Z,10S,11S,12S,13Z,16S,17R,18R,19S,20S,21Z)-19-[(aminocarbonyl)oxy]-11,17-bis[[(1,1-dimethylethyl)dimethylsilyl]oxy]-7-hydroxy-10,12,14,16,18,20-hexamethyl-5-oxo-8,13,21,23-tetracosatetraenoic acid ethyl ester.

hydrogen peroxide solution (50% aq., 1 mL) at 0° C. After stirring for 2 hours at room temperature (rt), the layers are separated and the aqueous layer is extracted with dichloromethane (3×10 mL). The combined organic layers are dried (MgSO$_4$), evaporated in vacuo and purified by flash chromatography (biotage, silica gel, gradient 10–30% EtOAc/Hexane) to give the desired compound as a colorless highly viscous oil (100 mg, 80%).

$^1$H NMR (300 MHz, CDCl$_3$), δ 6.61 (1H, ddd, J=16.6, 10.6, 10.5 Hz), 6.03 (1H, t, J=11.0), 5.58 (1H, t, J=10.1 Hz), 5.37 (1H, dd, J=10.6, 11.2 Hz), 5.35 (2H, m), 5.22 (1H, d, J=17.0 Hz), 5.13 (1H, d, J=10.2 Hz), 4.98 (1H, d, J=9.8 Hz), 4.70 (3H, m), 3.40 (1H, dd, J=5.7, 3.8 Hz), 3.26 (1H, dd, J=6.8, 3.8 Hz), 2.99 (2H, m), 266 (1H, m), 2.60–2.51 (2H, m), 2.35 (2H, m), 2.13 (1H, t, J=12.4 Hz), 1.90–1.87 (2H, m), 1.59 (1H, m), 0.99 (3H, d, J=6.8 Hz, Me), 0.94–0.83 (21H, m), 0.70 (3H, d, J=6.8 Hz), 0.10–0.01 (4×3H, m); $^{13}$C NMR (75 MHz, CDCl$_3$), δ 173.6, 157.3, 135.6, 133.9, 132.4, 132.2, 131.2, 129.2, 128.8, 118.2, 80.79, 80.9, 78.6,

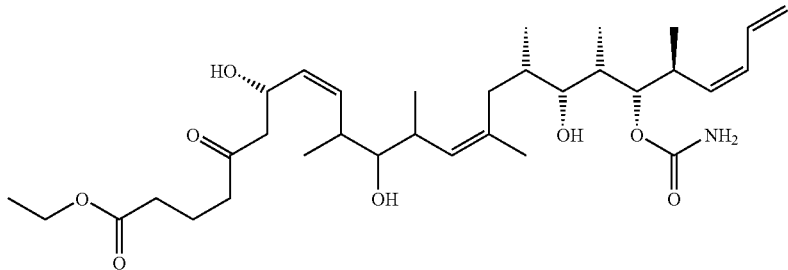

To a stirred solution of (+)-DIPCl (484 mg, 10 eq. 1.51 mmol) in Et$_2$O (2.0 mL) at 0° C. is added distilled triethylamine (0.23 mL, 11 eq) followed by addition of ethyl 5-oxohexanoate (239 mg, 1.51 mmol, 10 eq) by syringe. After stirring for 120 minutes at 0° C., the mixture is cooled to −78° C. (2R,3S,4R)-3-[[(1,1-dimethylethyl)dimethylsilyl]oxy]-N-methoxy-N,2,4-trimethyl-5-oxo-hexanamide (100 mg, 0.151 mmol) in Et$_2$O (1.0 mL) is added via cannula. After 3 hours at −78° C., the mixture is transferred to the freezer (−27° C.) and is allowed to stand at this temperature for 16 hours. The reaction is terminated by addition of MeOH (1 mL), pH=7 buffer solution (2 mL) and 77.2, 64.5, 60.7, 49.5, 42.5, 38.1, 37.2, 36.8, 36.7, 34.9, 34.6, 33.4, 26.4 (6C), 23.1, 19.3, 18.8, 18.7, 18.6, 17.8, 17.6, 14.4, 13.5, 10.3, −2.9, −3.1, −3.2, −3.6.

b) Preparation of (5R,7S,8Z,10S,11S,12S,13Z,16S,17R,18R,19S,20S,21Z)-19-[(aminocarbonyl)oxy]-11,17-bis[[(1,1-dimethylethyl)dimethylsilyl]oxy]-5,7-dihydroxy-10,12,14,16,18,20-hexamethyl-8,13,21,23-tetracosatetraenoic acid ethyl ester.

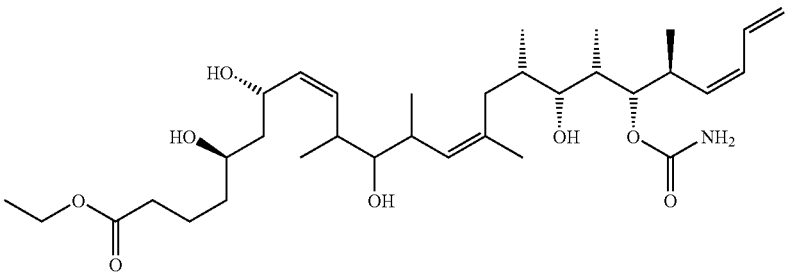

To a solution of 250 mg (0.95 mmol) of tetramethylammonium triacetoxyborohydride in 0.52 mL of anhydrous acetonitrile is added 0.52 mL of anhydrous acetic acid and the mixture is stirred at ambient temperature for 30 minutes.

The mixture is cooled to −29° C., and a solution of 50 mg (0.453 mmol) of (7S,8Z,10S,11S,12S,13Z,16S,17R,18R, 19S,20S,21Z)-19-[(aminocarbonyl)oxy]-11,17-bis[[(1,1-dimethylethyl)dimethylsilyl]oxy]-7-hydroxy-10,12,14,16, 18,20-hexamethyl-5-oxo-8,13,21,23-tetracosatetraenoic acid ethyl ester in 0.5 mL anhydrous acetonitrile is added. The mixture is stirred at −29° C. for 18 hours. The reaction is quenched with 1 mL of 0.5N aqueous sodium potassium tartrate and the mixture is allowed to warm slowly to ambient temperature. The mixture is diluted with $CH_2Cl_2$ and washed with aqueous saturated $NaHCO_3$. The aqueous layer is back extracted with $CH_2Cl_2$ four times. The combined organic layers are washed with brine, dried with $Na_2SO_4$ and concentrated in vacuo to give the crude product as a white solid (50 mg, 99%). m/z (ESI+) 846 (100 (M+Na+)).

c) Preparation of 6-[(2S,3Z,8Z,11S,12R,13S,14S,15S,16Z)-14-[(aminocarbonyl)oxy]-2,6,12-trihydroxy-5,7,9,11,13,15-hexamethyl-3,8,16,18-nonadecatetraenyl]tetrahydro-(6R)-2H-pyran-2-one

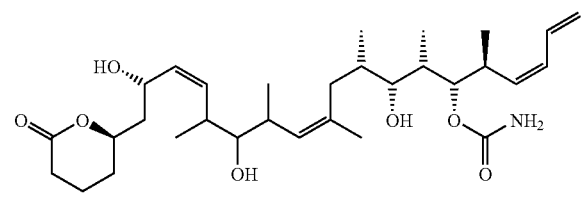

To a solution of (5R,7S,8Z,10S,11S,12S,13Z,16S,17R, 18R,19S,20S,21Z)-19-[(aminocarbonyl)oxy]-11,17-bis[[(1, 1-dimethylethyl)dimethylsilyl]oxy]-5,7-dihydroxy-10,12, 14,16,18,20-hexamethyl-8,13,21,23-tetracosatetraenoic acid ethyl ester (crude product from b) above) (50 mg, 0.452 mmol) in THF (56 mL) is added an aqueous solution of 4N HCl (56 mL). The resulting solution is stirred at rt for 24 hours and MeOH (10 mL) is added and the mixture is stirred for another 24 hours. EtOAc (50 mL) is added to the solution followed by the addition of $NaHCO_3$ at 0° C. to pH=8. The organic solution is washed with brine. The aqueous layer is extracted with EtOAc (3×30 mL), and the combined extracts are dried over $Na_2SO_4$, filtered, concentrated and purified by HPLC (50% $CH_2Cl_2$-EtOAc, then 100% EtOAc) to obtain the desired compound (3.3 mg, 10%).

$^1$H NMR (499 MHz, $CD_3CN$), δ 6.68 (ddd, J=16.7, 10.9, 10.5 Hz, 1H), 6.08 (t, J=11.0, Hz, 1H), 5.54 (t, J=10.7 Hz, 1H), 5.48 (t, J=10.6, 1H), 5.38 (dd, J=10.3, 8.6 Hz, 1H), 5.25 (d, J=16.8, Hz, 1H), 5.15 (d, J=10.1 Hz, 1H), 5.07 (br, $CONH_2$ 2H), 4.98 (d, J=10.0 Hz, 1H), 4.72 (dd, J=8.0, 4.2 Hz, 1H), 4.50 (m, 1H), 4.41 (m, 1H), 3.14 (dd, J=7.0, 3.8 Hz, 1H), 3.08 (m, 2H), 2.63 (m, 1H), 2.50 (m, 1H), 2.35 (t, J=7.9 Hz, 1H), 2.30 (m, 1H), 1.91–1.87 (m, 1H), 1.85–1.83 (m, 1H), 1.63 (m, 1H), 1.62 (m, 2H), 1.61 (s, 3H), 1.55–1.50 (m, 1H), 1.01 (d, J=7.0 Hz, 3H), 0.95 (d, J=6.8 Hz, 3H), 0.89 (d, J=6.8 Hz, 3H), 0.81 (d, J=6.6 Hz, 3H), 0.74 (d, J=6.8 Hz, 3H); $^{13}$C NMR (124.75 MHz, $CD_3CN$), δ 172.9, 158.7, 134.7, 134.6, 134.4, 134.1, 133.6, 131.5, 130.9, 118.9, 80.2, 79.7, 77.8, 76.4, 63.9, 45.2, 38.9, 37.4, 36.7, 36.5, 35.1, 34.7, 30.5, 29.5, 23.7, 20.1, 19.6, 18.6, 17.8, 15.9, 9.5; HRMS 572.3564 (M+Na+), Cal 572.3565.

EXAMPLE 2

(5Z,8S,9R,10S,11S,12S,13Z)-11-[(aminocarbonyl) oxy]-3,9-dihydroxy-2,4,6,8, 10,12-hexamethyl-5,13, 15-hexadecatrienyl ester cyclohexylcarbamic acid a) Preparation of, (2S,3R,4S,5Z,8S,9R,10R,11S,12S,13Z)-3,9-bis[[(1,1-dimethylethyl) dimethylsilyl]oxy]-11-hydroxy-2,4,6,8,10,12-hexamethyl-5,13,15-hexadecatrienyl ester cyclohexyl carbamic acid

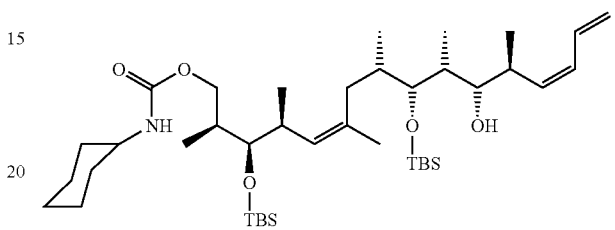

(2S,3R,4S,5Z,8S,9R,10R,11S,12S,13Z)-3,9-bis[[(1,1-dimethylethyl)dimethylsilyl]oxy]-2,4,6,8,10,12-hexamethyl-5,13,15-hexadecatriene-1,11-diol (215 mg, 0.36 mmol) is dissolved into dichloromethane (5 mL). Dibutyltin diacetate (113 mg, 0.90 mmol) is added, to the reaction mixture and stirred for 5 minutes. Then, cyclohexyl isocyanate is added dropwise into the reaction mixture. The resulting mixture is stirred overnight. The solvent is removed. The crude product is chromatographed (from hexane to 10% EtOAc in hexane) to give 257 mg (89%) of the desired compound a) as a colorless oil.

$^1$H NMR (300 MHz, $CDCl_3$), δ 6.60 (m, 1H), 6.09 (t, J=7, 1H), 5.29–4.94 (m, 4H), 3.99–3.98 (bs, 1H), 3.80–3.75 (m, 1H), 3.55–3.53 (m, 1H), 3.52–3.24 (m, 3H), 2.76–2.53 (m, 1H), 2.51–2.42 (m, 1H), 2.15 (t, J=8, 1H), 1.85–1.51 (m, 6H), 1.27–1.00 (m, 6H), 0.89–0.62 (m, 34H), −0.01–−0.11 (m, 12H); $^{13}$C NMR (300 MHz, $CDCl_3$), δ 155.96, 134.67, 132.53, 132.10, 131.05, 130.97, 118.43, 78.79, 77.85, 76.60, 76.36, 67.14, 60.39, 49.74, 38.31, 38.12, 36.29, 35.40, 34.94, 33.56, 26.23, 26.14, 25.53, 24.85, 23.25, 18.49, 18.39, 17.24, 16.60, 14.21, 14.09, 13.59, 9.45, −3.32, −3.60, −3.95, −4.00. Mass spectrum (ESI), m/z 722, 739 (m+$NH_3$).

b) Preparation of (2S,3R,4S,5Z,8S,9R,10R,11S,12S,13Z)-11-[(aminocarbonyl)oxy]-3,9-bis[[(1,1-dimethylethyl)dimethylsilyl]oxy]-2,4,6,8,10,12-hexamethyl-5,13,15-hexadecatrienyl ester cyclohexyl carbamic acid

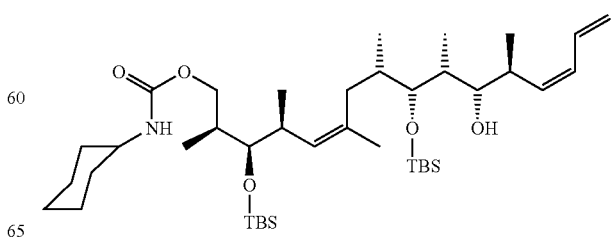

(2S,3R,4S,5Z,8S,9R,10R,11S,12S,13Z)-3,9-bis[[(1,1-dimethylethyl)dimethylsilyl]oxy]-11-hydroxy-2,4,6,8,10,12-hexamethyl-5,13,15-hexadecatrienyl ester cyclohexyl carbamic acid (100 mg, 0.14 mmol) is dissolved into dichloromethane (3 mL). Trichloroacetyl isocyanate (40 mg, 0.21 mmol) is added to the reaction mixture dropwise and stirred for 30 minutes. The solvent is removed in vacuo, methanol is added (3 mL), and then potassium carbonate is added (50 mg). This mixture is stirred for 2 hours. The solvent is then removed. The crude product is chromatographed (hexane to 10% EtOAc in hexane) to give 95 mg (90%) of the desired compound as a colorless oil.

$^1$H NMR (300 MHz, CDCl$_3$), δ 6.63 (m, 1H), 6.04 (t, J=7, 1H), 5.38 (m, 4H), 4.71 (m, 3H), 4.05–3.75 (m, 2H), 3.45 (m, 3H), 3.00 (m, 1H), 2.49 (m, 1H), 2.13 (m, 6H), 1.72 (m, 8H), 1.39–1.07 (m, 6H), 0.98 (m, 34H), 0.07 (m, 12H); $^{13}$C NMR (75 MHz, CDCl$_3$), δ 157.33, 156.35, 133.99, 132.80, 132.49, 131.28, 130.17, 118.33, 79.20, 78.16, 77.83, 76.98, 67.55, 60.78, 50.10, 38.83, 38.31, 36.49, 35.75, 35.64, 34.83, 33.93, 30.09, 26.60, 26.51, 25.91, 25.22, 23.38, 21.44, 18.91, 18.74, 17.89, 17.17, 14.59, 14.30, 14.11, 10.50, −3.03, −3.15, −3.63. Mass spectrum (ESI), m/z 765, 782 (m+NH$_3$).

c) Preparation of (5Z,8S,9R,10S,11S,12S,13Z)-11-[(aminocarbonyl)oxy]-3,9-dihydroxy-2,4,6,8,10,12-hexamethyl-5,13,15-hexadecatrienyl ester cyclohexylcarbamic acid.

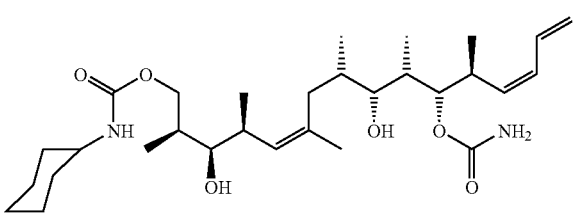

(2S,3R,4S,5Z,8S,9R,10R,11S,12S,13Z)-11-[(aminocarbonyl)oxy]-3,9-bis[[(1,1-dimethylethyl) dimethylsilyl]oxy]-2,4,6,8,10,12-hexamethyl-5,13,15-hexadecatrienyl ester cyclohexyl carbamic acid (32 mg, 0.04 mmol) is dissolved in isopropanol (1 mL). 4N HCl (0.75 mL) is added to the reaction mixture dropwise over 5 minutes. The mixture solution is stirred for 48 hours. The solvent is concentrated to dryness. The crude product is purified by HPLC to give 14 mg (54%) of the desired compound as a white powder.

$^1$H NMR (500 MHz, CDCl$_3$), δ 6.59 (m, 1H), 5.98 (t, J=10.8, 1H), 5.30 (t, J=10.4, 1H), 5.16 (d, J=16.7, 1H), 5.10 (m, 2H), 4.80 (bs, 1H), 4.65 (m, 3H), 4.07 (bs, 2H), 3.39 (m, 6H), 2.97 (m, 1H), 2.54 (m, 1H), 1.97 (m,7H), 1.65 (m, 5H), 1.30 (m, 2H), 1.12 (m, 3H), 0.97 (m, 12H), 0.83 (m, 3H); $^{13}$C NMR (125 MHz, CDCl$_3$), δ 157.65, 156.73, 134.27, 134.01, 132.58, 130.36, 130.18, 118.27, 79.24, 78.41, 75.85, 67.31, 50.39, 37.72, 36.67, 36.22, 35.92, 35.22, 33.79, 33.17, 25.87, 25.21, 23.64, 17.71, 16.51, 15.59, 13.73, 9.51. HRMS calcd for C$_{30}$H$_{52}$N$_2$O$_6$Na (M+Na)$^+$ 559.3723, found 559.3723.

EXAMPLE 3

(2Z,7Z,10S,11R,12S,13S,14S,15Z)-4,6,8,10,12,14-hexamethyl-1-phenoxy-2,7,15,17-octadecatetraene-5,11,13-triol-13-carbamate a) Preparation of (3Z,5S,6S,7R,8R,9S,11Z,13S,14S,15S,16Z)-8,14-bis[[(1,1-dimethylethyl) dimethylsilyl]oxy]-5,7,9,11,13,15-hexamethyl-18-phenoxy-1,3,11,16-octadecatetraen-6-ol carbamate.

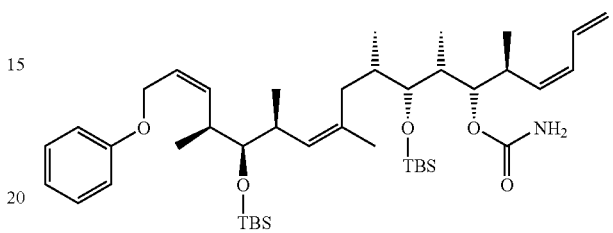

A THF solution of Ph$_3$P (118 mg, 0.452 mmol) is treated with DEAD (78 mg, 0.452 mmol) under N$_2$ at −78° C. After 10 minutes, PhOH and (2Z,4S,5S,6S,7Z,10S,11R,12R,13S,14S,15Z)-5,11-bis[[(1,1-dimethylethyl)dimethylsilyl]oxy]-4,6,8,10,12,14-hexamethyl-2,7,15,17-octadecatetraene-1,13-diol-13-carbamate are added.

The solution is warmed to 23° C. within 2 hours and stirred for 12 hours. THF is removed in vacuo and EtOAc (20 mL) is added. The organic solution is washed with H$_2$O (1×10 mL) and brine (1×10 mL). The aqueous layer is extracted with Et$_2$O (3×20 mL) and the combined extracts are dried (Na$_2$SO$_4$) and concentrated. Chromatography (SiO$_2$, 0–30% EtOAc-hexanes gradient elution) provided the desired compound (150 mg, 89%).

$^1$H NMR (300 MHz, CDCl$_3$); δ 7.28 (m, 2H), 6.95 (t, J=7.32 Hz, 1H), 6.9 (d, J=8.85 Hz, 2H), 6.61 (ddd, J=16.8, 10.6, 10.6 Hz, 1H), 6.03 (t, J=10.99 Hz, 1H), 5.77 (m, 2H), 5.39 (t, J=11.29 Hz, 1H), 5.35 (d, J=10.83 Hz, 1H), 5.22 (d, J=16.78 Hz, 1H), 5.14 (d, J=10.1 Hz, 1H), 4.96 (d, J=10.2 Hz, 1H), 4.76 (t, J=6.4 Hz, 1H), 4.55–4.39 (m, 3H), 3.42 (t, J=4.5 Hz, 1H), 3.30 (dd, J=7.5, 2.7 Hz, 1H), 2.99 (m, 1H), 2.67 (m, 1H), 2.38 (m, 1H), 2.12 (t, J=12.4 Hz, 1H), 1.99–1.84 (m, 2H), 1.64 (t, J=13.5 Hz, 1H), 1.60 (s, 3H), 1.01 (d, J=6.4 Hz, 3H), 0.99 (d, J=6.4 Hz, 3H), 0.92 (d, J=2.14 Hz, 6H), 0.90 (d, J=2.14 Hz, 3H), 0.72 (d, J=6.8 Hz, 3H), 0.11 (d, J=5.3 Hz, 6H), 0.07 (d, J=1.9 Hz, 6H); $^{13}$C NMR (75 MHz, CDCl$_3$), δ 159.0, 157.2, 136.3, 133.6, 132.9, 132.2, 130.8, 130.0, 129.8, 129.6, 124.5, 120.8, 115.5, 114.8, 81.1, 79.1, 77.4, 64.4, 38.2, 37.4, 37.2, 36.3, 35.1, 34.6, 26.4, 23.1, 19.2, 18.8, 18.7, 18.4, 17.7, 14.0, 10.3, −3.0, −3.1, −3.3, −3.4; HRMS ESI m/z 536.3354 (M+Na$^+$, C$_{31}$H$_{47}$O$_5$NNa requires 536.3351).

b) Preparation of (2Z,7Z,10S,11R,12S,13S,14S,15Z)-4,6,8,10,12,14-hexamethyl-1-phenoxy-2,7,15,17-octadecatetraene-5,11,13-triol-13-carbamate.

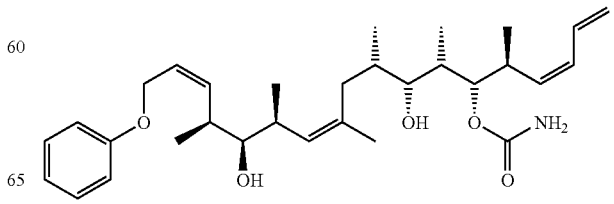

To a solution of (3Z,5S,6S,7R,8R,9S,11Z,13S,14S,15S,16Z)-8,14-bis[[(1,1-dimethylethyl) dimethylsilyl]oxy]-5,7,9,11,13,15-hexamethyl-18-phenoxy-1,3,11,16-octadecatetraen-6-ol carbamate (140 mg, 0.19 mmol, 1 eq) in MeOH (10 mL) is added a MeOH solution of HCl (15.5 mL, 15 mL MeOH+0.5 mL 12N HCl). The resulting solution is stirred at 23° C. for 36 hours. The pH is then adjusted to 8 by the addition of solid NaHCO$_3$ at 0° C. The solution is dried in vacuo, the residue is dissolved in CH$_2$Cl$_2$ (10 mL) and filtered through Celite. Chromatography (SiO$_2$, 50% CH$_2$Cl$_2$-EtOAc, then 100% EtOAc) provided the desired compound (75 mg, 77%) as a white solid: R$_f$=0.6 (SiO$_2$, EtOAc); [α]$^{25}_D$+66.215° (c 1.1, CH$_2$Cl$_2$); HRMS ESI m/z 536.3354 (M+Na$^+$, C$_{31}$H$_{47}$O$_5$NNa requires 536.3351).

1H NMR (300 MHz, CDCl$_3$), δ 7.28 (m, 2H), 6.95 (t, J=7.32 Hz, 1H), 6.90 (m, 3H), 6.60 (ddd, J=16.8, 10.6, 10.6 Hz, 1H), 6.03 (t, J=10.92 Hz, 1H), 5.70 (m, 1H), 5.69 (t, J=11.1 Hz, 1H), 5.35 (t, J=10.2 Hz, 1H), 5.22 (d, J=16.9 Hz, 1H), 5.12 (dd, J=12.1, 10.1 Hz, 2H), 4.72 (dd, J=7.17, 4.73 Hz, 1H), 4.51 (d, J=5.95 Hz, 2H), 4.48 (br s, 2H), 3.23 (m, 2H), 3.04–2.95 (m, 1H), 2.67 (m, 1H), 2.51 (m, 1H), 1.99–1.84 (m, 3H), 1.80 (dd, J=12.21, 8.24 Hz, 1H), 1.75 (m, 1H), 1.61 (s, 3H), 1.03 (d, J=6.8 Hz, 3H), 1.00 (d, J=6.5 Hz, 3H), 0.97 (d, J=2.14 Hz, 3H), 0.96 (d, J=2.14 Hz, 3H), 0.80 (d, J=2.14 Hz, 3H); $^{13}$C NMR (125 MHz, CDCl$_3$), δ 158.7, 156.9, 135.3, 133.7, 132.2, 129.9, 129.5, 125.6, 120.8, 117.9, 114.7, 79.4, 78.9, 76.4, 64.1, 37.0, 36.0, 35.8, 34.7, 33.0, 23.1, 18.4, 17.4, 16.5, 13.84, 8.7.

EXAMPLE 4

(2Z,7Z,10S,11R,12S,13S,14S,15Z)-13-[(aminocarbonyl)oxy]-5,11-dihydroxy-N,4,6,8,10,12,14-heptamethyl-N-phenyl 2,7,15,17-octadecatetraenamide a) Preparation of (2Z,4S,5S,6S,7Z,10S,11R,12R,13S,14S,15Z)-5,11-bis[[(1,1-dimethylethyl) dimethylsilyl]oxy]-13-hydroxy-N,4,6,8,10,12,14-heptamethyl-N-phenyl-2,7,15,17-octadecatetraenamide.

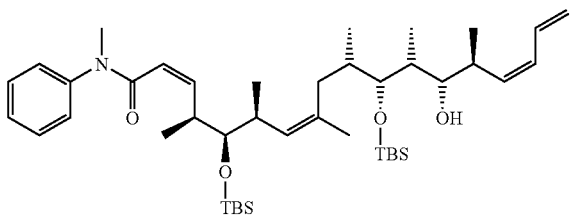

To a −20° C. solution of bis(2,2,2-trifluoroethyl)(N-methyl-N-phenylaminecarbonylmethyl) phosphonate (269 mg, 0.674 mmol, 2.67 eq) and 18-Crown-6 (134 mg, 0.506 mmol, 2 eq) in toluene (10 mL) is added KHMDS (1.35 mL, 0.5 M in tol, 0.674 mmol, 2.67 eq) over 2 minutes. The solution is warmed to 0° C. (10 minutes) and recooled to −20° C. To this solution is added a toluene solution of (2R,3R,4S,5Z,8S,9R,10R,11S,12S,13Z)-3,9-bis[[(1,1-dimethylethyl)dimethylsilyl]oxy]-11-hydroxy-2,4,6,8,10,12-hexamethyl-5,13,15-hexadecatrienal (150 mg, 0.253 mmol, 1 eq) dropwise. The solution is stirred at 0° C. (3 hours), quenched with saturated NH$_4$Cl (10 mL) and the aqueous layer extracted with EtOAc (3×10 mL). The organic extracts are combined, dried (MgSO$_4$) and concentrated to an oil. Chromatography (SiO$_2$, 10% EtOAc-hexane) provided the desired compound (110 mg, 60%) as a colorless oil.

$^1$H NMR (300 MHz, CDCl$_3$), δ 7.36 (t, J=7.2 Hz, 2H), 7.27 (t, J=7.2 Hz, 1H), 7.15 (d, J=7.5 Hz, 2H), 6.57 (ddd, J=16.6, 1.0.6, 10.2 Hz, 1H), 6.08 (t, J=6.1 Hz, 1H), 5.92 (dd, J=11.7, 10.7 Hz, 1H), 5.50 (d, J=11.6 Hz, 1H), 5.26 (t, J=10.6 Hz, 1H), 5.24 (dd, J=17.0, 1.9 Hz, 1H), 5.08 (d, J=10.1 Hz, 1H), 4.96 (d, J=10.2 Hz, 1H), 3.70 (m, 1H), 3.56 (dd, J=5.6, 2.6 Hz, 1H), 3.38 (dd, J=5.6, 3.4 Hz, 1H), 3.27 (m, 1H), 3.22 (s, 3H), 2.74 (m, 1H), 2.35 (m, 1H), 2.08 (t, J=12.5 Hz, 1H), 1.86–1.77 (m, 2H), 1.53 (s, 3H), 0.96 (d, J=6.7 Hz, 3H), 0.90 (d, J=7.2 Hz, 3H), 0.86 (d, J=3.8 Hz, 3H), 0.84 (d, J=4.1 Hz, 18H), 0.67 (d, J=6.8 Hz, 3H), 0.10–0.0 (m, 12H); $^{13}$C NMR (75 MHz, CDCl$_3$), δ 166.3, 148.6, 144.4, 135.0, 132.34, 132.27, 131.11, 131.06, 129.58, 127.38, 127.31, 119.25, 118.52, 80.85, 78.87, 76.37, 60.53, 38.05, 37.59, 37.53, 37.14, 36.48, 36.06, 35.15, 26.34, 23.44, 18.59, 18.39, 17.53, 17.31, 13.66, 9.67, −3.26, −3.42 (2C), −3.71.

b) Preparation of (2Z,4S,5S,6S,7Z,10S,11R,12R,13S,14S,15Z)-13-[(aminocarbonyl)oxy]-5,11-bis[[(1,1-dimethylethyl)dimethylsilyl]oxy]-N,4,6,8,10,12,14-heptamethyl-N-phenyl-2,7,15,17-octadecatetraenamide.

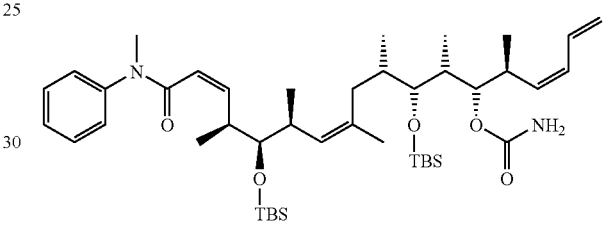

To a solution of (2Z,4S,5S,6S,7Z,10S,11R,12R,13S,14S,15Z)-5,11-bis[[(1,1-dimethylethyl) dimethylsilyl]oxy]-13-hydroxy-N,4,6,8,10,12,14-heptamethyl-N-phenyl-2,7,15,17-octadecatetraenamide (110 mg, 0.152 mmol, 1 eq) in CH$_2$Cl$_2$ (2 mL) is treated with trichloroacetyl isocyanate (43 mg, 0.228 mmol, 1.5 eq) at 23° C. (20 minutes). The solution is concentrated, and the residue dissolved in CH$_3$OH (2 mL). To this solution is added K$_2$CO$_3$ (0.1 g) and the mixture is stirred at 23° C. (2 hours). The reaction mixture is concentrated and the residue dissolved in Et$_2$O (5 mL). The organic solution is washed with H$_2$O (1×20 mL) and brine (1×20 mL). The aqueous layer is extracted with Et$_2$O (3×5 mL) and the combined extracts are dried (Na$_2$SO$_4$) and concentrated. Chromatography (SiO$_2$, 30–50% EtOAc-hexanes gradient elution) provided the desired compound (70 mg, 60%).

$^1$H NMR (300 MHz, CDCl$_3$), δ 7.36 (t, J=7.2 Hz, 2H), 7.27 (t, J=7.2 Hz, 1H), 7.15 (d, J=7.5 Hz, 2H), 6.59 (ddd, J=17.0, 10.6, 10.5 Hz, 1H), 6.00 (t, J=10.9 Hz, 1H), 5.91 (dd, J=11.7, 9.8 Hz, 1H), 5.54 (d, J=11.7 Hz, 1H), 5.36 (t, J=10.6 Hz, 1H), 5.25 (dd, J=16.2, 1.9 Hz, 1H), 5.06 (d, J=10.2 Hz, 1H), 4.98 (d, J=10.2 Hz, 1H), 4.72 (t, J=6.0 Hz, 1H), 4.62 (br, 2H), 3.70 (m, 1H), 3.42 (m, 2H), 3.23 (s, 3H), 2.98 (m, 1H), 2.40 (m, 1H), 2.07 (t, J=12.0 Hz, 1H), 1.92–1.81 (m, 2H), 1.66 (d, J=12.5 Hz, 1H), 1.52 (s, 3H), 0.96 (d, J=6.7 Hz, 3H), 0.90 (d, J=7.2 Hz, 3H), 0.88 (d, J=3.8 Hz), 0.86 (d, J=4.1 Hz, 18H), 0.70 (d, J=3.8 Hz, 3H), 0.10–0.0 (m, 12H); $^{13}$C NMR (75 MHz, CDCl$_3$), δ 166.3, 157.2, 148.6, 144.4, 135.8, 132.21, 132.15, 130.92, 129.89, 129.50, 127.30, 127.21, 119.24, 118.04, 80.67, 78.88, 76.81, 60.49, 37.62, 37.58, 37.15, 37.07, 35.92, 35.34, 34.59, 26.28, 23.02, 18.58, 18.52, 17.98, 17.63, 17.55, 13.79, 10.32, −3.37, −3.45, −3.52, −3.84.

c) Preparation of (2Z,7Z,10S,11R,12S,13S,14S,15Z)-13-[(aminocarbonyl)oxy]-5,11-dihydroxy-N,4,6,8,10,12,14-heptamethyl-N-phenyl 2,7,15,17-octadecatetraenamide.

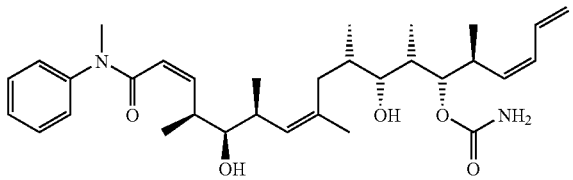

To a solution of (2Z,4S,5S,6S,7Z,10S,11R,12R,13S,14S,15Z)-13-[(aminocarbonyl)oxy]-5,11-bis[[(1,1-dimethylethyl)dimethylsilyl]oxy]-N,4,6,8,10,12,14-heptamethyl-N-phenyl-2,7,15,17-octadecatetraenamide (70 mg, 0.091 mmol, 1 eq) in MeOH (10 mL) is added a MeOH solution of HCl (15.5 mL, 15 mL MeOH+0.5 mL 12N HCl). The resulting solution is stirred at 23° C. (36 hours). The pH is adjusted to 8 by the addition of solid NaHCO$_3$ at 0° C. The solution was dried in vacuo, the residue was dissolved in CH$_2$Cl$_2$ (10 mL) and filter through Celite. HPLC purification provided the desired compound (15.5 mg, 32%) as a white solid: [α]$^{25}_D$=+225.7380 (c 0.25, CH$_2$Cl$_2$); HRMS ESI m/z 541.3588 (M+H$^+$, C$_{32}$H$_{50}$O$_5$N$_2$ requires 541.3641).

$^1$H NMR (500 MHz, CDCl$_3$), δ 7.41 (t, J=7.5 Hz, 2H), 7.33 (t, J=7.3 Hz, 1H), 7.17 (d, J=7.4 Hz, 2H), 6.62 (ddd, J=17.0, 10.6, 10.4 Hz, 1H), 6.02 (t, J=10.8 Hz, 1H), 5.75 (t, J=11.3 Hz, 1H), 5.67 (d, J=11.4 Hz, 1H), 5.38 (m, 2H), 5.18 (d, J=16.8 Hz, 1H), 5.08 (d, J=10.1 Hz, 1H), 4.70 (m, 1H), 3.41 (m, 1H), 3.35 (m, 1H), 3.33 (s, 3H), 3.19 (m, 1H), 3.01 (m, 1H), 2.71 (m, 1H), 2.43 (d, J=5.5 Hz, 1H), 2.15 (dd, J=12.7, 6.9 Hz, 1H), 1.98–1.91 (m, 2H), 1.80 (dd, J=12.9, 7.8 Hz, 1H), 1.68 (s, 3H), 1.02 (d, J=2.1 Hz, 3H), 1.00 (d, J=2.3 Hz, 6H), 0.99 (d, J=2.1 Hz, 3H), 0.87 (d, J=6.7 Hz, 3H); $^{13}$C NMR (75 MHz, CDCl$_3$), δ 167.8, 157.1, 148.5, 143.4, 134.2, 132.9, 132.3, 129.9, 129.7, 129.6, 127.7, 126.9, 121.7, 117.5, 78.5, 78.4, 78.0, 76.8, 74.4, 37.3, 37.2, 37.0, 35.9, 35.6, 34.8, 32.6, 23.5, 17.5, 17.3, 15.0, 13.9, 9.0.

EXAMPLE 5

Synthesis of N-[(5Z,8S,9R,10S,11S,12S,13Z)-11-(2-amino-2-oxoethyl)-3,9-dihydroxy-2,4,6,8,10,12-hexamethyl-5,13,15-hexadecatrienyl]-N-methyl-cyclohexaneacetamide a) Preparation of (3Z,5S,6S,7R,8R,9S,11Z,13S,14R,15S)-8,14-bis[[(1,1-dimethylethyl)dimethylsilyl]oxy]-5,7,9,11,13,15-hexamethyl-16-(methylamino)-1,3,11-hexadecatrien-6-ol.

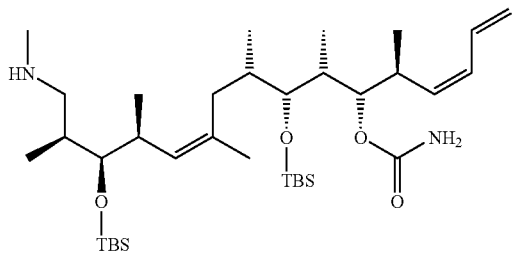

To a stirred THF solution of methylamine (2 M, 1.01 mL, 4 eq, 2.02 mmol) is added THF (10 mL) solution of (2R,3R,4S,5Z,8S,9R,10R,11S,12S,13Z)-3,9-bis[[(1,1-dimethylethyl) dimethylsilyl]oxy]-11-hydroxy-2,4,6,8,10,12-hexamethyl-5,13,15-hexadecatrienal (300 mg, 0.505 mmol, 1 eq) at 23° C. After stirring for 20 minutes, NaBHAc$_3$ is added followed by addition of 1 drop of AcOH. The solution is stirred for an additional 2 hours and diluted with EtOAc (10 mL), washed with aqueous saturated Na$_2$CO$_3$ (2×5 mL), brine, dried with Na$_2$SO$_4$ and concentrated in vacuo. The residue is purified by flash chromatography (silica gel, gradient 10–30% MeOH/EtOAc) to give the desired compound (180 mg, 59%) as a colorless oil.

$^1$H NMR (300 MHz, CDCl$_3$), δ 6.63 (ddd, J=16.7, 10.9, 10.5 Hz, 1H), 6.14 (t, J=10.9 Hz, 1H), 5.34 (t, J=10.5 Hz, 1H), 5.24 (d, J=16.9, Hz, 1H), 5.15 (d, J=9.8 Hz, 1H), 5.02 (d, J=10.2 Hz, 1H), 3.63 (m, 1H), 3.32 (m, 2H), 2.81 (m, 1H), 2.61 (m, 1H), 2.52 (m, 1H), 2.38 (d, J=3.8 Hz, 3H), 2.37 (m, 1H), 2.20 (m, 1H), 1.65–1.95 (m, 3H); 1.59 (m, 4H); 1.08 (d, J=7.0, 3H), 1.00–0.94 (m, 9H), 0.93 (s, 9H), 0.90 (s, 9H), 0.74 (d, J=6.7, 3H), 0.10 (s, 6H), 0.09 (s, 6H); $^{13}$C NMR (75 MHz, CDCl$_3$), 135.31, 132.56, 132.5, 131.49, 131.27, 118.74, 80.54, 79.25, 76.45, 55.03, 38.52, 38.29, 37.06, 36.85, 36.75, 36.67, 35.32, 26.64 (3C), 26.58 (3C), 23.89, 18.90, 18.81, 17.91, 17.65, 13.83, 9.97, 9.92, −2.87, −3.09, −3.26, −3.46; HRMS: ESI m/z 610.5070 (M+H$^+$), Cal. 610.5051.

b) Preparation of N-[(2S,3R,4S,5Z,8S,9R,10R,11S,12S,13Z)-3,9-bis[[(1,1-dimethylethyl)dimethylsilyl]oxy]-11-hydroxy-2,4,6,8,10,12-hexamethyl-5,13,15-hexadecatrienyl]-N-methyl-cyclohexaneacetamide.

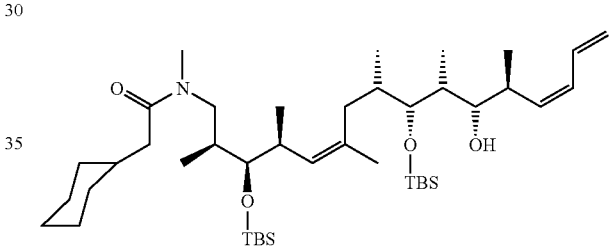

A DMF (2 mL) solution of cyclohexaneacetic acid (30.2 mg, 0.222 mmol) and BOP (131 mg, 0.296 mmol) is added to the stirred DMF (3 mL) solution of (3Z,5S,6S,7R,8R,9S,11Z,13S,14R,15S)-8,14-bis[[(1,1-dimethylethyl)dimethylsilyl]oxy]-5,7,9,11,13,15-hexamethyl-16-(methylamino)-1,3,11-hexadecatrien-6-ol (90 mg, 0.148 mmol) and DIEA (77 μL, 0.444 mmol) dropwise at 0° C. The solution is warmed up to 23° C. and stirred for an additional 1 hour. DMF is removed in vacuo and the residue is dissolved in EtOAc (10 mL). The organic solution is washed with H$_2$O (1×10 mL) and brine (1×10 mL). The aqueous layer is extracted with Et$_2$O (3×20 mL) and the combined extracts are dried (Na$_2$SO$_4$) and concentrated. Chromatography (SiO$_2$, 0–30% EtOAc-hexanes gradient elution) provided the desired compound (70 mg, 65%). HRMS: ESI m/z 734.5906 (M+H$^+$), Calcd. 734.5939.

$^1$H NMR (300 MHz, CDCl$_3$), δ 6.62 (ddd, J=16.7, 10.9, 10.5 Hz, 1H), 6.14 (t, J=10.9 Hz, 1H), 5.32 (t, J=10.2 Hz, 1H), 5.24 (d, J=16.9, Hz, 1H), 5.15 (d, J=9.8 Hz, 1H), 5.02 (d, J=10.2 Hz, 1H), 3.63 (m, 1H), 3.32 (m, 2H), 2.81 (m, 1H), 2.80 (s, 3H), 2.61 (m, 1H), 2.52 (m, 1H), 2.37 (m, 1H), 2.20 (m, 1H), 2.03 (d, J=5.3 Hz, 1H), 1.65–1.95 (m, 9H); 1.59 (m, 4H), 1.15 (m, 5H), 1.05 (m, 2H), 1.00–0.94 (m, 9H), 0.93 (s, 9H), 0.90 (s, 9H), 0.74 (d, J=6.7, 3H), 0.10–0.00 (m, 12H); $^{13}$C NMR (75 MHz, CDCl$_3$), 173.09, 134.79, 133.13, 132.23, 131.43, 130.29, 118.47, 80.64, 78.81, 76.04, 50.69, 40.99, 38.58, 37.30, 37.12, 36.54, 36.51, 36.29, 35.47, 34.53, 33.72, 33.59, 33.25, 33.20, 26.45

(6C), 23.42, 19.42, 18.73, 18.70, 17.37, 15.33, 13.24, 9.91, 9.78, −2.93, −3.08, −3.15, −3.39.

c) Preparation of N-[(2S,3R,4S,5Z,8S,9R,10R,11S,12S, 13Z)-11-[(aminocarbonyl)oxy]-3,9-bis[[(1,1-dimethylethyl) dimethylsilyl]oxy]-2,4,6,8,10,12-hexamethyl-5,13,15-hexadecatrienyl]-N-methyl-cyclohexaneacetamide.

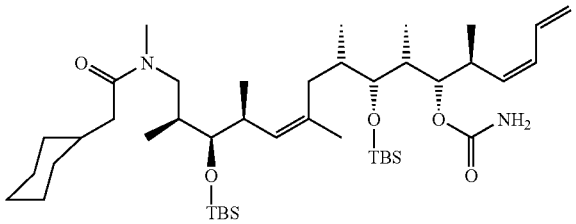

A solution of N-[(2S,3R,4S,5Z,8S,9R,10R,11S,12S,13Z)-3,9-bis[[(1,1-dimethylethyl)dimethylsilyl]oxy]-11-hydroxy-2,4,6,8,10,12-hexamethyl-5,13,15-hexadecatrienyl]-N-methyl-cyclohexaneacetamide (70 mg, 0.096 mmol, 1 eq) in CH$_2$Cl$_2$ (2.0 mL) is treated with trichloroacetyl isocyanate (27.2 g, 0.145 mmol, 1.5 eq) at 23° C. (20 minutes). The solution is concentrated, and the residue dissolved in CH$_3$OH (2.0 mL). To this solution is added K$_2$CO$_3$ (10 mg) and the mixture is stirred at 23° C. (2 hours). The reaction mixture is concentrated and the residue dissolved in Et$_2$O (10 mL). The organic solution is filtered through Celite and concentrated. Chromatography (SiO$_2$, 0–30% EtOAc-hexanes gradient elution) provided the desired compound (70 mg, 94%): HRMS ESI m/z 777.5984 (M+H$^+$, $C_{44}H_{85}O_5N_2Si_2$ requires 777.5997).

$^1$H NMR (300 MHz, CDCl$_3$), δ 6.58 (ddd, J=16.7, 10.9, 10.5 Hz, 1H), 5.99 (t, J=10.9 Hz, 1H), 5.35 (t, J=10.2 Hz, 1H), 5.21 (d, J=16.9, Hz, 1H), 5.13 (d, J=9.8 Hz, 1H), 4.93 (d, J=10.6 Hz, 1H), 4.66 (br, 2H), 3.40 (m, 1H), 3.32 (m, 1H), 3.02 (m, 1H), 2.81 (m, 1H), 2.76 (s, 3H), 2.61 (m, 1H), 2.52 (m, 1H), 2.37 (m, 1H), 2.20 (m, 1H), 2.03 (d, J=5.3 Hz, 1H), 1.65–1.95 (m, 9H), 1.59 (m, 4H), 1.15 (m, 5H), 1.05 (m, 2H), 1.00–0.94 (m, 9H), 0.93 (s, 9H), 0.90 (s, 9H), 0.74 (d, J=6.7 Hz, 3H), 0.10–0.00 (m, 12H); $^{13}$C NMR (75.5 MHz, CDCl$_3$), 173.04, 157.15, 133.86, 133.00, 132.23, 130.11, 129.83, 118.16, 80.58, 78.57, 77.16, 50.50, 40.92, 38.28, 37.03, 36.97, 36.14, 35.38, 34.75, 34.54, 33.63, 33.54, 33.11, 26.49, 26.38 (6C), 23.13, 19.24, 18.71, 18.68, 18.62, 18.58, 17.59, 15.23, 13.66, 10.26, −3.22, −3.26, −3.44, −3.61.

d) Preparation of N-[(5Z,8S,9R,10S,11S,12S,13Z)-11-(2-amino-2-oxoethyl)-3,9-dihydroxy-2,4,6,8,10,12-hexamethyl-5,13,15-hexadecatrienyl]-N-methyl-cyclohexaneacetamide.

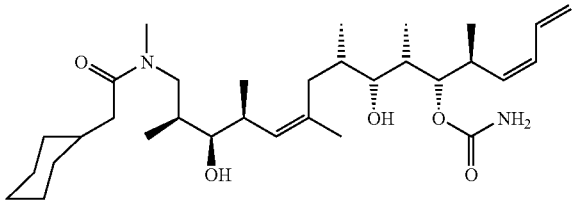

To a solution of N-[(2S,3R,4S,5Z,8S,9R,10R,11S,12S, 13Z)-11-[(aminocarbonyl)oxy]-3,9-bis[[(1,1-dimethylethyl) dimethylsilyl]oxy]-2,4,6,8,10,12-hexamethyl-5,13,15-hexadecatrienyl]-N-methyl-cyclohexaneacetamide (70 mg, 0.452 mmol, 1 eq) in MeOH (10 mL) is added a MeOH solution of HCl (15.5 mL, 15 mL MeOH+0.5 mL 12N HCl). The resulting solution is stirred at 23° C. (36 hours). The pH is adjusted to 8 by the addition of solid NaHCO$_3$ at 0° C.

The solution is concentrated, and the residue dissolved in CH$_2$Cl$_2$ (10 mL) and filtered through Celite. Chromatography (SiO$_2$, 50% CH$_2$Cl$_2$-EtOAc, then 100% EtOAc) provided the desired compound (48 mg, 80%) as a white solid: [α]$^{25}_D$+35.93° (c 1.88, CH$_2$Cl$_2$).

$^1$H NMR (500 MHz, CDCl$_3$), δ 6.62 (ddd, J=15.9, 10.7, 10.4 Hz, 1H), 6.02 (t, J=10.8 Hz, 1H), 5.36 (t, J=10.4 Hz, 1H), 5.22 (d, J=7.0, 1H), 5.20 (d, J=15.1 Hz, 1H), 5.10 (d, J=10.1, Hz, 1H), 4.72 (m, 3H), 3.91 (br, 1H), 3.74 (dd, J=14.0, 5.6 Hz, 1H), 3.3 (m, 2H), 3.15 (dd, J=14.1, 4.9 Hz, 1H), 3.01 (s, 3H), 2.99 (m, 1H), 2.55 (m, 1H), 2.31 (br s, 1H), 2.20 (dd, J=6.8, 3.3 Hz, 1H), 2.01–1.60 (m, 15H), 1.26 (m, 3H), 1.14 (m, 1H), 1.02–0.8 (m, 18H); $^{13}$C NMR (125 MHz, CDCl$_3$), δ 174.0, 157.0, 134.17, 133.91, 133.88, 132.53, 132.14, 130.55, 129.78, 117.76, 78.53, 76.45, 75.46, 51.18, 41.11, 38.00, 37.26, 36.17, 36.08, 34.80, 34.66, 33.39, 33.38, 32.86, 26.25, 26.11, 23.30, 17.38, 16.12, 15.34, 13.64, 8.98; HRMS ESI m/z 549.4282 (M+H$^+$), Cal. 549.4267.

EXAMPLE 6

Synthesis of (2S,3Z,5S,6S,7S,8Z,11S,12R,13R,14S, 15S,16Z)-1-cyclopentyl-5,7,9,11,13,15-hexamethyl-3,8,16,18-nonadecatetraene-2,6,12,14-tetrol-14-carbamate a) Preparation of (3-cyclopentyl-2-oxopropyl)-bis(2,2,2-trifluoroethyl)phosphonic acid ester.

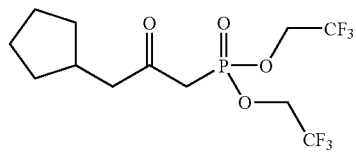

Hexamethyldisilazane (13.24 mL, 62.74 mmol, 2.3 eq) is added to a solution of n-BuLi (37.5 mL, 60 mmol, 1.6 M, 2.2 eq) and THF (50 mL) dropwise at −20° C. over 5 minutes. The solution is warmed to 0° C. and is stirred for 20 minutes. The solution is then cooled to −100° C. and a pre-cooled (−78° C.) THF (20 mL) solution of cyclopentylacetyl chloride (4 g, 27.28 mmol, 1 eq) and bis(2,2,2-trifluoroethyl) methylphosphonate (7.09 g, 27.28 mmol, 1 eq) is added dropwise over 10 minutes. The reaction mixture is stirred at −100° C. an additional 20 minutes and stored overnight at −30° C. The cold reaction mixture is poured into a stirred mixture of 50 mL of 2N HCl and an equal volume of ice, and 100 mL of CH$_2$Cl$_2$. The organic layer is separated and the aqueous layer extracted with CH$_2$Cl$_2$ (2×20 mL). The organic extracts are combined, dried (Na$_2$SO$_4$) and concentrated to an oil. Chromatography (SiO$_2$, 5% EtOAc-hexane) provides (3-cyclopentyl-2-oxopropyl)-bis(2,2,2-trifluoroethyl)phosphonic acid ester (4.03 g, 40%) as a colorless oil.

$^1$H NMR (300 MHz, CDCl$_3$), δ 4.26 (m, 4H), 3.18 (d, J=21.5 Hz, 2H), 3.07 (d, J=7.1 Hz, 2H), 2.04 (m, 1H), 1.65 (m, 9H), 1.40 (m, 4H), 0.90 (m, 2H).

b) Preparation of (3Z,5S,6S,7S,8Z,11S,12R,13R,14S,15S,16Z)-1-cyclopentyl-6,12-bis[[(1,1-dimethylethyl)dimethylsilyl]oxy]-14-hydroxy-5,7,9,11,13,15-hexamethyl-3,8,16,18-nonadecatetraen-2-one.

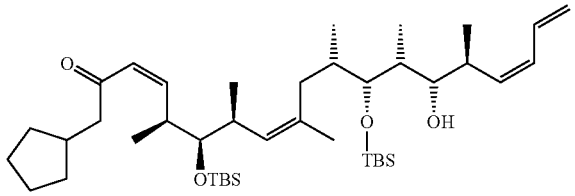

To a –20° C. solution of (3-cyclopentyl-2-oxopropyl)-bis(2,2,2-trifluoroethyl)phosphonic acid ester (0.654 g, 1.768 mmol, 2.1 eq) and 18-Crown-6 (0.445 g, 1.684 mmol, 2 eq) in toluene (10 mL) is added KHMDS (3.54 mL, 0.5 M in tol, 1.768 mmol, 2.1 eq) over 2 minutes. The solution is warmed to 0° C. (10 minutes) and re-cooled to –20° C. To this solution a toluene solution of (2R,3R,4S,5Z,8S,9R,10R,11S,12S,13Z)-3,9-bis[[(1,1-dimethylethyl)dimethylsilyl]oxy]-11-hydroxy-2,4,6,8,10,12-hexamethyl-5,13,15-hexadecatrienal (0.5 g, 0.842 mmol, 1 eq) is added dropwise. The solution is stirred at 0° C. (3 hours), quenched with saturated NH$_4$Cl (10 mL) and the aqueous layer extracted with EtOAc (3×10 mL). The organic extracts are combined, dried (MgSO$_4$) and concentrated to an oil. Chromatography (SiO$_2$, 10% EtOAc-hexane) provides (3Z,5S,6S,7S,8Z,11S,12R,13R,14S,15S,16Z)-1-cyclopentyl-6,12-bis[[(1,1-dimethylethyl)dimethylsilyl]oxy]-14-hydroxy-5,7,9,11,13,15-hexamethyl-3,8,16,18-nonadecatetraen-2-one (0.32 g, 54%) as a colorless oil.

$^1$H NMR (300 MHz, CDCl$_3$), δ 6.63 (ddd, J=16.7, 10.8, 10.6 Hz, 1H), 6.25–6.04 (m, 3H), 5.34 (t, J=10.4 Hz, 1H), 5.25 (d, J=16.8 Hz, 1H), 5.16 (d, J=10.2 Hz, 1H), 4.92 (d, J=10.2 Hz, 1H), 3.60 (m, 2H), 3.36 (m, 2H), 2.82 (m, 1H), 2.57–2.49 (m, 1H), 2.44 (t, J=7.1 Hz, 1H), 2.39–2.34 (m, 1H), 2.26–2.10 (m, 3H), 1.89–1.73 (m, 3H), 1.69–1.49 (m, 4H), 1.57 (s, 3H), 1.27 (d, J=2.8 Hz, 1H), 1.15–1.08 (m, 2H), 1.00 (d, J=6.0 Hz, 3H), 0.98 (d, J=6.8 Hz, 3H), 0.99 (d, J=7.1 Hz, 3H), 0.96–0.90 (s, 18H), 0.89 (d, J=2.9 Hz, 3H), 0.71 (d, J=6.7 Hz, 3H), 0.10–0.01 (m, 12H); $^{13}$C NMR (75 MHz, CDCl$_3$), δ 201.05, 150.59, 134.80, 132.77, 132.23, 131.13, 130.67, 125.85, 118.61, 80.78, 78.90, 76.53, 50.72, 38.15, 37.86, 36.40, 36.30, 35.96, 35.00, 32.81, 32.77, 26.38 (6C), 25.11, 23.28, 18.63, 18.20, 18.15, 17.42, 13.78, 9.61, –3.22, –3.26, –3.36, –3.55; HRMS ESI m/z 703.5664 (M+H$^+$, C$_{42}$H$_{79}$O$_4$Si$_2$ requires 704.2675).

c) Preparation of (3Z,5S,6S,7S,8Z,11S,12R,13R,14S,15S,16Z)-14-[(aminocarbonyl)oxy]-1-cyclopentyl-6,12-bis[[(1,1-dimethylethyl)dimethylsilyl]oxy]-5,7,9,11,13,15-hexamethyl-3,8,16,18-nonadecatetraen-2-one.

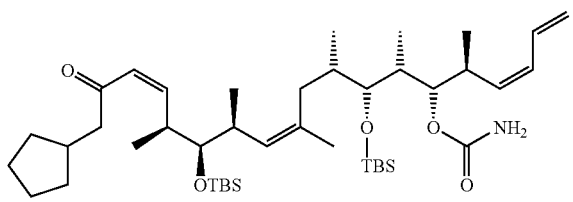

A solution of (3Z,5S,6S,7S,8Z,11S,12R,13R,14S,15S,16Z)-1-cyclopentyl-6,12-bis[[(1,1-dimethylethyl)dimethylsilyl]oxy]-14-hydroxy-5,7,9,11,13,15-hexamethyl-3,8,16,18-nonadecatetraen-2-one (420 mg, 0.60 mmol, 1 eq) in CH$_2$Cl$_2$ (10 mL) is treated with trichloroacetyl isocyanate (135 mg, 0.72 mmol, 1.2 eq) at 23° C. (20 minutes). The solution is concentrated, and the residue dissolved in CH$_3$OH (10 mL). To this solution is added K$_2$CO$_3$ (0.2 g) and the mixture is stirred at 23° C. (3 hours). The reaction mixture is concentrated and the residue dissolved in Et$_2$O (20 mL). The organic solution is washed with H$_2$O (1×10 mL) and brine (1×20 mL). The aqueous layer is extracted with Et$_2$O (3×10 mL) and the combined extracts are dried (Na$_2$SO$_4$) and concentrated. Chromatography (SiO$_2$, 30–50% EtOAc-hexanes gradient elution) provides (3Z,5S,6S,7S,8Z,11S,12R,13R,14S,15S,16Z)-14-[(aminocarbonyl)oxy]-1-cyclopentyl-6,12-bis[[(1,1-dimethylethyl)dimethylsilyl]oxy]-5,7,9,11,13,15-hexamethyl-3,8,16,18-nonadecatetraen-2-one (420 mg, 94%).

$^1$H NMR (300 MHz, CDCl$_3$), δ 6.61 (ddd, J=16.7, 10.8, 10.6 Hz, 1H), 6.19 (t, J=11.7 Hz, 1H), 6.03 (m, 2H), 5.39 (t, J=10.1 Hz, 1H), 5.25 (d, J=16.6 Hz, 1H), 5.15 (d, J=9.8 Hz, 1H), 4.90 (d, J=10.1 Hz, 1H), 4.57 (br, 2H), H), 3.60 (m, 1H), 3.42 (t, J=4.1 Hz, 1H), 3.36 (m, 1H), 3.00 (m, 1H), 2.43 (t, J=6.7 Hz, 1H), 2.39–2.34 (m, 1H), 2.26–2.10 (m, 3H), 1.89–1.73 (m, 3H), 1.69–1.49 (m, 4H), 1.56 (s, 3H), 1.27 (br, 1H), 1.15-1.08 (m, 2H), 1.01 (m, 6H), 0.98 (d, J=6.8 Hz, 3H), 0.99 (d, J=7.1 Hz, 3H), 0.96–0.90 (s, 18H), 0.89 (d, J=2.9 Hz, 3H), 0.71 (d, J=6.7 Hz, 3H), 0.10–0.01 (m, 12H); $^{13}$C NMR (75 MHz, CDCl$_3$), δ 201.04, 157.16, 150.66, 133.64, 132.66, 132.22, 130.63, 130.12, 125.84, 118.23, 80.67, 79.08, 76.97, 50.74, 38.03, 37.94, 37.77, 35.99, 35.41, 34.55, 32.84, 32.81, 26.40 (6C), 25.15, 23.04, 18.71, 18.65, 18.24, 18.07, 17.73, 14.24, 10.27, –3.26, –3.55; HRMS ESI m/z 746.5551 (M+H$^+$, C$_{43}$H$_{80}$O$_5$NSi$_2$ requires 746.5575).

d) Preparation of (2S,3Z,5S,6S,7S,8Z,11S,12R,13R,14S,15S,16Z)-1-cyclopentyl-6,12-bis[[(1,1-dimethylethyl)dimethylsilyl]oxy]-5,7,9,11,13,15-hexamethyl-3,8,16,18-nonadecatetraene-2,14-diol-14-carbamate.

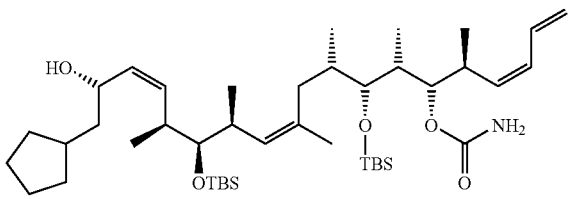

To a solution of (3Z,5S,6S,7S,8Z,11S,12R,13R,14S,15S,16Z)-14-[(aminocarbonyl)oxy]-1-cyclopentyl-6,12-bis[[(1,1-dimethylethyl)dimethylsilyl]oxy]-5,7,9,11,13,15-hexamethyl-3,8,16,18-nonadecatetraen-2-one (190 mg, 0.255 mmol, 1 eq) in toluene (2.0 mL) is treated with (R)-1-butyltetrahydro-3,3-diphenyl-1H,3H-pyrrolo[1,2-c][1,3,2]oxazaborole (1.27 mL, 0.255 mmol, 1.0 eq) and catecholborane (215 mg, 1.79 mmol, 7 eq) at –78° C. (20 minutes). After the solution is warmed to –20° C. for 3 hours, CH$_2$Cl$_2$ (5 mL) and 1 N HCl (5 mL) are added at 0° C., then stirred for another 30 minutes at rt. The organic solution is washed with Na$_2$CO$_3$ (1×5 mL) and brine (1×10 mL), dried (Na$_2$SO$_4$) and concentrated. Chromatography (SiO$_2$, 30–50% EtOAc-hexanes gradient elution) provides (2S,3Z,5S,6S,7S,8Z,11S,12R,13R,14S,15S,16Z)-1-cyclopentyl-6,12-bis[[(1,1-dimethylethyl)dimethylsilyl]oxy]-5,7,9,11,13,15-hexamethyl-3,8,16,18-nonadecatetraene-2,14-diol-14-carbamate (100 mg, 53%).

$^1$H NMR (300 MHz, CDCl$_3$), δ 6.61 (ddd, J=16.7, 10.8, 10.6 Hz, 1H), 6.04 (t, J=10.6 Hz, 1H), 5.53 (m, 2H), 5.38 (m, 2H), 5.23 (d, J=16.9 Hz, 1H), 5.14 (d, J=10.2 Hz, 1H), 5.10 (d, J=10.2 Hz, 1H), 4.75 (t, J=6.1 Hz, 1H), 4.52 (br, 2H), 4.32 (m, 1H), 3.42 (t, J=4.6 Hz, 1H), 3.29 (m, 1H), 3.0 (m, 1H), 2.72 (m, 1H), 2.42 (m, 1H), 2.05 (t, J=7.1 Hz, 1H), 1.95–1.73 (m, 3H), 1.62 (s, 3H), 1.60–1.52 (m, 2H), 1.41 (m, 1H), 1.12 (m, 1H), 1.01 (d, J=3.0 Hz, 3H), 0.93 (s, 9H), 0.92 (s, 9H), 0.93–0.88 (m, 9H), 0.72 (d, J=6.4 Hz, 3H), 0.11–0.04 (m, 12H); $^{13}$C NMR (125 MHz, MeOD$_3$), δ 157.5, 1345.5, 133.8, 132.5, 131.6, 130.3, 121.1, 118.4, 115.7, 80.9, 79.3, 77.3, 68.0, 44.4, 38.3, 37.5, 36.8, 36.6, 35.4, 34.8, 33.7, 32.9 26.6 (18H), 25.5, 23.3, 19.6, 18.9, 17.8, 17.5, 14.3, 10.4, −2.7, −3.0, −3.5; HRMS ESI m/z 770.5456 (M+Na$^+$, C$_{43}$H$_{81}$O$_5$NSi$_2$ requires 770.5551).

e) Preparation of (2S,3Z,5S,6S,7S,8Z,11S,12R,13R,14S, 15S,16Z)-1-cyclopentyl-5,7,9,11,13,15-hexamethyl-3,8,16, 18-nonadecatetraene-2,6,12,14-tetrol-14-carbamate.

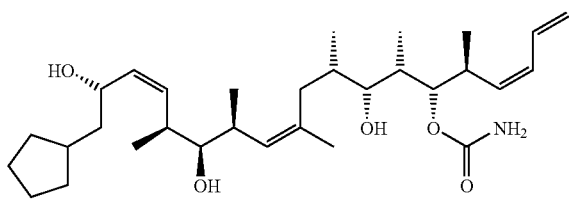

To a solution of (2S,3Z,5S,6S,7S,8Z,11S,12R,13R,14S, 15S,16Z)-1-cyclopentyl-6,12-bis[[(1,1-dimethylethyl)dimethylsilyl]oxy]-5,7,9,11,13,15-hexamethyl-3,8,16,18-nonadecatetraene-2,14-diol-14-carbamate (500 mg, 0.67 mmol) in MeOH (120 mL) is treated with 4N HCl (20 mL) at rt over 20 minutes. After the solution is stirred for 16 hours, EtOAc (200 mL) and Na$_2$CO$_3$ are added at 0° C. to pH=7. The organic solution is dried (Na$_2$SO$_4$) and concentrated. HPLC purification (symmetry C18, 30–95% H$_2$O-MeCN gradient elution) provides (2S,3Z,5S,6S,7S,8Z,11S,12R,13R,14S, 15S,16Z)-1-cyclopentyl-5,7,9,11,13,15-hexamethyl-3,8,16, 18-nonadecatetraene-2,6,12,14-tetrol-14-carbamate (158 mg, 45%): [α] +35.808 C=1.4/MeOH.

$^1$H NMR (500 MHz, MeOD$_3$), δ 6.69 (ddd, J=16.7, 10.8, 10.6 Hz, 1H), 6.03 (t, J=11.2 Hz, 1H), 5.44 (t, J=10.6 Hz, 1H), 5.38 (d, J=8.4 Hz, 2H), 5.21 (d, J=16.8 Hz, 1H), 5.12 (d, J=10.0 Hz, 2H), 4.77 (t, J=6.6 Hz, 1H), 4.57 (br, 2H), 4.31 (m, 1H), 3.23 (t, J=6.0 Hz, 1H), 3.16 (m, 1H), 3.09 (t, J=5.7 Hz, 1H), 2.62 (m, 1H), 2.50 (m, 1H), 2.00 (t, J=12.6 Hz, 1H), 1.89–1.73 (m, 3H), 1.65 (s, 3H), 1.60–1.52 (m, 2H), 1.36 (m, 1H), 1.12 (m, 1H), 0.99 (d, J=6.8 Hz, 3H), 0.97 (d, J=3.7 Hz, 3H), 0.96 (d, J=3.6 Hz, 3H), 0.93 (d, J=6.6 Hz, 3H), 0.79 (d, J=6.6 Hz, 3H); $^{13}$C NMR (125 MHz, MeOD$_3$), δ 160.2, 134.6, 134.6, 134.2, 134.2, 133.5, 131.8, 130.8, 118.2, 80.3, 79.5, 77.0, 68.0, 45.4, 38.8, 37.6, 37.0, 36.5, 35.4, 34.4, 34.1, 33.7, 26.0, 25.9, 23.5, 19.1, 18.1, 16.0, 14.5, 9.7; HRMS ESI m/z 520.4008 (M+H$^+$, C$_{31}$H$_{54}$O$_5$N requires 520.4002).

EXAMPLE 7

Synthesis of (2S,3Z,5S,6S,7S,8Z,11S,12R,13R,14S, 15S,16Z)-1-isopropyl-5,7,9,11,13,15-hexamethyl-3, 8,16,18-nonadecatetraene-2,6,12,14-tetrol-14-carbamate

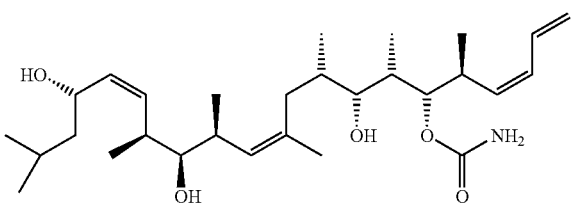

(2S,3Z,5S,6S,7S,8Z,11S,12R,13R,14S,15S,16Z)-1-isopropyl-5,7,9,11,13,15-hexamethyl-3,8,16,18-nonadecatetraene-2,6,12,14-tetrol-14-carbamate is prepared in the same manner as described for 2S,3Z,5S,6S,7S,8Z,11S,12R,13R, 14S,15S,16Z)-1-cyclopentyl-5,7,9,11,13,15-hexamethyl-3, 8,16,18-nonadecatetraene-2,6,12,14-tetrol-14-carbamate in Example 6 with the exception that instead of using (3-cyclopentyl-2-oxopropyl)-bis(2,2,2-trifluoroethyl)phosphonic acid ester, (3-isopropyl-2-oxopropyl)-bis(2,2,2-trifluoroethyl)phosphonic acid ester was utilized.

$^1$H NMR (300 MHz, CDCl$_3$), δ 6.62 (ddd, J=16.7, 10.8, 10.6 Hz, 1H), 6.04 (t, J=11.0 Hz, 1H), 5.53–5.32 (m, 3H), 5.23 (d, J=15 Hz, 1H), 5.18 (d, J=9.1 Hz, 1H), 5.13 (d, J=10.2 Hz, 1H), 4.74 (dd, J=6.8, 4.9 Hz, 1H), 4.61 (br, 2H), 4.45 (m, 1H), 3.29 (t, J=5.3 Hz, 1H), 3.20 (dd, J=5.8, 4.9 Hz, 1H), 3.01 (m, 1H), 2.77 (m, 1H), 2.59 (m, 1H), 1.94–1.73 (m, 5H), 1.64 (s, 3H), 1.51 (m, 1H), 1.25 (m, 1H), 1.03 (d, J=6.7 Hz, 3H), 1.01 (d, J=7.1 Hz, 3H), 0.98 (d, J=7.2 Hz, 3H), 0.95 (d, J=6.6 Hz, 3H), 0.95 (s, 3H), 0.93 (s, 1H), 0.84 (d, J=6.0 Hz, 3H); $^{13}$C NMR (75 MHz, CDCl$_3$), δ 157.3, 134.4, 134.0, 133.7, 133.5, 132.3, 130.1, 129.9, 118.2, 79.2, 79.0, 76.2, 66.6, 47.0, 37.3, 35.9, 35.8. 35.1, 34.9, 33.3, 24.6, 23.8, 23.7, 23.4, 22.3, 18.7, 17.6, 15.6, 14.3, 8.8; HRMS ESI m/z 516.3654 (M+Na$^+$, C$_{29}$H$_{51}$O$_5$NNa requires 516.3665).

Following are the corresponding structures of the compounds of Examples 1–7:

EXAMPLE 1

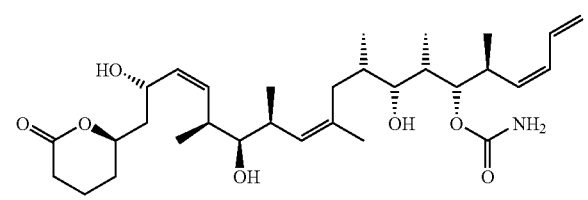

EXAMPLE 2

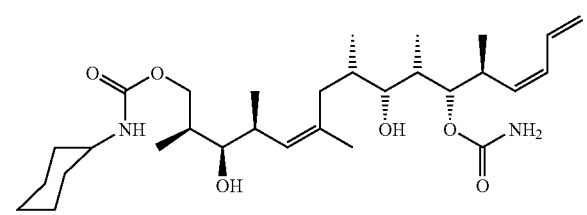

-continued

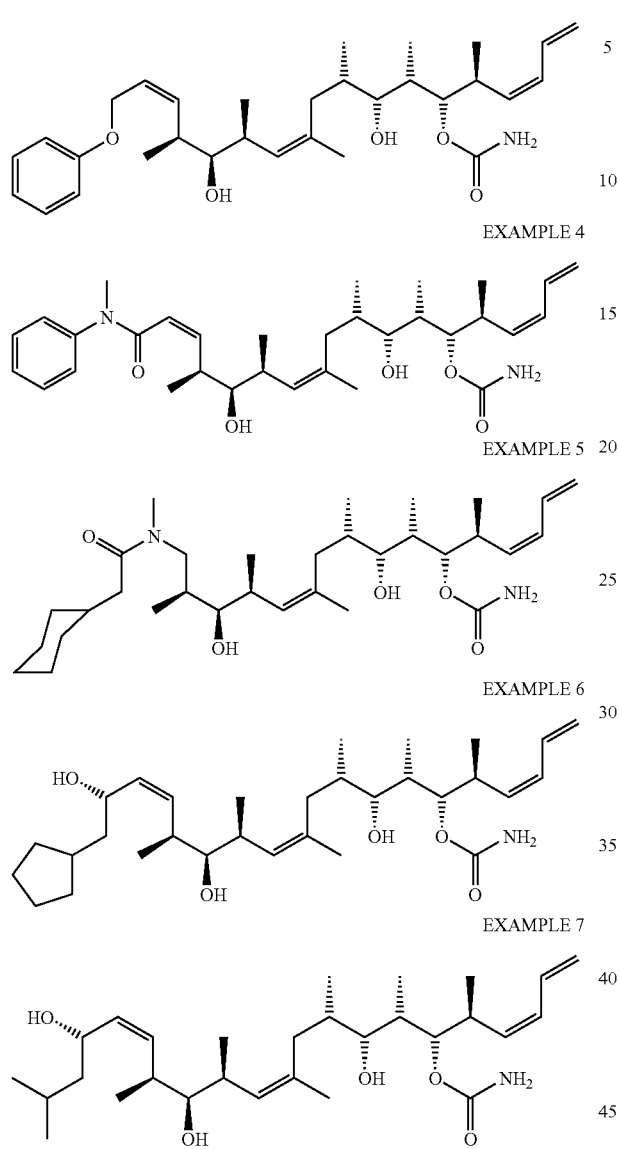

EXAMPLE 3

EXAMPLE 4

EXAMPLE 5

EXAMPLE 6

EXAMPLE 7

What is claimed is:
1. A compound of formula I

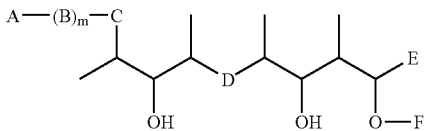

I

A is $(C_{1-6})$alkyl or $(C_{1-6})$hydroxyalkyl;
B is —$CH_2CH(OR_1)$—;
C is —$C(R_4)$=$C(R_4)$—;
D is —CH=$C(R_4)CH_2$—;
E is —$CH(R_4)CH$=$CHCH$=$CH_2$;
F is H, —$C(O)N(R_1)_2$, —$C(O)NHCH_2(CH_2)_nN(CH_3)_2$, or —$C(O)NHCH_2(CH_2)_n$-4-morpholino;
$R_1$ is H, $(C_{1-6})$alkyl, $(C_{1-6})$alkyl-Ar or Ar;

Ar is an aromatic or heteroaromatic ring selected from

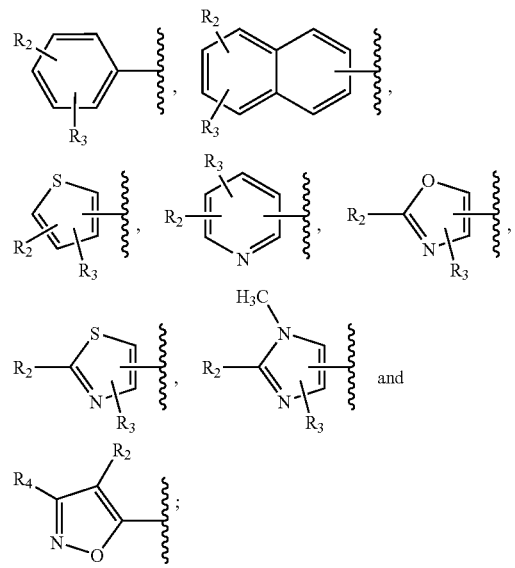

$R_2$ and $R_3$ are, independently, H, $(C_{1-6})$alkyl, OH, O$(C_{1-6})$alkyl, $OCH_2(CH_2)_n$OH, $O(CH_2)_nCO_2H$, $OCH_2(CH_2)_nN(CH_3)_2$, $OCH_2(CH_2)_n$-4-morpholino, F, Cl, Br or $CF_3$;
$R_4$ is H or $(C_{1-6})$alkyl;
$R_5$ is $(C_{1-6})$alkyl, $(C_{1-6})$alkyl-Ar or Ar;
m is 0 or 1;
n is 1 or 2; and
q is 0–6;
with the proviso that when A is Ar or

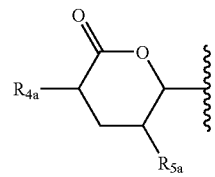

where each of $R_{4a}$ and $R_{5a}$ is $(C_{1-6})$alkyl,
then either:
B cannot be —$CH_2CH(OH)$— or —$CH_2C(O)$—,
or C cannot be —CH=CH—,
or D cannot be —CH=$C(CH_3)CH_2$—,
or E cannot be —$CH(CH_3)CH$=CHCH=$CH_2$,
or F cannot be —$C(O)NH_2$,
and with the provisos that when A is

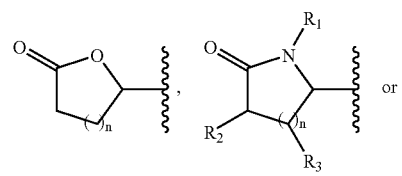

-continued

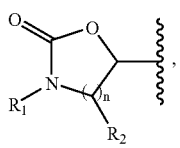

then B cannot be —OCH(R$_4$)— or —N(R$_1$)C(O)—,
and when B is —CH$_2$CH(OH)— or —OCH(R$_4$)—,
then C cannot be —OCH(R$_4$)—, —N(R$_1$)CH$_2$— or —N(R$_1$)C(O)—,
and with the further proviso that the compound of formula I is not a compound of formulae

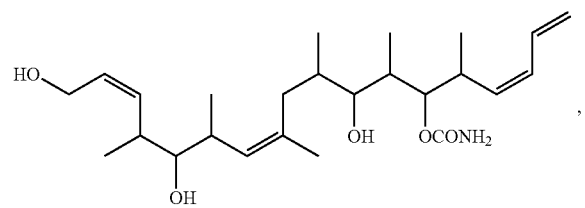

,

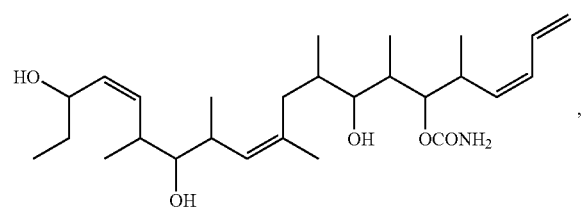

,

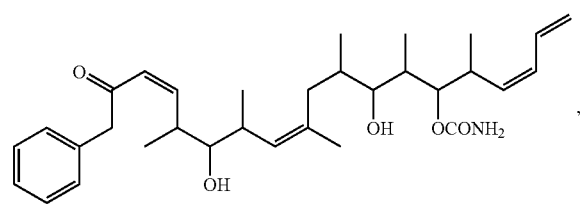

,

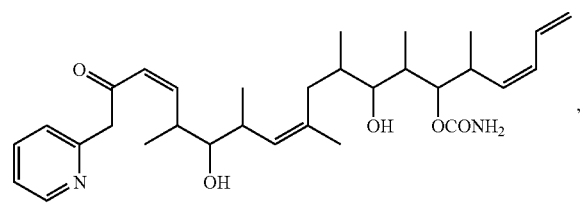

,

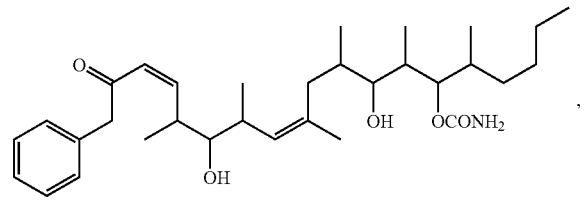

,

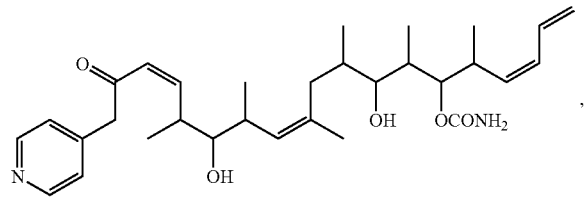

,

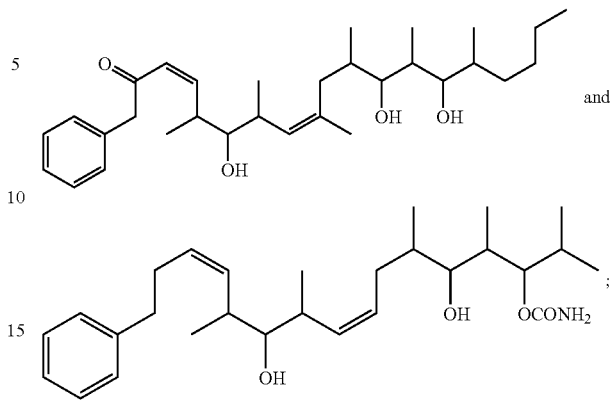

or an acid or base addition salt thereof, where possible.

2. A compound according to claim 1 of formula Ia

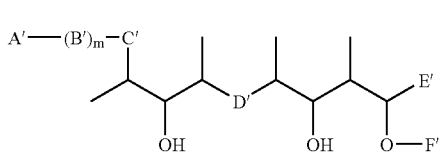

A' is (C$_{1-6}$)alkyl;
B' is —CH$_2$CH(OR$_{1'}$);
C' is —CH=CH—;
E' is CH(R$_{4'}$)CH=CHCH=CH$_2$;
F' is H, —C(O)N(R$_{1'}$)$_2$, —C(O)NHCH$_2$(CH$_2$)$_n$N(CH$_3$)$_2$ or —C(O)NHCH$_2$(CH$_2$)$_n$-4-morpholino;
R$_{1'}$ is H, (C$_{1-3}$)alkyl, (C$_{1-3}$)alkyl-Ar' or Ar';
Ar' is selected from

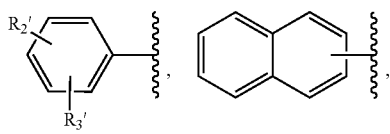

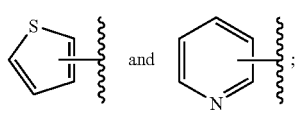

;

R$_2$' and R$_3$' are, independently, H, (C$_{1-6}$)alkyl, OH, O(C$_{1-3}$)alkyl, OCH$_2$(CH$_2$)$_n$OH, O(CH$_2$)$_n$CO$_2$H, OCH$_2$(CH$_2$)$_n$N(CH$_3$)$_2$, OCH$_2$(CH$_2$)$_n$-4-morpholino, F, Cl, Br or CF$_3$;
R$_{4'}$ is H or (C$_{1-3}$)alkyl;
R$_{5'}$ is (C$_{1-6}$)alkyl, (C$_{1-3}$)alkyl-Ar' or Ar';
m is 0 or 1; and
n is 1 or 2;
with the proviso that when A' is Ar' or

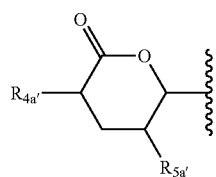

where $R_{4a'}$ is $(C_{1-3})$alkyl and $R_{5a'}$ is $(C_{1-6})$alkyl, then either:

B' cannot be —CH$_2$CH(OH)— or —CH$_2$C(O)—,
or C' cannot be —CH=CH—,
or D' cannot be —CH=C(CH$_3$)CH$_2$—,
or E' cannot be —CH(CH$_3$)CH=CHCH=CH$_2$,
or F' cannot be —C(O)NH$_2$,
and with the provisos that when A' is

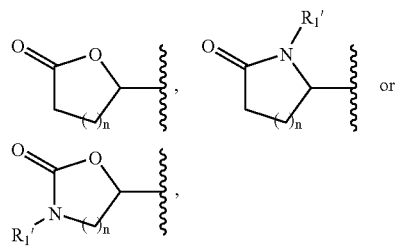

then B' cannot be —OCH$_2$— or —N(R$_1$')C(O)—,
and when B' is —CH$_2$CH(OH)— or —OCH$_2$—,
then C' cannot be —OCH$_2$—, —N(R$_1$')CH$_2$— or —N(R$_1$')C(O)—,
and with the further proviso that the compound of formula Ia is not a compound of formulae

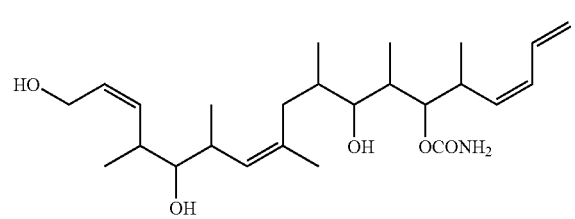

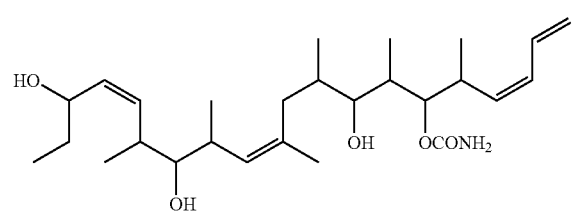

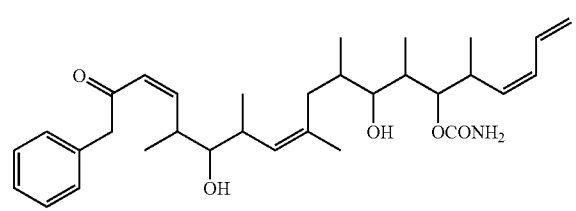

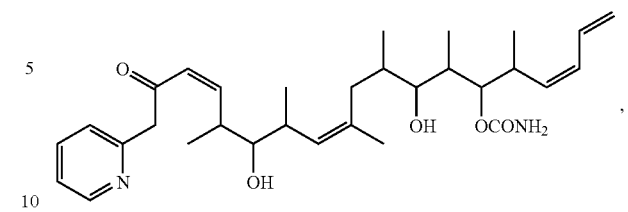

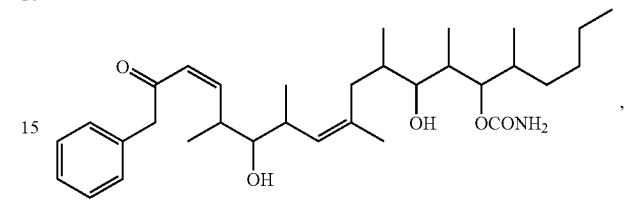

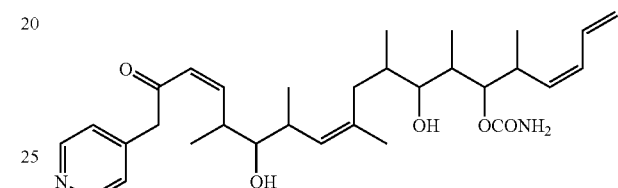

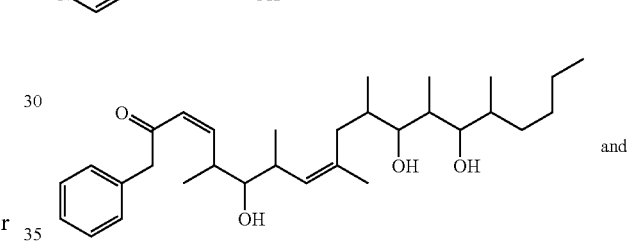

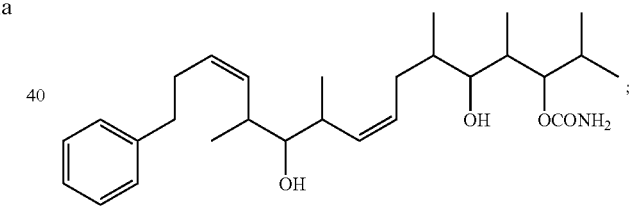

or an acid or base addition salt thereof, where possible.

3. A compound according to claim 2 of formula Ib

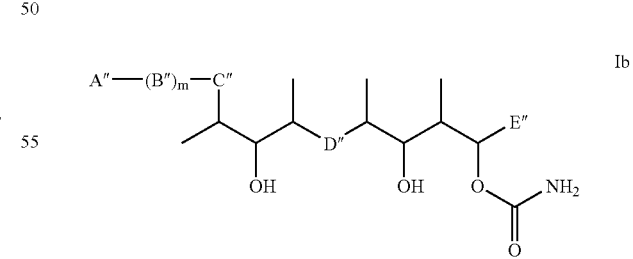

A" is $(C_{1-6})$alkyl;
B" is —CH$_2$CH(OR$_{1''}$)—;
C" is —CH=CH—;
E" is —CH(R$_{4''}$)CH=CHCH=CH$_2$;
R$_{1''}$ is H, $(C_{1-3})$alkyl, CH$_2$—Ar" or Ar";

Ar" is selected from

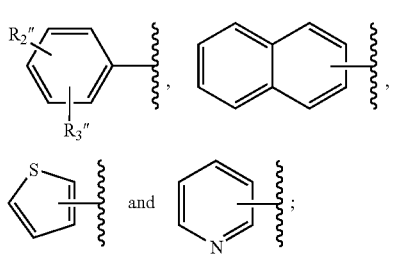

R$_2$" and R$_3$" are, independently, H, (C$_{1-6}$)alkyl, OH, OCH$_3$, OCH$_2$CH$_2$OH, OCH$_2$CO$_2$H, OCH$_2$(CH$_2$)$_n$N(CH$_3$)$_2$, OCH$_2$(CH$_2$)$_n$-4-morpholino, F, Cl, Br or CF$_3$;
R$_4$" is H or CH$_3$;
R$_5$" is (C$_{1-6}$)alkyl, —CH$_2$—Ar" or Ar";
m is 0 or 1; and
n is 1 or 2;
with the proviso that when A" is Ar" or

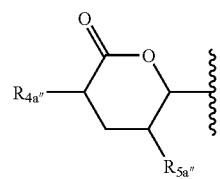

where R$_{4a''}$ is CH$_3$ and R$_{5a''}$ is (C$_{1-6}$)alkyl, then either:
B" cannot be —CH$_2$CH(OH)— or —CH$_2$C(O)— or
C" cannot be —CH═CH—,
or D" cannot be —CH═C(CH$_3$)CH$_2$—,
or E" cannot be —CH(CH$_3$)CH═CHCH═CH$_2$,
or F" cannot be —C(O)NH$_2$,
and with the provisos that when A" is

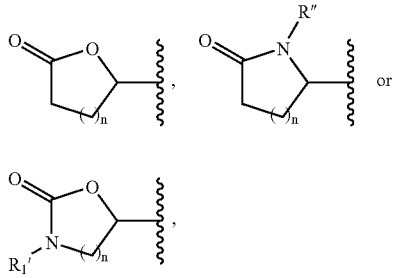

then B" cannot be —OCH$_2$— or —N(R$_1$")C(O)—,
and when B" is —CH$_2$CH(OH)— or —OCH$_2$—,
then C" cannot be —OCH$_2$—, —N(R$_1$")CH$_2$— or —N(R$_1$")C(O)—,
and with the further proviso that the compound of formula Ib is not a compound of formulae

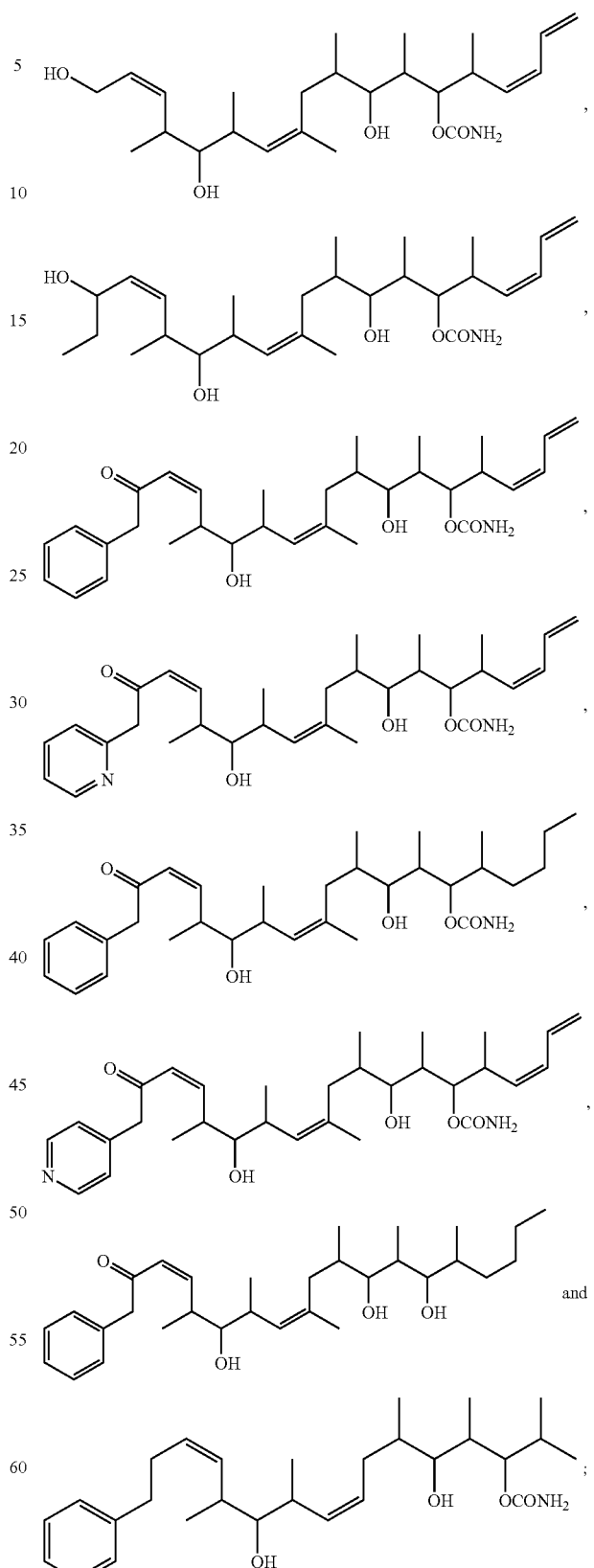

or an acid or base addition salt thereof, where possible.

4. A compound according to claim 3 of formula Ic

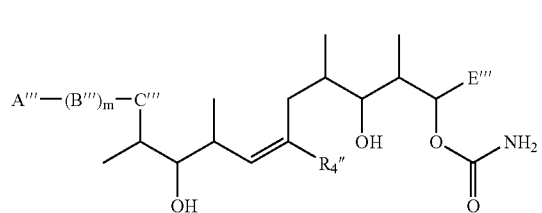

Ic

A''' is (C$_{1-6}$)alkyl;
B''' is —CH$_2$CH(OR$_{1'''}$)—;
C''' is —CH=CH—;
E''' is —CH(R$_{4'''}$)CH=CHCH=CH$_2$;
R$_{1'''}$ is H, —CH$_3$, CH$_2$—Ar''' or Ar''';
Ar''' is selected from

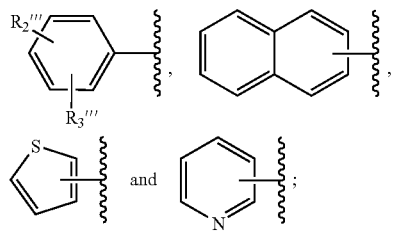

and

R$_{2'''}$ and R$_{3'''}$ are, independently, H, (C$_{1-4}$)alkyl, OH, OCH$_3$, OCH$_2$CO$_2$H, OCH$_2$(CH$_2$)$_n$N(CH$_3$)$_2$, OCH$_2$(CH$_2$)$_n$-4-morpholino, F, Cl, Br or CF$_3$;
R$_{4''}$ is as defined above;
R$_{5'''}$ is (C$_{1-6}$)alkyl, —CH$_2$—Ar''' or Ar''';
m is 0 or 1; and
n is 1 or 2;
with the proviso that when A''' is Ar''' or

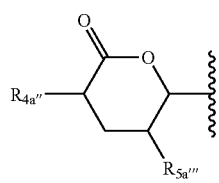

where R$_{4a''}$ is as defined in claim 3 and R$_{5a'''}$ is (C$_{1-6}$)alkyl, then either:
B''' cannot be —CH$_2$CH(OH)— or —CH$_2$C(O)—,
or C''' cannot be —CH=CH—,
or D''' cannot be —CH=C(CH$_3$)CH$_2$—,
or E''' cannot be —CH(CH$_3$)CH=CHCH=CH$_2$,
or F''' cannot be —C(O)NH$_2$,
and with the provisos that when A''' is

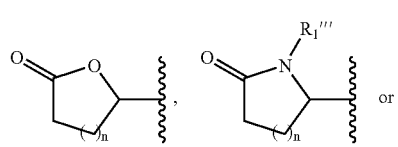

or

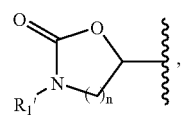

then B''' cannot be —OCH$_2$— or —N(R$_{1'''}$)C(O)—,
and when B''' is —CH$_2$CH(OH)— or —OCH$_2$—,
then C''' cannot be —OCH$_2$—, —N(R$_{1'''}$)CH$_2$— or —N(R$_{1'''}$)C(O)—,
and with the further proviso that the compound of formula Ic is not a compound of formulae

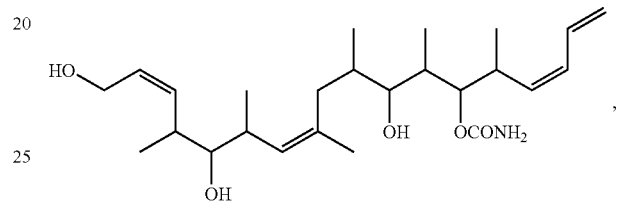

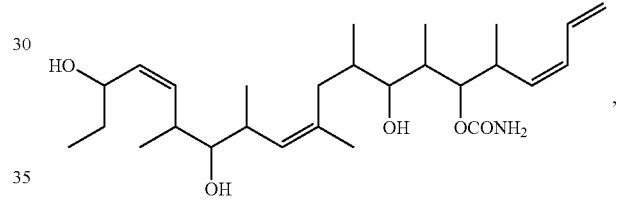

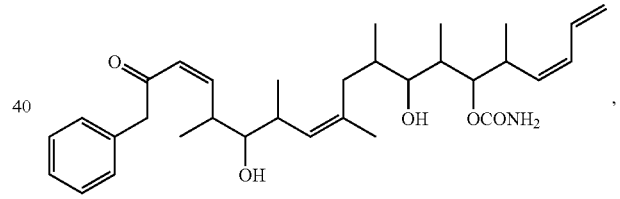

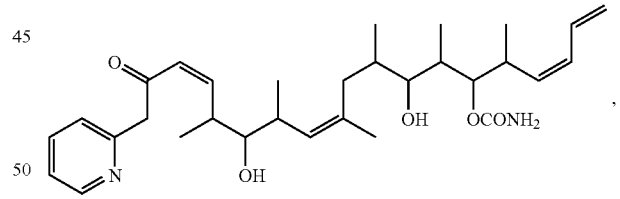

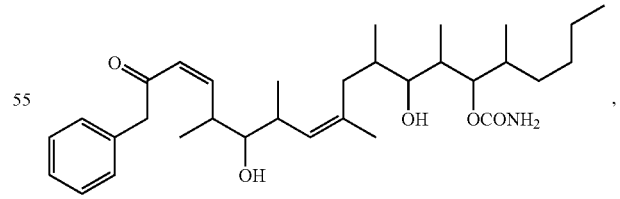

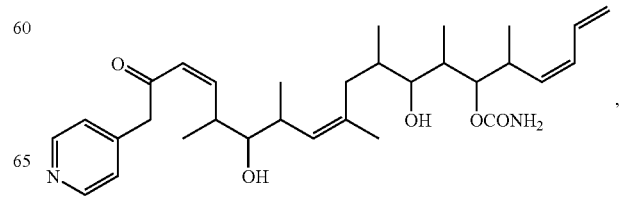

-continued

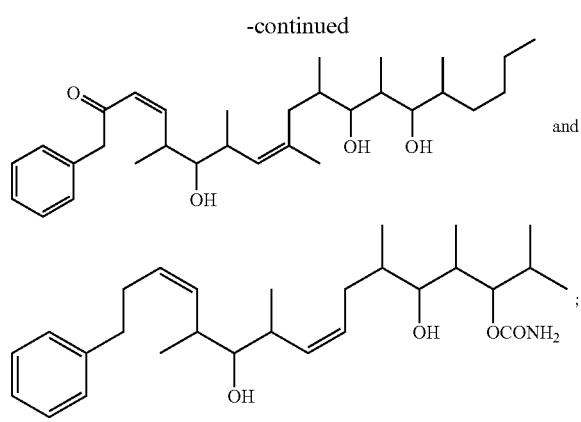

or an acid or base addition salt thereof, where possible.

5. A compound according to claim 1 of formula 1, or a pharmaceutically acceptable acid or base addition salt thereof, where possible.

6. A compound according to claim 2 of formula Ia, or a pharmaceutically acceptable acid or base addition salt thereof, where possible.

7. A compound according to claim 3 of formula Ib, or a pharmaceutically acceptable acid or base addition salt thereof, where possible.

8. A compound according to claim 4 of formula Ic, or a pharmaceutically acceptable acid or base addition salt thereof, where possible.

9. A compound selected from (2S,3Z,5S,6S,7S,8Z,11S, 12R,13R,14S,15S,16Z)-1-isopropyl-5,7,9,11,13,15-hexamethyl-3,8,16,18-nonadecatetraene-2,6,12,14-tetrol-14-carbamate, or a pharmaceutically acceptable acid or base addition salt thereof.

10. A pharmaceutical composition comprising a pharmaceutically acceptable carrier or diluent and a therapeutically effective amount of a compound according to claim 5, or a pharmaceutically acceptable acid or base addition salt thereof, where possible.

11. A pharmaceutical composition comprising a pharmaceutically acceptable carrier or diluent and a therapeutically effective amount of a compound according to claim 6, or a pharmaceutically acceptable acid or base addition salt thereof, where possible.

12. A pharmaceutical composition comprising a pharmaceutically acceptable carrier or diluent and a therapeutically effective amount of a compound according to claim 7, or a pharmaceutically acceptable acid or base addition salt thereof, where possible.

13. A pharmaceutical composition comprising a pharmaceutically acceptable carrier or diluent and a therapeutically effective amount of a compound according to claim 8, or a pharmaceutically acceptable acid or base addition salt thereof, where possible.

14. A pharmaceutical composition comprising a pharmaceutically acceptable carrier or diluent and a therapeutically effective amount of a compound according to claim 9, or a pharmaceutically acceptable acid or base addition salt thereof, where possible.

15. A method of treating colon cancer, which is sensitive to MIP 101 and HCT 116 cell lines tumors comprising administering to a mammal in need of such treatment a therapeutically effective amount of a compound according to claim 5, or a pharmaceutically acceptable acid or base addition salt thereof, where possible.

16. A method of treating colon cancer, which is sensitive to MIP 101 and HCT 116 cell lines comprising administering to a mammal in need of such treatment a therapeutically effective amount of a compound according to claim 6, or a pharmaceutically acceptable acid or base addition salt thereof, where possible.

17. A method of treating colon cancer, which is sensitive to MIP 101 and HCT 116 cell lines comprising administering to a mammal in need of such treatment a therapeutically effective amount of a compound according to claim 7, or a pharmaceutically acceptable acid or base addition salt thereof, where possible.

18. A method of treating colon cancer, which is sensitive to MIP 101 and HCT 116 cell lines comprising administering to a mammal in need of such treatment a therapeutically effective amount of a compound according to claim 8, or a pharmaceutically acceptable acid or base addition salt thereof, where possible.

19. A method of treating colon cancer, which is sensitive to MIP 101 and HCT 116 cell lines comprising administering to a mammal in need of such treatment a therapeutically effective amount of a compound according to claim 9, or a pharmaceutically acceptable acid or base addition salt thereof, where possible.

* * * * *